US011198722B2

(12) United States Patent
Chen et al.

(10) Patent No.: US 11,198,722 B2
(45) Date of Patent: Dec. 14, 2021

(54) IMMUNE TOLERANT ELASTIN-LIKE PEPTIDE TETRAMER GUIDED NANOPARTICLES AND METHODS OF USE

(71) Applicant: University of Utah Research Foundation, Salt Lake City, UT (US)

(72) Inventors: Mingnan Chen, Salt Lake City, UT (US); Peng Zhao, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 225 days.

(21) Appl. No.: 16/152,825

(22) Filed: Oct. 5, 2018

(65) Prior Publication Data

US 2019/0106479 A1   Apr. 11, 2019

Related U.S. Application Data

(60) Provisional application No. 62/568,949, filed on Oct. 6, 2017, provisional application No. 62/568,880, filed on Oct. 6, 2017.

(51) Int. Cl.
| | |
|---|---|
| C07K 14/78 | (2006.01) |
| A61K 39/00 | (2006.01) |
| C07K 16/28 | (2006.01) |
| A61K 39/395 | (2006.01) |
| A61K 9/00 | (2006.01) |
| A61P 35/00 | (2006.01) |
| A61K 9/51 | (2006.01) |
| C07K 14/36 | (2006.01) |
| A61K 38/16 | (2006.01) |
| A61K 38/39 | (2006.01) |
| A61K 47/34 | (2017.01) |
| A61K 9/107 | (2006.01) |
| A61K 39/39 | (2006.01) |

(52) U.S. Cl.
CPC ............ *C07K 14/78* (2013.01); *A61K 9/0019* (2013.01); *A61K 9/1075* (2013.01); *A61K 9/51* (2013.01); *A61K 38/164* (2013.01); *A61K 38/39* (2013.01); *A61K 39/0011* (2013.01); *A61K 39/001111* (2018.08); *A61K 39/39* (2013.01); *A61K 39/3955* (2013.01); *A61K 47/34* (2013.01); *A61P 35/00* (2018.01); *C07K 14/36* (2013.01); *C07K 16/2818* (2013.01); *A61K 2039/505* (2013.01); *A61K 2039/54* (2013.01); *A61K 2039/55555* (2013.01); *A61K 2039/585* (2013.01); *A61K 2039/876* (2018.08); *C07K 2317/565* (2013.01); *C07K 2317/622* (2013.01); *C07K 2319/20* (2013.01); *C07K 2319/21* (2013.01); *C07K 2319/30* (2013.01)

(58) Field of Classification Search
CPC combination set(s) only.
See application file for complete search history.

(56) References Cited

U.S. PATENT DOCUMENTS

| | | | |
|---|---|---|---|
| 4,703,004 | A | 10/1987 | Hopp et al. |
| 4,851,341 | A | 7/1989 | Hopp et al. |
| 5,476,766 | A | 12/1995 | Gold et al. |
| 5,503,978 | A | 4/1996 | Schneider et al. |
| 5,587,455 | A | 12/1996 | Berger et al. |
| 5,631,146 | A | 5/1997 | Szostak et al. |
| 5,696,237 | A | 12/1997 | FitzGerald et al. |
| 5,731,424 | A | 3/1998 | Toothman et al. |
| 5,767,260 | A | 6/1998 | Whitlow et al. |
| 5,780,228 | A | 7/1998 | Parma et al. |
| 5,792,613 | A | 8/1998 | Schmidt et al. |
| 5,795,721 | A | 8/1998 | Rabin et al. |
| 5,846,713 | A | 12/1998 | Pagratis et al. |
| 5,856,456 | A | 1/1999 | Whitlow et al. |
| 5,858,660 | A | 1/1999 | Eaton et al. |
| 5,861,254 | A | 1/1999 | Schneider et al. |
| 5,864,026 | A | 1/1999 | Jensen et al. |
| 5,869,641 | A | 2/1999 | Jayasena et al. |
| 5,914,254 | A | 6/1999 | Mascarenhas et al. |
| 5,958,691 | A | 9/1999 | Pieken et al. |
| 5,981,177 | A | 11/1999 | Demirjian et al. |
| 5,994,104 | A | 11/1999 | Anderson et al. |
| 6,001,988 | A | 12/1999 | Parma et al. |
| 6,011,020 | A | 1/2000 | Gold et al. |
| 6,013,443 | A | 1/2000 | Heilig et al. |
| 6,020,130 | A | 2/2000 | Gold et al. |

(Continued)

FOREIGN PATENT DOCUMENTS

| | | |
|---|---|---|
| CA | 2986766 | 11/2017 |
| CN | 20168003664.1 | 1/2018 |

(Continued)

OTHER PUBLICATIONS

Affiymetrix eBioscience table from http://tools.thermofisher.com/content/sfs/brochures/Mouse_Haplotype_Table.pdf (printed Oct. 2020).*
MBL International Corporation Blog by Declommenne (Jan. 20, 2017).*
Cho et al (Journal Drug Target, 2016, 24:328-339).*
Zhao et al (Molecular Pharmaceuticals, Mar. 25, 2017, 14:1494-1500).*
Dong et al (Molecular Pharmaceuticals, Aug. 8, 2017, 14:3312-3321).*
Dong et al (Acta Pharmacologica Sinica, Apr. 2017, 38:914-923).*

(Continued)

*Primary Examiner* — Laura B Goddard
(74) *Attorney, Agent, or Firm* — Ballard Spahr LLP

(57) ABSTRACT

Disclosed herein, are nanoparticles comprising one or more immune-tolerant elastin-like polypeptide tetramers and one or more immune-tolerant elastin-like fusion molecules. Also, disclosed herein are pharmaceutical compositions including the nanoparticles; methods of administering the nanoparticles to patients for the treatment of cancer; and methods of making the nanoparticles.

30 Claims, 10 Drawing Sheets

Specification includes a Sequence Listing.

(56) References Cited

U.S. PATENT DOCUMENTS

| | | | |
|---|---|---|---|
| 6,028,186 | A | 2/2000 | Tasset et al. |
| 6,030,776 | A | 2/2000 | Eaton et al. |
| 6,051,698 | A | 4/2000 | Janjic et al. |
| 2005/0079184 | A1 | 4/2005 | Hsing-Chang et al. |
| 2010/0273979 | A1 | 10/2010 | Abrahmsen et al. |
| 2012/0121611 | A1 | 5/2012 | Lodie et al. |
| 2012/0121709 | A1 | 5/2012 | Chilkoti et al. |
| 2013/0164340 | A1 | 6/2013 | Easley et al. |
| 2013/0202626 | A1 | 8/2013 | Linke et al. |
| 2014/0099254 | A1 | 4/2014 | Chang et al. |
| 2016/0362460 | A1 | 12/2016 | Olwill et al. |

FOREIGN PATENT DOCUMENTS

| | | |
|---|---|---|
| EP | 16804094.7 | 12/2017 |
| JP | 2017-561974 | 11/2017 |
| WO | WO-1998/022577 A1 | 5/1998 |
| WO | WO-1998/036087 A1 | 8/1998 |
| WO | WO-2015/051001 A2 | 4/2015 |
| WO | WO-2015/157595 A1 | 10/2015 |

OTHER PUBLICATIONS

Adair-Kirk, T.L. et al., A Chemotactic Peptide from Laminin α5 Functions as a Regulator of Inflammatory Immune Responses via TNF α-mediated Signaling. J Immunol. 2005; 174(3):1621-9.

Adair-Kirk, T.L. et al., A Site on Laminin α5, AQARSAASKVKVSMKF, Induces Inflammatory Cell Production of Matrix Metalloproteinase-9 and Chemotaxis. J Immunol. 2003; 171(1):398-406.

Agata, Y. et al., Expression of the PD-1 antigen on the surface of stimulated mouse T and B lymphocytes. Int Immunol. 1996; 8(5):765-72.

Aharoni, R. et al., Neurogenesis and neuroprotection induced by peripheral immunomodulatory treatment of experimental autoimmune encephalomyelitis. J Neurosci. 2005; 25(36):8217-28.

Ahmad, Z.A. et al., scFv Antibody: Principles and Clinical Application. Clin Dev Immunol. 2012; 2012:980250 (15 pages).

American Autoimmune Related Diseases Association I. Autoimmune Statistics 2015. Available from: <https://www.aarda.org/autoimmune-information/autoimmune-statistics/> (24 pages).

Ansari, M.J. et al., The Programmed Death-1 (PD-1) Pathway Regulates Autoimmune Diabetes in Nonobese Diabetic (NOD) Mice. J Exp Med. 2003; 198(1):63-9.

Arévalo-Herrera, M. et al., Preclinical Vaccine Study of *Plasmodium vivax* Circumsporozoite Protein Derived-Synthetic Polypeptides Forumlated in Montanide ISA 720 and Montanide ISA 51 Adjuvants. Am J Trop Med Hyg. 2011; 84(2 Suppl):21-7.

Atanackovic, D. et al., Vaccine-Induced CD4+ Cell Responses to MAGE-3 Protein in Lung Cancer Patients. J Immunol. 2004; 172(5):3289-96.

Atkinson, M.A. et al., Type 1 Diabetes. Lancet. 2014; 383(9911):69-82.

Bachmann, M.F. et al., Vaccine Delivery: a Matter of Size, Geometry, Kinetics and Molecular Patterns. Nat Rev Immunol. 2010; 10(11):787-96.

Bae, Y. and Kataoka, K., Intelligent Polymeric Micelles from Functional Poly(ethylene glycol)-Poly(amino acid) Block Copolymers. Adv Drug Deliv Rev. 2009; 61(10):768-84.

Baghirova, S. et al., Sequential Fractionation and Isolation of Subcellular Proteins from Tissue or Cultured Cells. MethodsX. 2015; 2:440-5.

Baksh, K. et al., Immune checkpoint protein inhibition for cancer: preclinical justification for CTLA-4 and PD-1 blockade and new combinations. Semin Onco. 2015; 42(3):363-77.

Barnden, M.J. et al., Defective TCR Expression in Transgenic Mce Constructed Using cDNA-Based α- and β-chain Genes Under the Control of Heterologous Regulatory Elements. Immunol Cell Biol. 1998; 76(1):34-40.

Begum-Haque, S. et al., Downregulation of IL-17 and IL-6 in the central nervous system by glatiramer acetate in experimental autoimmune encephalomyelitis. J Neuroimmunol. 2008; 204(1-2):58-65.

Bloom, M.B. et al., Identification of Tyrosinase-Related Protein 2 as a Tumor Rejection Antigen for the B16 Melanoma. J Exper Med. 1997; 185(3):453-9.

Bluestone, J.A. et al., Genetics, pathogenesis and clinical interventions in type 1 Idiabetes. Nature. 2010; 464(7293):1293-300 (19 pages).

Brahmer, J.R. et al., Safety and activity of anti-PD-L1 ntibody in patients with advanced cancer. N Engl J Med. 2012; 366(26):2455-65.

Carter, L.L. et al., PD-1/PD-L1, but not PD-1/PD-L2, interactions regulate the severity of experimental autoimmune encephalomyelitis. J Neuroimmunol. 2007; 182(1-2):124-34.

Chan, J. et al., Transplantation of bone marrow genetically engineered to express proinsulin II protects against autoimmune insulitis in NOD mice. J Gene Med. 2006; 8(11):1281-90.

Chapon, M. et al., Progressive Upregulation of PD-1 in Primary and Metastatic Melanomsa Associated with Blunted TCR Signaling in Infilrating T L Lymphocytes. J Inveest Dermatol. 2011; 131(6):1300-7.

Chatenoud, L. et al., Anti-CD3 antibody induces long-term remission of overt autoimmunity in nonobese diabetic mice. Proc natl Acad Sci USA. 1994; 91(1):123-7.

Chen, D.S. et al., Oncology Meets Immunology: The Cancer-Immunity Cycle. Immunity. 2013; 39(1):1-10.

Chen, M. and Bouvier, M., Analysis of interactions in a tapasin/class I complex provides a mechanism for peptide selection. EMBO J. 2007; 26(6):1681-90.

Chen, X. et al., Fusion Protein Linkers: Property, Design and Functionality. Adv Drug Deliv Rev. 2013; 65:1357-69.

Cho, S. et al., Immune-tolerant elastin-like polypeptides (iTEPs) and their application as CTL vaccine carriers. J Drug Target. 2016; 24(4):328-39.

Clawson, C. et al., Delivery of a peptide via Poly(d,l-lactic-co-glycolic) Acid Nanoparticles Enhances Its Dendritic Cell—Stimulatory Capacity. Nanomedicine. 2010; 6(5):651-61.

Constantinescu, C.S. et al., Experimental autoimmune encephalomyelitis (EAE) as a model for multiple sclerosis (MS). Br J Pharmacol. 2011; 164(4):1079-106.

Cuesta, Á.M. et al., Multivalent Antibodies: When Design Surpasses Evolution. Trends Biotechnol. 2010; 28(7):355-62.

Curran, M.A. et al., PD-1 and CTLA-4 Combination Blockade Expands Infiltrating T Cells and Reduces Regulatory T and Myeloid Cells Within B16 Melanoma Tumors. Proc Natl Acad Sci USA. 2010; 107(9):4275-80.

Davila, E. et al., Generation of Antitumor Immunity by Cytotoxic T Lymphocyte Epitope Peptide Vaccination, CpG-oligodeoxynucleotide Adjuvant, and CTLA-4 Blockade. Cancer Res. 2003; 63(12):3281-8.

De Haan, L. et al., Enhanced Delivery of Exogenus Peptides into the Class I Antigen Processing and Presentation Pathway. Infec Immun. 2002; 70(6):3249-58.

De Marco, A., Strategies for Successful Recombinant Expression of Disulfide Bond-Dependent Proteins in *Escherichia coli*. Microbial Cell Fact. 2009; 8:26 (18 pages).

Deyev, S.M. et al., Multivalency: the Hallmark of Antibodies Used for Optimization of Tumor Targeting by Design. Bioessays. 2008; 30(9):904-18.

Dong, S. et al., A Comparison Study of iTEP Nanoparticle-Based CTL Vaccine Carriers Revealed a Surprise relationship Between the Stability and Efficiency of the Carriers. Theranostics. 2016; 6(5):666-78.

Dreher, M.R. et al., Temperature Triggered Self-Assembly of Polypeptides into Multivalent Spherical Micelles. J Am Chem Soc. 2008; 130(2):687-94.

Dyall, R. et al., Heteroclitic Immunization Induces Tumor Immunity. J Exper Med. 1998; 188(9):1553-61.

Elsegeiny, W. et al., Anti-CD20 antibody therapy and susceptibility to Pneumocystis pneumonia. Infect Immun. 2015; 83(5):2043-52.

(56) References Cited

OTHER PUBLICATIONS

Farber, R. et al., Novel Agents for Relapsing Forms of Multiple Sclerosis. Annu Rev Med. 2016; 67:309-21.
Farooqi, N. et al., Are current disease-modifying therapeutics in multiple sclerosis justified on the basis of studies in experimental autoimmune encephalomyelitis? J Neurochem. 2010; 115(4):829-44.
Francisco, L.M. et al., The PD-1 Pathway in Tolerance and Autoimmunity. Immunological Rev. 2010; 236:219-42.
Fransen, M.F. et al., Controlled local delivery of CTLA-4 blocking antibody induces CD8+ T-cell-dependent tumor eradication and decreases risk of toxic side effects. Clin Cancer Res. 2013; 19(19):5381-9.
Frebel, H. et al., The risks of targeting co-inhibitory pathways to modulate pathogen-directed T-cell responses. Trends Immunol. 2013; 34(5):193-9.
Fu, J. et al., Preclinical Evidence that PD1 Blockade Cooperates with Cancer Vaccine TEGVAX to Elicit Regression of Established Tumors. Cancer Res. 2014; 74(15):4042-52.
Fujihashi, K. et al., Cytokine-Specific ELISPOT Assay Single Cell Analysis of IL-2, IL-4 and IL-6 Producing Cells. J Immunol Meth. 1993; 160(2):181-9.
Gardiner, D. et al., A Randomized, Double-Blind, Placebo-Controlled Assessment of BMS-936558, a fully Human Monoclonal Antibody to Programmed Death-1 (PD-1), in Patients with Chronic Hepatitis C virus Infection. PLoS One. 2013; 8(5):e63818 (11 pages).
Gelao, L. et al., Immune checkpoint blockade in cancer treatment: a double-edged sword cross-targeting the host as an "innocent bystander." Toxins. 2014; 6(3):914-33.
Genzyme. Lemtrada (alemtuzumab) hightlights of prescribing information. Cambridge, MA: 2014 (28 pages).
Gomez-Tourino, I. et al., T cells in type 1 diabetes: Instructors, regulators and effectors: A comprehensive review. J Autoimmun. 2016; 66:7-16.
Gubin, M.M. et al., Checkpoint Blockade Cancer Immunotherapy Targets Tumor-Specific Mutatnt Antigens. Nature. 2014; 515(7528):577-81.
Hamid, O. et al., Safety and tumor responses with lambrolizumab (anti-PD-1) in melanoma. N Engl J Med. 2013; 369(2):134-44.
Hamilton, S.E. et al., Quantitation of CD8+ T Cell Expansion, Memory, and Protective Immunity After Immunization with Peptide-coated Dendritic Cells. J Immunol. 2002; 169(9):4936-44.
Herbst, R.S. et al., Predictive correlates of response to the anti-PD-L1 antibody MPDL3280A in cancer patients. Nature. 2014; 515(7528):563-7 (18 pages).
Hernandez, A. et al., Multiple Sclerosis. In: Rose NRM, I.R., editor. The Autoimmune Diseases. 5th ed. New York: Elsevier; 2014. pp. 735-755.
Hersh, C. and Fox R. Multiple Sclerosis: The Cleveland Clinic Foundation; 2014. Available from: [Retrieved from URL: <http://www.clevelandclinicmeded.com/medicalpubs/diseasemanagement/neurology/multiplesclerosis/>] [Retrieved on Jan. 22, 2019] (16 pages).
Hirano, F. et al., Blockade of B7-H1 and PD-1 by Monoclonal Antibodies Potentiates Cancer Therapeutic Immunity. Cancer Res. 2005; 65(3):1089-6.
Hirata, S. et al., Prevention of experimental autoimmune encephalomyelitis by transfer of embryonic stem cell-derived dendritic cells expressing myelin oligodendrocyte glycoprotein peptide along with TRAIL or programmed death-1 ligand. J Immunol. 2005; 174(4):1888-97.
Hirsch, R. et al., Effects of in vivo administration of anti-T3 monoclonal antibody on T cell function in mice. I. Immunosuppression of transplantation responses. J Immunol. 1988; 140(11):3766-72.
Hogquist, K.A. et al., T Cell Receptor Antagonist Peptides Induce Positive Selection. Cell. 1994; 76(1):17-27.
Holden, P. et al., Crude Subcellular Fractionation of Cultured Mammalian Cell Lines. BMC Res Notes. 2009; 2:243 (10 pages).
Holmberg, K. et al., TCR Binding Kinetics Measured with MHC Class I Tetramers Reveal a Positive Selecting Peptide with Relatively High Affinity for TCR. J Immunol. 2003; 171(5):2427-34.
Holmgaard, R.B. et al., Indoleamine 2,3-dioxygenase is a Critical Resistance mechanism in Antitumor T Cell Immunotherapy Targeting CTLA-4. J Exper Med. 2013; 210(7):1389-402.
Hughes, J. et al., Precipitation of Autoimmune Diabetes With Anti-PD-1 Immunotherapy. Diabetes Care. 2015; 38(4):e55.
Hugo, W. et al., Genomic and Transcriptomic Features of Response to Anti-PD-1 Therapy in Metastatic Melanoma. Cell. 2016; 165(1):35-44.
In't Veld, P., Insulitis in human type 1 diabetes: The quest for an elusive lesion. Islets. 2011; 3(4):131-8.
Iwai, Y. et al., Involvement of PD-L1 on Tumor Cells in the Escape from Host Immune System and Tumor Immunotherapy by PD-L1 Blockade. Proc Natl Acad Sci USA. 2002; 99(19):12293-7.
Javan, M.R. et al., Downregulation of Immunosuppressive Molecules, PD-1 and PD-L1, but not PD-L2, in the Patients with Multiple Sclerosis. Iran J Allergy Asthma Immunol. 2016; 15(4):296-302.
Joller, N. et al., Immune checkpoints in central nervous system autoimmunity. Immunol Rev. 2012; 248(1):122-39.
Jonsson, A. et al., Engineering of a femtomolar affinity binding protein to human serum albumin. Protein Eng Des Sel. 2008; 21(8):515-27.
Kaech, S.M. et al., Effector and Memory T-Cell Differentiation: Implications for Vaccine Development. Nat Rev Immunol. 2002; 2(4):251-62.
Kim, J.K. et al., Prospects for Targeting PD-1 and PD-L1 in Various Tumor Types. Oncol J Suppl. 2014; 28 (Suppl 3):15-28.
Kochupurakkal, N.M. et al., Blockade of the programmed death-1 (PD1) pathway undermines potent genetic protection from type 1 diabetes. PLoS One. 2014; 9(2):e89561 (11 pages).
Kreutz, M. et al., Targeting Dendritic Cells—Why Bother? Blood. 2013; 121(15):2836-44.
Kuhns, M.S. et al., Cytotoxic T Lymphyocyte Antigen-4 (CTLA-4) Regulates the Size, Reactivity, and Function of a Primed Pool of CD4+ T Cells. Proc Natl Acad Sci USA. 2000; 97(23):12711-6.
Larkin, J., et al., Combined Nivolumab and Ipilimumab or Monotherapy in Untreated Melanoma. N Engl J Med. 2015; 373:23-34.
Latchman, Y.E. et al., PD-L1-deficient mice show that PD-L1 on T cells, antigen-presenting cells, and host tissues negatively regulates T cells. Proc Natl Acad Sci USA. 2004; 101(29):10691-6.
Le, D.T. et al., PD-1 Blockade in Tumors with Mismatch-Repair Deficiency. N Engl J Med. 2015; 372(26):2509-20.
Lens, M., The Role of Vaccine Therapy in the Treatment of Melanoma. Expert Opin Biol Ther. 2008; 8(3):315-23.
Levy, O.E. et al., Novel exenatide analogs with peptidic albumin binding domains: potent anti-diabetic agents with extended duration of action. PLoS One. 2014; 9(2):e87704 (9 pages).
Li, B. et al., Anti-Programmed Death-1 Synergizes with Granulocyte Macrophage Colony-Stimulating Factor-Secreting Tumor Cell Immunotherapy Providing Therapeutic Benefit to Mice with Established Tumors. Clin Cancer Res. 2009; 15(5):1623-34.
Li, W.A. et al., Materials Based Tumor Immunotherapy Vaccines. Curr Opin Immunol. 2013; 25(2):238-45.
Liang, S.C. et al., Regulation of PD-1, PD-L1, and PD-L2 expression during normal and autoimmune responses. Eur J Immunol. 2003; 33(10):2706-16.
Libbey, J.E. et al., The effects of diet on the severity of central nervous system disease: One part of lab-to-lab variability. Nutrition. 2016; 32(7-8):877-83.
Liu, H. et al., Target-Specific Cytotoxic Effects on HER2-expressing Cells by the Tripartite Fusion Toxin ZHER2:2891-ABD-PE38X8, Including a Targeting Affibody Molecule and a Half-Life Extension Domain. Int J Oncol. 2015; 47(2):601-9.
Liu, W. et al Recombinant immunotoxin engineered for low immunogenicity and antigenicity by identifying and silencing human B-cell epitopes. Proc Natl Acad Sci USA. 2012; 109(29):11782-7.
Lladser, A. et al. Intradermal DNA Electroporation Induces Survivin-Specific CTLs, Suppresses Angiogenesis and Confers Protection Against Mouse Melanoma. Cancer Immunol Immunother. 2010; 59(1):81-92.

(56) References Cited

OTHER PUBLICATIONS

Loregian, A. et al., Intranuclear Delivery of an Antiviral Peptide Mediated by the B Subunit of *Escherichia coli* Heat-Labile Enterotoxin. Proc Natl Acad Sci USA. 1999; 96(9):5221-6.
Magnus, T. et al., Microglial expression of the B7 family member B7 homolog 1 confers strong immune inhibition: implications for immune responses and autoimmunity in the CNS. J Neurosci. 2005; 25(10):2537-46.
Makinodan, T. and Kay, M.M., Age influence on the immune system. Advances in immunology. 1980; 29(287):287-330.
Mansour, M. et al., Therapy of Established B16-F10 Melanoma Tumors by a Single Vaccination of CTL/T helper Peptides in VacciMax. J Transl Med. 2007; 5:20 (8 pages).
Mazor, R. et al., Identification and elimination of an immunodominant T-cell epitope in recombinant immunotoxins based on Pseudomonas exotoxin A. Proc Natl Acad Sci USA. 2012; 109(51):E3597-603.
Mazor, R. et al., Recombinant Immunotoxin with T-cell Epitope Mutations that Greatly Reduce Immunogenicity for Treatment of Mesothelin-Expressing Tumors. Mol Cancer Ther. 2015; 14(12):2789-96.
McNamara, C. et al., Current and Emerging Therapies in Multiple Sclerosis: Implications for the Radiologist, Part 2—Surveillance for Treatment Complications and Disease Progression. AJNR Am J Neuroradiol. 2017; 38(9):1672-80.
Mecha, M. et al., Viral models of multiple sclerosis: Neurodegeneration and demyelination in mice infected with Theiler's virus. Prog Neurobiol. 2013; 101-102:46-64.
Medications: National Multiple Sclerosis Society [Retrieved from the Internet on Jan. 25, 2019] [Retrieved from URL: <http://www.nationalmssociety.org/Treating-MS/Medications>] (5 pages).
Michielin, O. et al., Gaining momentum: New options and opportunities for the treatment of advanced a. Cancer Treat Rev. 2015; 4(8):660-70.
Miller, S.D. and Karpus, W.J., Experimental autoimmune encephalomyelitis in the mouse. Curr Protoc Immunol. 2007; Chapter 15:Unit 15 1 (26 pages).
Müller, D. et al., Improved pharmacokinetics of recombinant bispecific antibody molecules by fusion to human serum albumin. J Biol Chem. 2007; 282(17):12650-60.
Murphy, K., Dynamics of Adaptive Immunity. Janway's Immunol. 8 ed. New York, USA: Garland Science; 2012. pp. 429-464.
Myers, K.J., et al., Antisense oligonucleotide blockade of alpha 4 integrin prevents and reverses clinical symptoms in murine experimental autoimmune encephalomyelitis. J Neuroimmunol. 2005;160 (1-2):12-24.
Nathan, D.M., Diabetes: Advances in Diagnosis and Treatment. JAMA. 2015; 314(10):1052-62.
Nishimura, H. et al., Developmentally regulated expression of the PD-1 protein on the surface of double-negative (CD4-CD8-) thymocytes. Int Immunol. 1996 8(5):773-80.
Nishino, M. et al., Anti-PD-1-Related Pneumonitis during Cancer Immunotherapy. N Engl J Medicine. 2015; 373(3):288-90.
Noeman, S.A. et al., Growth of Rat-Mouse Hybridomas in Nude Mice and Nude Rats. J Immunol Meth. 1982; 55(3):319-26.
Noone, A.M. et al., SEER Cancer Statistics Review, 1975-2015, National Cancer Institute. Bethesda, MD. Retrieved from the Internet: URL <https://seer.cancer.gov/csr/1975_2015/, based on Nov. 2017 SEER data submission (Apr. 2018) (27 pages).
Oestreich, K.J. et al, NFATcl Regulates PD-a Expression Upon T-Cell Activation. J Immunol. 2008; 181(7):4832-9.
Okamoto, M. et al., Fulminant type 1 diabetes mellitus with anti-programmed cell death-1 therapy. J Diabetes Invest. 2016; 7(6):915-8.
Okazaki, T. and Honjo, T., PD-1 and PD-1 ligands: from discovery to clinical application. Int Immunol. 2007; 19(7):813-24.
Orlova, A. et al., Site-specific radiometal labeling and improved biodistribution using ABY-027, a novel HER2-targeting affibody molecule-albumin binding domain fusion protein. J Nucl Med. 2013; 54(6):961-8.
Overwijk, W.W. et al., gp100/pmel 17 is a Murie Tumor Rejection Antigen: Induction of "Self"-Reactive, Tumoricidal T Cells Using High-Affinity, Altered Peptide Ligand. J Exper Med. 1998; 188(2):277-86.
Pastan, I. et al., Immunotoxins with decreased immunogenicity and improved activity. Leuk Lymphoma. 2011; 52 (Suppl 2):87-90.
Peggs, K.S. et al., Blockade of CTLA-4 on Both Effector and regulatory T Cell Compartments Contributes to the Antitumor Activity of Anti-CTLA-4 Antibodies. J Exp Med. 2009; 206(8):1717-25.
Penaranda, C. et al., Anti-CD3 therapy promotes tolerance by selectively depleting pathogenic cells while preserving regulatory T cells. J Immunol. 2011; 187(4):2015-22.
Pentcheva-Hoang, T. et al., Negative regulators of T-cell activation: potential targets for therapeutic intervention in cancer, autoimmune disease, and persistent infections. Immunol Rev. 2009; 229(1):67-87.
Perrin, P.J. et al., CTLA-4 Blockade Enhances Clinical Disease and Cytokine Production During Experimental Allergic Encephalomyelitis. J Immunol. 1996; 157(4):1333-6.
Phan, G.Q. et al., Immunization of Patients with Metastatic Melanoma Using Both Class I- and Class II-Restricted Peptides from Melanoma-Associated Antigens. J Immunother. 2003; 26(4):349-56.
Pol, J. et al., Trial Watch: Peptide-Based Anticancer Vaccines. Oncoimmunology. 2015; 4(4):e974411 (12 pages).
Purcell, A.W. et al., More Than One Reason to Rethink the Use of Peptides in Vaccine Design. Nat Rev Drug Discov. 2007; 6(5):404-14.
Quezada, S.A. et al., CTLA-4 Blockade and GM-CSF Combination Immunotherapy Alters the Intratumor Balance of Effector and Regulatory T Cells. J Clin Invest. 2006; 116(7):1935-45.
Rangachari, M. and Kuchroo, V.K., Using EAE to better understand principles of immune function and autoimmune pathology. J Autoimmun. 2013; 45:31-9.
Read, S. et al., Blockade of CTLA-4 on CD4+CD25+ regulatory T cells abrogates their function in vivo. J Immunol. 2006; 177(7):4376-83.
Reik, L.M. et al., A Simple, Non-Chromatographic Purification Procedure for Monoclonal Antibodies. Isolation of Monoclonal Antibodies Against Cytochrome P450 Isozymes. J Immunol Meth. 1987; 100(1-2):123-30.
Rissiek et al, Nanobodies as Modulators of Inflammation: Potential Applications for Acute Brain Injury. Front Cell Neurosci. 2014; 8:344 (7 pages).
Rizvi, N.A. et al., Mutational Landscape Determines Sensitivity to PD-1 Blockade in Non-Small Cell Lung Cancer. Science. 2015; 348(6230):124-8.
Robbins, P.F. et al., Mining exomic sequencing data to identify mutated antigens recognized by adoptively transferred tumor-reactive T-cells. Nature Med. 2013; 19(6):747-52.
Robert, C. et al., Ipilimumab Plus Dacarbazine for Previously Untreated Metastatic Melanoma. N Engl J Med. 2011; 364:2517-26.
Sakai, K. et al., Characterization of a major encephalitogenic T cell epitope in SJL/J mice with synthetic oligopeptides of myelin basic protein. J Neuroimmunol. 1988; 19(1-2):21-32.
Sakai, K. et al., Involvement of distinct murine T-cell receptors in the autoimmune encephalitogenic response to nested epitopes of myelin basic protein. Proc Natl Acad Sci USA.1988; 85(22):8608-12.
Salama, A.D. et al., Critical role of the programmed death-1 (PD-1) pathway in regulation of experimental autoimmune encephalomyelitis. J Exp Med. 2003; 198(1):71-8.
Savage, P.A. et al., A Kinetc Basis for T Cell Receptor Repertoire Selection During an Immune Response. Immunity. 1999; 10(4):485-92.
Schreiner, B. et al., PD-1 ligands expressed on myeloid-derived APC in the CNS regulate T-cell responses in EAE. Eur J Immunol. 2008; 38(10):2706-17.
Schultz, J. et al., A Tetravalent Single-Chain Antibody-Streptavidin Fusion Protein for Pretargeted Lymphoma Therapy. Cancer Res. 2000; 60(23):6663-9.

(56) References Cited

OTHER PUBLICATIONS

Sharma, P. et al., Immune checkpoint targeting in cancer therapy: toward combination strategies with curative potential. Cell. 2015; 161(2):205-14.
Shoda, L.K. et al., A comprehensive review of interventions in the NOD mouse and implications for translation. Immunity. 2005; 23(2):115-26.
Stubig, T. et al., 5-Azacytidine Promotes an Inhibitory T-Cell Phenotype and Impairs Immune Mediated Antileukemic Activity. Med Inflamm. 2014; 2014:418292 (12 pages).
Swaika, A. et al., Current state of anti-PD-L1 and anti-PD-1 agents in cancer therapy. Mol Immunol. 2015; 67(2, Part A): 4-17.
Tarhini, A., Immune-mediated adverse events associated with ipilimumab ctla-4 blockade therapy: the underlying mechanisms and clinical management. Scientifica (Cairo). 2013; 2013:857519 (19 pages).
Teuscher, C. et al., Evidence that the Y chromosome influences autoimmune disease in male and female mice. Proc Natl Acad Sci USA. 2006; 103(21):8024-9.
Theien, B.E. et al., Differential effects of treatment with a small-molecule VLA-4 antagonist before and after onset of relapsing EAE. Blood. 2003; 102(13):4464-71.
Tompkins, S.M. et al., De Novo Central Nervous System Processing of Myelin Antigen is Required for the Initiation of Experimental Autoimmune Encephalomyelitis. J Immunol. 2002; 168(8):4173-83.
Topalian, S.L. et al., Safety, activity, and immune correlates of anti-PD-1 antibody in cancer. N Engl J Med. 2012; 366(26):2443-54.
Topalian, S.L. et al., Targeting the PD-1/B7-H1 (PD-L1) pathway to activate anti-tumor immunity. Curr Opin Immunol. 2012; 24(2):207-12.
Torkildsen, O. et al., Disease-modifying treatments for multiple sclerosis—a review of approved medications. Eur J Neurol. 2016; 23:18-27.
Trabattoni, D. et al., Costimulatory pathways in multiple sclerosis: distinctive expression of PD-1 and PD-L1 in patients with different patterns of disease. J Immunol. 2009; 183(8):4984-93.
Tsunoda, I. et al., Contrasting roles for axonal degeneration in an autoimmune versus viral model of multiple sclerosis: When can axonal injury be beneficial? Am J Pathol. 2007; 170(1):214-26.
Tumeh, P.C. et al., PD-1 Blockade Induces Responses by Inhibiting Adaptive Immune Resistance. Nature. 2014; 515(7528):568-71.
Turner MJ. et al., Immune status following alemtuzumab treatment in human CD52 transgenic mice. J Neuroimmunol. 2013; 261(1-2):29-36.
U.S. Food & Drug Administration, pembrolizumab (KEYTRUDA) Prescribing Information. Retrieved from the Internet: <URL: https://www.accessdata.fda.gov/drugsatfda_docs/label/2016/125514s009lbl.pdf> 2016 (26 pages).
Uchi, H.S. et al., Unraveling the complex relationship between cancer immunity and autoimmunity: lessons from melanoma and vitiligo. Adv Immunol. 2006; 90:215-41.
Vainshtein, I. et al., Quantitative Measurement of the Target-Mediated Internalization Kinetics of Biopharmaceuticals. Phar mRes. 2015; 32(1):286-99.
Van Belle, T.L. et al., Type 1 diabetes: etiology, immunology, and therapeutic strategies. Physiol Rev. 2011; 91(1):79-118.
Van Broekhoven, C.L. et al., Targeting Dendritic Cells with Antigen-Containing Lipsomes: A Highly Effective Procedure for Induction of Antitumor Immunity and for Tumor Immunotherapy. Cancer Res. 2004; 64(12):4357-65.
Van Elsas, A. et al., Combination Immunotherapy of B16 Melanoma Using Anti-Cytotoxic T Lymphocyte-Associated Antigen 4 (CTLA-4) and Granulocyte/Macrophage Colony-Stimulating Factor (GM-CSF)-Producing Vaccines Induces Rejection of Subcutaneous and Metastatic Tumors Accompanied by Autoimmune Depigmentation. J Exp Med. 1999; 190(3):355-66.
Van Rooij, N. et al., Tumor Exome Analysis Reveals Neoantigen-Specific T-Cell Reactivity in an Ipilimumab-Responsive Melanoma. J Clin Oncol. 2013; 31(32):e439-42.
Walker, E. and Nowacki, A.S., Understanding equivalence and noninferiority testing. J Gen Intern Med. 2011;26(2):192-6.
Wang, C. et al., In situ activation of platelets with checkpoint inhibitors for post-surgical cancer immunotherapy. Nat Biomed Eng. 2017; 1:0011 (10 pages).
Wang, C. et al., in Vitro Characterization of the Anti-PD-1 Antibody Nivolumab, BMS-936558, and in Vivo. Toxicology in Non-Human Primates. Cancer Immunol Res. 2014; 2(9):846-56.
Weldon, J.E. and Pastan, I., A guide to taming a toxin—recombinant immunotoxins constructed from Pseudomonas exotoxin A for the treatment of cancer. FEBS J. 2011; 278(23):4683-700.
Weldon, J.E. et al., A protease-resistant immunotoxin against CD22 with greatly increased activity against CLL and diminished animal toxicity. Blood. 2009; 113(16):3792-800.
Weldon, J.E. et al., A recombinant immunotoxin against the tumor-associated antigen mesothelin reengineered for high activity, low off-target toxicity, and reduced antigenicity. Mol Cancer Ther. 2013; 12(1):48-57.
Wingerchuk, D.M. and Carter, J.L., Multiple sclerosis: current and emerging diseasemodifying therapies and treatment strategies. Mayo Clin Proc. 2014; 89(2):225-40.
Wolchok, J.D. et al., Nivolumab plus ipilimumab in advanced melanoma. N Engl J Med. 2013; 369(2):122-33.
Yamazaki, T. et al., Blockade of B7-H1 on macrophages suppresses CD4+ T cell proliferation by augmenting IFN-gamma-induced nitric oxide production. J Immunol. 2005; 175(3):1586-92.
Yamazaki, T. et al., Expression of programmed death 1 ligands by murine T cells and APC. J Immunol. 2002; 169(10):5538-45.
Yang, K. et al., Deficiency of Thrombospondin-1 Reduces Th17 Differenctiation and Attenuates Experimental Autoimmune Encephalomyelitis. J Autoimmun. 2009; 32(2):94-103.
Ye, Q. et al., CD137 Accurately Identifies and Enriches for naturally Occurring Tumor-Reactive T Cells in Tumor. Clin Cancer Res. 2014; 20(1):44-55.
Yousef, S. et al., Cancer-testis Antigen SLLP1 Represents a Promising Target for the Immunotherapy of Multiple Myeloma. J Trans Med. 2015; 13(1):197 (12 pages).
Zamora-Avila, D.E. et al., WT1 Gene Silencing by Aerosol Delivery of PEO-RNAi Complexes Inhibits B16-F10 Lung Metastases Growth. Cancer Gene Ther. 2009; 16(12):892-9.
Zamvil, S.S. et al., Multiple discrete encephalitogenic epitopes of the autoantigen myelin basic protein include a determinant for I-E class II-restricted T cells. J Exp Medicine. 1988; 168(3):1181-6.
Zarour, H.M. et al., NY-ES0-1 119-143 is a Promiscuous major Histocompatibiliy Complex Class II T-Helper Epitope Recognized by TH1- and TH2-Type Tumor-Reactive CD4+ T Cells. Cancer Res. 2002; 62(1):213-8.
Zhang, Q. and Vignali, D.A., Co-stimulatory and Co-inhibitory Pathways in Autoimmunity. Immunity. 2016; 44(5):1034-51.
Zhang, Y. et al., PKSolver: An Add-in Program for Pharmacokinetic and Pharmacodynamic Data Analysis in Microsoft Excel. Comput Meth Prog Biomed. 2010; 99(3):306-14.
Zhao, P. et al., An Anti-Programmed Death-1 Antibody (aPD-1) Fusion Protein That Self-Assembles into a Multivalent and Functional aPD-1 Nanoparticle. Mol Pharm. 2017; 14(5):1494-500.
Zhao, P. et al., An iTEP-Salinomycin Nanoparticle That Specifically and Effectively Inhibits Metastases of 4T1 Orthotopic Breast Tumors. Biomaterials. 2016; 93:1-9.
Zhao, P. et al., iTEP nanoparticle-delivered salinomycin displays an enhanced toxicity to cancer stem cells in orthotopic breast tumors. Mol Pharm. 2014; 11(8):2703-12.
Zhao, S. et al., Regulation of Neuroinflammation through Programmed Death-1/Programed Death Ligand Signaling in Neurological Disorders. Front Cell Neurosci. 2014; 8:271 (7 pages).
Zhou, Z. et al., Type 1 diabetes associated HLA-DQ2 and DQ8 molecules are relatively resistant to HLA-DM mediated release of invariant chain-derived CLIP peptides. Eur J Immunol. 2016; 46(4):834-45.
Zhu, B. et al., Differential role of programmed death-ligand 1 [corrected] and programmed death-ligand 2 [corrected] in regulat-

(56) References Cited

OTHER PUBLICATIONS ing the susceptibility and chronic progression of experimental autoimmune encephalomyelitis. J immunol. 2006; 176(6):3480-9.
International Search Report and Written Opinion dated Jan. 4, 2019 by the International Searching Authority for Patent Application No. PCT/US2018/054645, which was filed on Oct. 5, 2018 (Inventor—Chen et al.; Applicant—University of Utah Research Foundation; (19 pages).
U.S. Appl. No. 62/568,949, filed Oct. 6, 2017, Mingnan Chen (Univ. of Utah Res. Found.).
U.S. Appl. No. 62/568,880, filed Oct. 6, 2017, Mingnan Chen (Univ. of Utah Res. Found.).
PCT/US2018/054645, Oct. 5, 2018, Mingnan Chen (Univ. of Utah Res. Found.).
Office Action dated Jun. 22, 2020 by the Japanese Patent Office for Application No. 2017-561974, (Applicant—University of Utah Research Foundation) (3 pages).
Zhao et al., Itep Nanoparticle-Delivered Salinomycin Displays an Enhanced Toxicity to Cancer Stem Cells in Orthotropic Breast Tumors. Molecular pharmaceutics. 2014; 11:2703-2712.
Chung et al., Sequences and domain structures of mammalian, avian, amphibian and teleost tropoelastins: Clues to the evolutionary history of elastins (Matrix Biology 25 (2006) 492-504).
Non Final Office Action Issued by the USPTO dated Sep. 21, 2020 for U.S. Appl. No. 15/577,998, filed Nov. 29, 2017, ( 12 pages).
U.S. Appl. No. 62/230,160, filed May 29, 2015, Mingnan Chen (Univ. of Utah Res. Found.).
U.S. Appl. No. 62/309,113, filed Mar. 16, 2016, Mingnan Chen (Univ. of Utah Res. Found.).
U.S. Appl. No. 15/577,998, filed Nov. 29, 2017, Mingnan Chen (Univ. of Utah Res. Found.).
U.S. Appl. No. 62/890,936, filed Aug. 23, 2019, Mingnan Chen (Univ. of Utah Res. Found.).
PCT/US2016/034530, filed May 27, 2016, Mingnan Chen (Univ. of Utah Res. Found.).
PCT/US2020/040230, Jun. 30, 2020, Mingnan Chen (Univ. of Utah Res. Found.).
Alexander, J. et al., A decaepitope polypeptide primes for multiple CD8+ IFN-y and Th lymphocyte responses: evaluation of multiepitope polypeptides as a mode for vaccine delivery. J Immunol.2002; 168(12):6189-98.
Bastianello et al., A Chronic Cardiomyopathy in Feedlot Cattle Attributed to Toxic Levels of Salinomycin in the Feed. J S Afr Vet Accos. 1996; 67(1):38-41.
Benitez, P.L. et al., Sequence-specific crosslinking of electrospun, elastin-like protein preserves bioactivity and native-like mechanics. Adv Healthc Mater. 2013; 2(1):114-8 (10 pages).
Bernard, A. et al., T and B cell cooperation: a dance of life and death. Transplantation. 2005; 79(3 Suppl):58-11.
Bidwell, G.L. 3rd et al., Thermally targeted delivery of a c-Myc inhibitory polypeptide inhibits tumor progression and extends survival in a rat glioma model. PLoS one. 2013; 8(1):e55104 (12 pages).
Brooks, P. et al., Subcellular Localoization of Proteasomes and Their Regulatory Complexes in Mammalian Cells. Biochem J. 2000; 346(Pt 1): 155-61.
Cantin, A.M et al., Normal Alveolar Epithelial Lining Fluid Contains High Levels of Glutathione. J Appl Physiol. 1987; 63(1):152-7.
Cappello. J., in Handbook of Biodegradable Polymers, A. J. Domb; J. Kost; D. M. Wiseman, Eds. (Harwood Academic Publishers, Amsterdam, 1997), pp. 387-416.
Chen et al., Abstract 2816: Immune-Tolerant Elastin-like Polypeptide (iTEP) Particles Promote Peptide Vaccine Presentation by Dendritic Cells. Cancer Res. 2014; 74(19). Abstract only (2 pages).
Chilkoti, A. et al., Targeted drug delivery by thermally responsive polymers. Adv Drug Deliv Rev. 2002; 54(5):613-30.
Christiansen, M. et al., Weekly Subcutaneous Doses of Glymera (PB1023) a Novel GLP-1 Analogue Reduce Glucose Exposure Dose-Dependently. (Philadelphia, Pennsylvania, 2012) (1 page).

Da Silva, D.M. et al., Effect of preexisting neutralizing antibodies on the anti-tumor immune response induced by chimeric human papillomavirus virus-like particle vaccines. Virology. 2001; 290(2):350-60.
De Groot, A.S. and Scott, D.W., Immunogenicity of protein therapeutics. Trends Immunol. 2007; 28(11):482-90.
Epstein, J.E. et al., Live Attenuated Malaria Vaccine Designed to Protect Through Hepatic CD8+ T Cell Immunity. Science. 2011; 334:475-80.
Fang, J. et al., The EPR Effect: Unique Features of Tumor Blood Vessels for Drug Delivery, Factors Involved, and Limitations and Augmentation of the Effect. Adv Drug Deliv Rev. 2011; 63(3):136-51.
Feldmann, M. and Easten, A., The Relationship Between Antigenic Structure and the Requirement for Thymus-Derived Cells in the Immune Response. J Exp Med. 1971; 134(1):103-19.
Frey, A. et al., A statistically defined endpoint titer determination method for immunoassays. J Immunol Methods. 1998; 221(1-2):35-41.
Garcia-Arevalo, C. et al., Immunomodulatory nanoparticles from elastin-like recombinamers: single-molecules for tuberculosis vaccine development. Mol Pharm. 2013; 10(2):586-97.
Goldberg, M.S., Immunoengineering: How Nanotechnology Can Enhance Cancer Immunotherapy. Cell. 2015; 161(2):201-4.
Hassouneh, W. et al., Elastin-like polypeptides as a purification tag for recombinant proteins. Curr Protoc Protein. 2010; Chapter 6:Unit 6.11 (20 pages).
Hassouneh, W. et al., Unexpected multivalent display of proteins by temperature triggered self-assembly of elastin-like polypeptide block copolymers. Biomacromolecules. 2012; 13(5):1598-605 (17 pages).
Jefferis, R., Aggregation, immune complexes and immunogenicity MAbs. 2010; 3(6):503-4.
Jones, D.P. et al., Glutathione Measurement in Human Plasma. Evaluation of Sample Collection, Storage and Derivatization Conditions for Analysis of Dansyl Derivatives by HPLC. Clin Chim Acta. 1998; 275(2):175-84.
Karttunen, J. et al., Detection of Rare Antigen-Presenting Cells by the lacZ T-Cell Activation Assay Suggests an Expression Cloning Strategy for T-Cell Antigens. Proc Natl Acad Sci USA. 1992; 89(13):6020-4.
Kaspar, A.A. and Reichert, J.M., Future directions for peptide therapeutics development. Drug discovery today. 2013; 18(17-18):807-17.
Klebanoff, C.A. et al., Therapeutic Cancer Vaccines: Are We There Yet? Immunol Rev. 2011; 239(1 ):27-44.
Kloetzel, P.-M. and Ossendorp, F., Proteasome and Peptidase Function in MHO-Class-I-Mediated Antigen Presentation. Curr Opin Immunol. 2004; 16(1):76-81.
Kontos, S. and Hubbell, J.A., Drug development: longer-lived proteins. Chem Soc Rev. 2012; 41(7):2686-95.
Kovacs-Nolan, J. and Mine, Y., Tandem copies of a human rotavirus VP8 epitope can induce specific neutralizing antibodies in BALB/c mice Biochim BiophysActa. 2006; 1760(12):1884-93.
Kruger, E. and Kloetzel, P.-M., Immunoproteasesomes at the Interface of Innate and Adaptive Immune Responses: Two Faces of One Enzyme. Curr Opin Immunol. 2012; 24(1):77-83.
Le, D.H. et al., Self-assembly of elastin-mimetic double hydrophobic polypeptides. Biomacromolecules. 2013; 14(4):1028-34.
Lee, C. et al., Copper staining: a five-minute protein stain for sodium dodecyl sulfatepolyacrylamide gels. Anal Biochem. 1987; 166(2):308-12 (7 pages).
Liu, J. et al., Endocytic uptake of a large array of HPMA copolymers: Elucidation into the dependence on the physicochemical characteristics. J Control Release. 2010; 143(1):71-9 (24 pages).
Liu, W. et al., High epitope density in a single recombinant protein molecule of the extracellular domain of influenza A virus M2 protein significantly enhances protective immunity. Vaccine. 2004; 23(3):366-71.
Liu, X.S. et al., IL-10 mediates suppression of the CD8 T cell IFN-y response to a novel viral epitope in a primed host. J Immunol. 2003; 171:4765-72.

(56) References Cited

OTHER PUBLICATIONS

Livingston, B.D. et al., Optimization of epitope processing enhances immunogenicity of multiepitope DNA vaccines. Vaccine. 2001; 19(32):4652-60.

MacEwan, S.R. and Chilkoti, A., Elastin-like polypeptides: biomedical applications of tunable biopolymers. Biopolymers. 2010; 94(1):60-77.

MacKay, J.A. et al., Self-assembling chimeric polypeptide-doxorubicin conjugate nanoparticles that abolish tumours after a single injection. Nat Mater. 2009; 8(12):993-9 (18 pages).

Matsumura et al., A New Concept for Macromolecular Therapeutics in Cancer Chemotherapy: Mechanism of Tumoritropic Accumulation of Proteins and the Antitumor Agent Smancs. Cancer Res. 1986; 46(12 part 1):6387-92.

McDaniel, J.R. et al., Recursive directional ligation by plasmid reconstruction allows rapid and seamless cloning of oligomeric genes. Biomacromolecules. 2010; 11(4):944-52 (20 pages).

Moreland, L.W. et al., Phase I/II trial of recombinant methionyl human tumor necrosis factor binding protein PEGylated dimer in patients with active refractory rheumatoid arthritis. J Rheumatol. 2000; 27:601-9.

Moroy, G. et al., Structural Characterization of Human Elastin Derived Peptides Containing the GXXP Sequence. Biopolymers. 2005; 78(4):206-20.

Nouri, F.S. et al., Reducing the Visibility of the Vector/DNA Nanocomplexes to the Immune System by Elastin-Like Peptides. Pharm Res. 2015; 32(9):3018-28.

Ohyanagi, F. et al., Safety of BLP25 Liposome Vaccine (L-BLP25) in Japanese Patients with Unresectable Stage III NSCLC After Primary Chemoradiotherapy: Preliminary Resuls from a Phase I/II Study. Jpn J clin Oncol. 2011; 41 (5):718-22.

Onda, M. et al., An immunotoxin with greatly reduced immunogenicity by identification and removal of B cell epitopes. Proc Natl Acad Sci USA. 2008; 105(32):11311-6.

Onda, M. et al., Characterization of the B cell epitopes associated with a truncated form of Pseudomonas exotoxin (PE38) used to make immunotoxins for the treatment of cancer patients. J Immunol. 2006; 177(12):8822-34.

Parker, D.C., T cell-dependent B cell activation. Annu Rev Immunol. 1993; 11:331-60.

Partidos, C. et al., The influence of orientation and 5 number of copies of T and B cell epitopes on the specificity and affinity of antibodies induced by chimeric peptides. Eur J Immunol. 1992; 22(10):2675-80.

Petros, R.A. and DeSimone, J.M., Strategies in the Design of Nanoparticles for Therapeutic Applications. Nat Rev Drug Discov. 2010; 9(8):615-27.

Plummer, E.M. and Manchester, M., Viral Nanoparticles and Virus-like Particles: Platforms for Contemporary Vaccine Design. WIREs Nanomed Nanobiotechnol. 2011; 3(2):174-96.

Rau, R. et al., Intravenous human recombinant tumor necrosis factor receptor p55-Fe IgG1 fusion protein Ro 45-2081 (Lenercept): a double blind, placebo controlled dose-finding study in rheumatoid arthritis. J Rheumatol. 2003; 30(4):680-90.

Robinson, H.L. and Amara, R.R., T Cell Vaccines for Microbial Infections. Nat Med. 2005; 11 (4 Suppl):s25-32.

Rock, K L. et al., Peptide-priming of cytolytic T cell immunity in vivo using 32-microglobulin as an adjuvant. J Immunol. 1993; 150(4):1244-52.

Rosenberg, A.S., Effects of protein aggregates: an immunologic perspective. AAPS J. 2006; 8(3):E501-7.

Ruedl, C. et al., Virus-like particles as carriers for T-cell epitopes: limited inhibition of T-cell priming by carrier-specific antibodies. J Virol. 2005; 79(2):717-24.

Sandev, P. et al., Biomaterials for Nanoparticle Vaccine Delivery Systems. Pharm Res. 2014; 31(10):2563-82 (35 pages).

Scheller, J. et al., Forcing single-chain variable fragment production in tobacco seeds by fusion to elastin-like polypeptides. Plant Biotechnol J. 2006; 4(2):243-9.

Schumacher, R. et al., Efficient Induction of Tumoricidal Cytotoxic T Lymphocytes by HLA-A0201 Restricted, Melanoma Associated, L27Melan-A/MART-1 26-35 Peptide Encapsulated into Virosomes In Vitro. Vaccine. 2005; 23(48-49):5572-82.

Sela, M., Antigenicity: some molecular aspects. Science. 1969; 166(3911):1365-74.

Shankar, G. et al., Scientific and regulatory considerations on the immunogenicity of biologics. Trends Biotechnol. 2006; 24(6):274-80.

Shen, Z. et al., Cloned dendritic cells can present exogenous antigens on both MHC class I and class II molecules. J Immunol. 1997; 158(6):2723-30.

Shi, P. et al., Elastin-based protein polymer nanoparticles carrying drug at both corona and core suppress tumor growth in vivo. J Control Release. 2013; 171(3):330-8 (21 pages).

Smejkal, G.B., The Coomassie chronicles: past, present and future perspectives in polyacrylamide gel staining. Expert Rev Proteomics. 2004; 1(4):381-7.

Smith, C.V. et al., Compartmentation of Glutathione: Implications for the Study of Toxicity and Disease. Toxicol Appl Pharmacol. 1996; 140(1):1-12.

Tao, K. et al., Imagable 4T1 Model for the Study of Late Stage Breast Cancer. BMC Cancer. 2008; 8(1):228 (20 pages).

Thomson, S.A. et al., Minimal epitopes expressed in a recombinant polyepitope protein are processed and presented to CD8+ cytotoxic T cells: implications for vaccine design. Proc Natl Acad Sci USA. 1995; 92(13):5845-9.

Urry, D.W. and Parker, T.M., Biocompatibility of the Bioelastic Materials, Poly(GVGVP) and Its y-Irradiation Cross-Linked Matrix: Summary of Generic Biological Test Results. J Bioactiv Compatible Polymers. 1991; 6(3):263-82.

Urry, D.W. et al., Temperature of Polypeptide Inverse Temperature Transition Depends on Mean Residue Hydrophobicity. J Am Chern Soc. 1991; 113:4346-8.

Urry, D.W., Free energy transduction in polypeptides and proteins based on inverse temperature transitions. Prog Biophys Mol Biol. 1992; 57(1):23-57 (split into 2 parts).

Urry, D.W., Physical Chemistry, of Biological Free Energy Transduction as Demonstrated by Elastic Protein-Based Polymers. J Phys Chem B. 1997; 101:11007-28.

Van Regenmortel, M. H., Chapter 1: Molecular Dissection of Protein Antigens. Structure of Antigens. M. H. Van Regenmortel, Ed. CRC Press, 1992. pp. 1-28.

Wu, G. et al., Glutathione Metabolism and Its Implications for Health. J Nutr. 2004; 134(3):489-92.

Yewdell, J.W. and Bennink, J.R., Cut and Trim: Generating MHC Class I Peptide Ligands. Curr Opin Immunol. 2001; 13(1):13-8.

Zhang, Y. et al., The Eradication of Breast Cancer Stem Cells Using Octreotide Modified Paclitaxel Active Targeting Micelles and Salinomycin Passive Targeting Micelles. Biomaterials. 2012;33(2):679-91.

Zhang, Z. et al., Paclitaxel Drug Delivery Systems. Expert Opin Drug Deliv. 2013; 10(3):325-40.

Zhou, L. et al., Stratification of Antibody-Positive Subjects by Antibody Level Reveals an Impact of Immunogenicity on Pharmacokinetics. AAPS J. 2013; 15(1):30-40.

Supplementary European Search Report dated Jan. 21, 2019 by the European Patent Office for Patent Application No. 16804094.7, which was filed on May 27, 2016 and published as EP 3302531 on Apr. 11, 2018 (Inventor-Chen et al.; Applicant-University of Utah Research Foundation) (8 pages).

International Search Report and Written Opinion dated Oct. 31, 2016 by the International Searching Authority for Patent Application No. PCT/US2016/034530, which was filed on May 27, 2016 and published as WO 2016/196249 on Dec. 8, 2016 (Inventor-Chen et al.; Applicant-University of Utah Research Foundation) (13 pages).

International Preliminary Report on Patentability dated Dec. 5, 2017 by the International Searching Authority for Patent Application No. PCT/US2016/034530, which was filed on May 27, 2016 and

(56) References Cited

OTHER PUBLICATIONS published as WO 2016/196249 on Dec. 8, 2016 (Inventor-Chen et al.; Applicant-University of Utah Research Foundation) (7 pages).

* cited by examiner

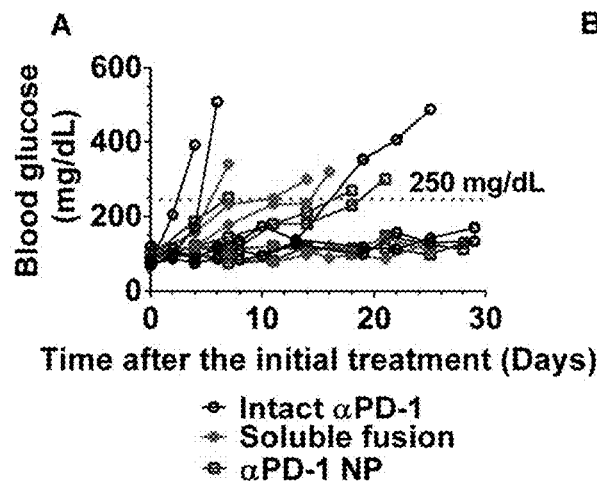
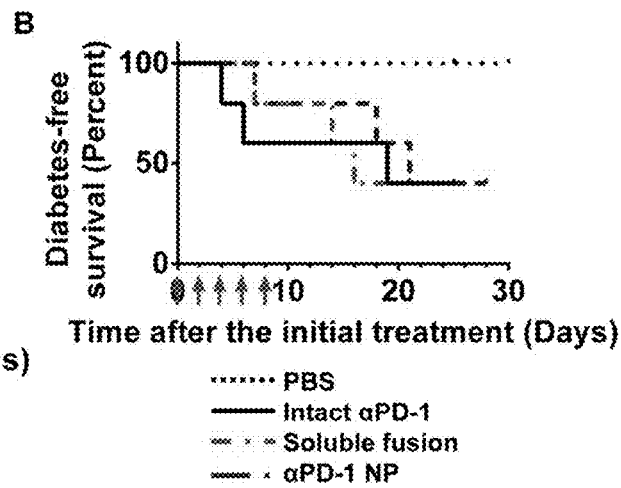
Fig. 4A
Fig. 4B
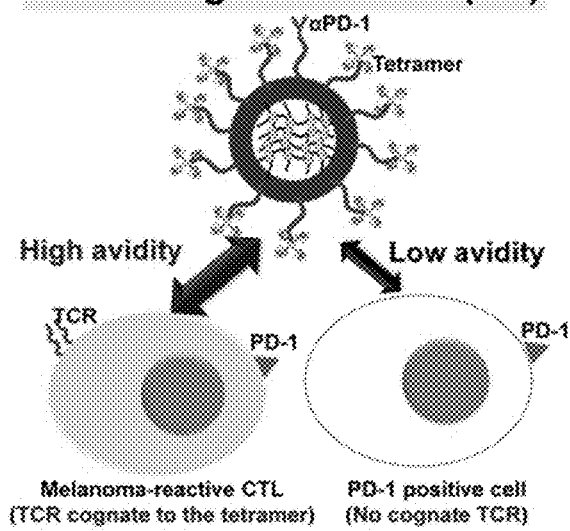
Fig. 5

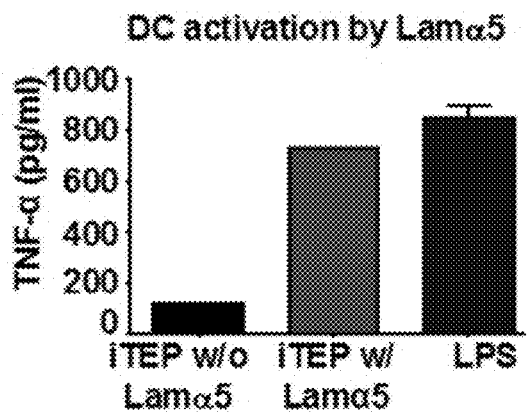
Fig. 13
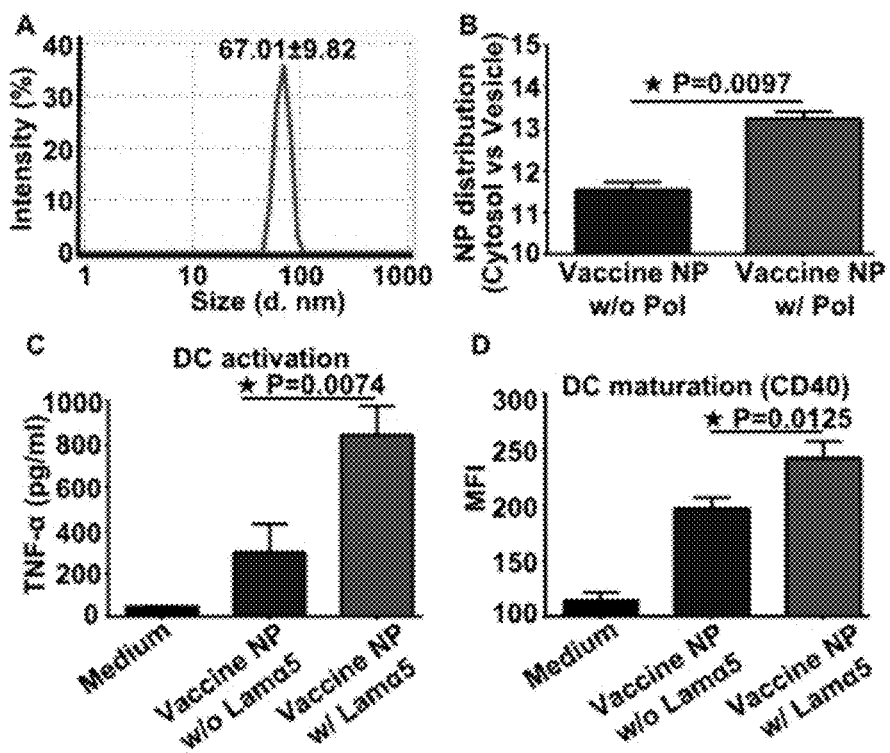
Fig. 14A
Fig. 14B
Fig. 14C
Fig. 14D

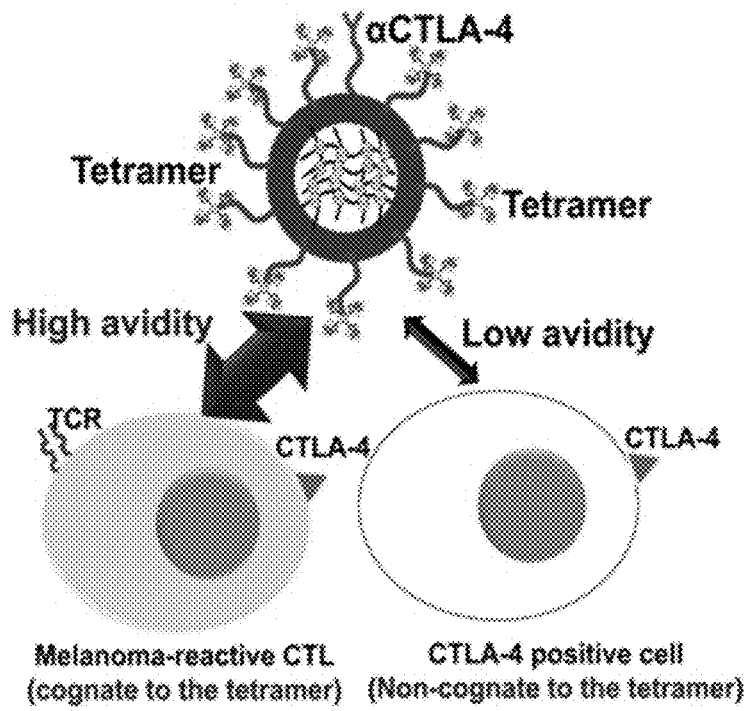
Fig. 18
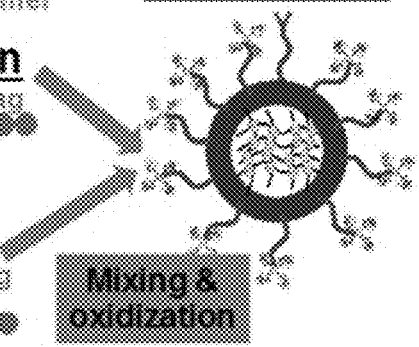

SEQUENCE LISTING

<160> NUMBER OF SEQ ID NOS: 47

<210> SEQ ID NO 1
<211> LENGTH: 7
<212> TYPE: PRT
<213> ORGANISM: Artificial Sequence
<220> FEATURE:
<223> OTHER INFORMATION: Synthetic construct

<400> SEQUENCE: 1

Gly Val Leu Pro Gly Val Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic construct

<400> SEQUENCE: 2

Gly Ala Gly Val Pro Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Val Pro Gly Phe Gly Ala Gly Ala Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Val Pro Gly Leu Gly Ala Gly Ala Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic construct

<400> SEQUENCE: 5

Val Pro Gly Leu Gly Val Gly Ala Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Gly Val Leu Pro Gly Val Gly Gly
1               5

```
<210> SEQ ID NO 7
<211> LENGTH: 5
<212> TYPE: PRT
<213> ORGANISM: Artificial Sequence
<220> FEATURE:
<223> OTHER INFORMATION: Synthetic construct

<400> SEQUENCE: 7

Gly Val Leu Pro Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic construct

<400> SEQUENCE: 8

Gly Leu Val Pro Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Gly Leu Val Pro Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic construct

<400> SEQUENCE: 10

Gly Val Pro Leu Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic construct

<400> SEQUENCE: 11

Gly Ile Pro Gly Val Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic construct

<400> SEQUENCE: 12

Gly Gly Val Leu Pro Gly
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: Synthetic construct

<400> SEQUENCE: 13

Gly Val Leu Pro Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synethtic construct

<400> SEQUENCE: 14

Gly Val Gly Val Leu Pro Gly
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic construct

<400> SEQUENCE: 15

Gly Val Pro Gly
1

<210> SEQ ID NO 16
<211> LENGTH: 16
<212> TYPE: PRT
<213> ORGANISM: Artificial Sequence
<220> FEATURE:
<223> OTHER INFORMATION: Synthetic construct

<400> SEQUENCE: 16

Ala Gln Ala Arg Ser Ala Ala Ser Lys Val Lys Val Ser Met Lys Phe
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic construct

<400> SEQUENCE: 17

Ala Lys Phe Val Ala Ala Trp Thr Leu Lys Ala Ala Ala
1               5                   10

<210> SEQ ID NO 18
<211> LENGTH: 21
<212> TYPE: PRT
<213> ORGANISM: Artificial Sequence
<220> FEATURE:
<223> OTHER INFORMATION: Synthetic construct

<400> SEQUENCE: 18

Met Glu Val Gly Trp Tyr Arg Ser Pro Phe Ser Arg Val Val His Leu
1               5                   10                  15

Tyr Arg Asn Gly Lys
```

```
<210> SEQ ID NO 19
<211> LENGTH: 10
<212> TYPE: PRT
<213> ORGANISM: Artificial Sequence
<220> FEATURE:
<223> OTHER INFORMATION: Synthetic construct

<400> SEQUENCE: 19

Ala Val Gly Ala Gly Ala Thr Ala Glu Glu
1               5                   10

<210> SEQ ID NO 20
<211> LENGTH: 420
<212> TYPE: PRT
<213> ORGANISM: Artificial Sequence
<220> FEATURE:
<223> OTHER INFORMATION: Synthetic construct

<400> SEQUENCE: 20

Gly Ala Gly Val Pro Gly Gly Ala Gly Val Pro Gly Gly Ala Gly Val
1               5                   10                  15

Pro Gly Gly Ala Gly Val Pro Gly Gly Ala Gly Val Pro Gly Gly Ala
            20                  25                  30

Gly Val Pro Gly Gly Ala Gly Val Pro Gly Gly Ala Gly Val Pro Gly
        35                  40                  45

Gly Ala Gly Val Pro Gly Gly Ala Gly Val Pro Gly Gly Ala Gly Val
    50                  55                  60

Pro Gly Gly Ala Gly Val Pro Gly Gly Ala Gly Val Pro Gly Gly Ala
65                  70                  75                  80

Gly Val Pro Gly Gly Ala Gly Val Pro Gly Gly Ala Gly Val Pro Gly
                85                  90                  95

Gly Ala Gly Val Pro Gly Gly Ala Gly Val Pro Gly Gly Ala Gly Val
            100                 105                 110

Pro Gly Gly Ala Gly Val Pro Gly Gly Ala Gly Val Pro Gly Gly Ala
        115                 120                 125

Gly Val Pro Gly Gly Ala Gly Val Pro Gly Gly Ala Gly Val Pro Gly
    130                 135                 140

Gly Ala Gly Val Pro Gly Gly Ala Gly Val Pro Gly Gly Ala Gly Val
145                 150                 155                 160

Pro Gly Gly Ala Gly Val Pro Gly Gly Ala Gly Val Pro Gly Gly Ala
                165                 170                 175

Gly Val Pro Gly Gly Ala Gly Val Pro Gly Gly Ala Gly Val Pro Gly
            180                 185                 190

Gly Ala Gly Val Pro Gly Gly Ala Gly Val Pro Gly Gly Ala Gly Val
        195                 200                 205

Pro Gly Gly Ala Gly Val Pro Gly Gly Ala Gly Val Pro Gly Gly Ala
    210                 215                 220

Gly Val Pro Gly Gly Ala Gly Val Pro Gly Gly Ala Gly Val Pro Gly
225                 230                 235                 240

Gly Ala Gly Val Pro Gly Gly Ala Gly Val Pro Gly Gly Ala Gly Val
                245                 250                 255

Pro Gly Gly Ala Gly Val Pro Gly Gly Ala Gly Val Pro Gly Gly Ala
            260                 265                 270

Gly Val Pro Gly Gly Ala Gly Val Pro Gly Gly Ala Gly Val Pro Gly
        275                 280                 285
```

Gly Ala Gly Val Pro Gly Gly Ala Gly Val Pro Gly Gly Ala Gly Val
        290                 295                 300

Pro Gly Gly Ala Gly Val Pro Gly Gly Ala Gly Val Pro Gly Gly Ala
305                 310                 315                 320

Gly Val Pro Gly Gly Ala Gly Val Pro Gly Gly Ala Gly Val Pro Gly
                325                 330                 335

Gly Ala Gly Val Pro Gly Gly Ala Gly Val Pro Gly Gly Ala Gly Val
            340                 345                 350

Pro Gly Gly Ala Gly Val Pro Gly Gly Ala Gly Val Pro Gly Gly Ala
        355                 360                 365

Gly Val Pro Gly Gly Ala Gly Val Pro Gly Gly Ala Gly Val Pro Gly
370                 375                 380

Gly Ala Gly Val Pro Gly Gly Ala Gly Val Pro Gly Gly Ala Gly Val
385                 390                 395                 400

Pro Gly Gly Ala Gly Val Pro Gly Gly Ala Gly Val Pro Gly Gly Ala
                405                 410                 415

Gly Val Pro Gly
            420

<210> SEQ ID NO 21
<211> LENGTH: 392
<212> TYPE: PRT
<213> ORGANISM: Artificial Sequence
<220> FEATURE:
<223> OTHER INFORMATION: Synthetic construct

<400> SEQUENCE: 21

Gly Val Leu Pro Gly Val Gly Gly Val Leu Pro Gly Val Gly Gly Val
1               5                   10                  15

Leu Pro Gly Val Gly Gly Val Leu Pro Gly Val Gly Gly Val Leu Pro
            20                  25                  30

Gly Val Gly Gly Val Leu Pro Gly Val Gly Gly Val Leu Pro Gly Val
        35                  40                  45

Gly Gly Val Leu Pro Gly Val Gly Gly Val Leu Pro Gly Val Gly Gly
    50                  55                  60

Val Leu Pro Gly Val Gly Gly Val Leu Pro Gly Val Gly Gly Val Leu
65                  70                  75                  80

Pro Gly Val Gly Gly Val Leu Pro Gly Val Gly Gly Val Leu Pro Gly
                85                  90                  95

Val Gly Gly Val Leu Pro Gly Val Gly Gly Val Leu Pro Gly Val Gly
            100                 105                 110

Gly Val Leu Pro Gly Val Gly Gly Val Leu Pro Gly Val Gly Gly Val
        115                 120                 125

Leu Pro Gly Val Gly Gly Val Leu Pro Gly Val Gly Gly Val Leu Pro
    130                 135                 140

Gly Val Gly Gly Val Leu Pro Gly Val Gly Gly Val Leu Pro Gly Val
145                 150                 155                 160

Gly Gly Val Leu Pro Gly Val Gly Gly Val Leu Pro Gly Val Gly Gly
                165                 170                 175

Val Leu Pro Gly Val Gly Gly Val Leu Pro Gly Val Gly Gly Val Leu
            180                 185                 190

Pro Gly Val Gly Gly Val Leu Pro Gly Val Gly Gly Val Leu Pro Gly
        195                 200                 205

Val Gly Gly Val Leu Pro Gly Val Gly Gly Val Leu Pro Gly Val Gly
    210                 215                 220

```
Gly Val Leu Pro Gly Val Gly Gly Val Leu Pro Gly Val Gly Gly Val
225                 230                 235                 240

Leu Pro Gly Val Gly Gly Val Leu Pro Gly Val Gly Gly Val Leu Pro
            245                 250                 255

Gly Val Gly Gly Val Leu Pro Gly Val Gly Gly Val Leu Pro Gly Val
        260                 265                 270

Gly Gly Val Leu Pro Gly Val Gly Gly Val Leu Pro Gly Val Gly Gly
    275                 280                 285

Val Leu Pro Gly Val Gly Gly Val Leu Pro Gly Val Gly Gly Val Leu
290                 295                 300

Pro Gly Val Gly Gly Val Leu Pro Gly Val Gly Gly Val Leu Pro Gly
305                 310                 315                 320

Val Gly Gly Val Leu Pro Gly Val Gly Gly Val Leu Pro Gly Val Gly
            325                 330                 335

Gly Val Leu Pro Gly Val Gly Gly Val Leu Pro Gly Val Gly Gly Val
        340                 345                 350

Leu Pro Gly Val Gly Gly Val Leu Pro Gly Val Gly Gly Val Leu Pro
    355                 360                 365

Gly Val Gly Gly Val Leu Pro Gly Val Gly Gly Val Leu Pro Gly Val
370                 375                 380

Gly Gly Val Leu Pro Gly Val Gly
385                 390

<210> SEQ ID NO 22
<211> LENGTH: 8
<212> TYPE: PRT
<213> ORGANISM: Artificial Sequence
<220> FEATURE:
<223> OTHER INFORMATION: Synthetic construct

<400> SEQUENCE: 22

Gly Cys Gly Cys Gly Cys Gly Cys
1               5

<210> SEQ ID NO 23
<211> LENGTH: 20
<212> TYPE: PRT
<213> ORGANISM: Artificial Sequence
<220> FEATURE:
<223> OTHER INFORMATION: Synthetic construct

<400> SEQUENCE: 23

Gly Gly Gly Gly Cys Gly Gly Gly Cys Gly Gly Gly Cys Gly
1               5                   10                  15

Gly Gly Gly Cys
            20

<210> SEQ ID NO 24
<211> LENGTH: 36
<212> TYPE: PRT
<213> ORGANISM: Artificial Sequence
<220> FEATURE:
<223> OTHER INFORMATION: Synthetic construct

<400> SEQUENCE: 24

Gly Gly Gly Gly Gly Gly Gly Cys Gly Gly Gly Gly Gly Gly
1               5                   10                  15

Gly Cys Gly Gly Gly Gly Gly Gly Gly Cys Gly Gly Gly Gly
            20                  25                  30

Gly Gly Gly Cys
```

<210> SEQ ID NO 25
<211> LENGTH: 192
<212> TYPE: PRT
<213> ORGANISM: Artificial Sequence
<220> FEATURE:
<223> OTHER INFORMATION: Synthetic construct

<400> SEQUENCE: 25

```
Gly Val Pro Gly Phe Gly Ala Gly Ala Gly Val Pro Gly Phe Gly Ala
1               5                   10                  15

Gly Ala Gly Val Pro Gly Phe Gly Ala Gly Ala Gly Val Pro Gly Phe
            20                  25                  30

Gly Ala Gly Ala Gly Val Pro Gly Phe Gly Ala Gly Ala Gly Val Pro
        35                  40                  45

Gly Phe Gly Ala Gly Ala Gly Val Pro Gly Phe Gly Ala Gly Ala Gly
    50                  55                  60

Val Pro Gly Phe Gly Ala Gly Ala Gly Val Pro Gly Phe Gly Ala Gly
65                  70                  75                  80

Ala Gly Val Pro Gly Phe Gly Ala Gly Ala Gly Val Pro Gly Phe Gly
                85                  90                  95

Ala Gly Ala Gly Val Pro Gly Phe Gly Ala Gly Ala Gly Val Pro Gly
                100                 105                 110

Phe Gly Ala Gly Ala Gly Val Pro Gly Phe Gly Ala Gly Ala Gly Val
            115                 120                 125

Pro Gly Phe Gly Ala Gly Ala Gly Val Pro Gly Phe Gly Ala Gly Ala
        130                 135                 140

Gly Val Pro Gly Phe Gly Ala Gly Ala Gly Val Pro Gly Phe Gly Ala
145                 150                 155                 160

Gly Ala Gly Val Pro Gly Phe Gly Ala Gly Ala Gly Val Pro Gly Phe
                165                 170                 175

Gly Ala Gly Ala Gly Val Pro Gly Phe Gly Ala Gly Ala Gly Gly Gly
                180                 185                 190
```

<210> SEQ ID NO 26
<211> LENGTH: 877
<212> TYPE: PRT
<213> ORGANISM: Artificial Sequence
<220> FEATURE:
<223> OTHER INFORMATION: Synthetic construct

<400> SEQUENCE: 26

```
Gly Gly Val Pro Gly Leu Gly Ala Gly Ala Gly Val Pro Gly Leu Gly
1               5                   10                  15

Ala Gly Ala Gly Val Pro Gly Leu Gly Ala Gly Ala Gly Val Pro Gly
            20                  25                  30

Leu Gly Ala Gly Ala Gly Val Pro Gly Leu Gly Ala Gly Ala Gly Val
        35                  40                  45

Pro Gly Leu Gly Ala Gly Ala Gly Val Pro Gly Leu Gly Ala Gly Ala
    50                  55                  60

Gly Val Pro Gly Leu Gly Ala Gly Ala Gly Val Pro Gly Leu Gly Ala
65                  70                  75                  80

Gly Ala Gly Val Pro Gly Leu Gly Ala Gly Ala Gly Val Pro Gly Leu
                85                  90                  95

Gly Ala Gly Ala Gly Val Pro Gly Leu Gly Ala Gly Ala Gly Val Pro
                100                 105                 110
```

```
Gly Leu Gly Ala Gly Ala Gly Val Pro Gly Leu Gly Ala Gly
            115                 120                 125
Val Pro Gly Leu Gly Ala Gly Ala Gly Val Pro Gly Leu Gly Ala Gly
130                 135                 140
Ala Gly Val Pro Gly Leu Gly Ala Gly Ala Gly Val Pro Gly Leu Gly
145                 150                 155                 160
Ala Gly Ala Gly Val Pro Gly Leu Gly Ala Gly Ala Gly Val Pro Gly
                165                 170                 175
Leu Gly Ala Gly Ala Gly Val Pro Gly Leu Gly Ala Gly Ala Gly Val
            180                 185                 190
Pro Gly Leu Gly Ala Gly Ala Gly Val Pro Gly Leu Gly Ala Gly Ala
        195                 200                 205
Gly Val Pro Gly Leu Gly Ala Gly Ala Gly Val Pro Gly Leu Gly Ala
    210                 215                 220
Gly Ala Gly Val Pro Gly Leu Gly Ala Gly Ala Gly Val Pro Gly Leu
225                 230                 235                 240
Gly Ala Gly Ala Gly Val Pro Gly Leu Gly Ala Gly Ala Gly Val Pro
                245                 250                 255
Gly Leu Gly Ala Gly Ala Gly Val Pro Gly Leu Gly Ala Gly Ala Gly
            260                 265                 270
Val Pro Gly Leu Gly Ala Gly Ala Gly Val Pro Gly Leu Gly Ala Gly
        275                 280                 285
Ala Gly Val Pro Gly Leu Gly Ala Gly Ala Gly Val Pro Gly Leu Gly
        290                 295                 300
Ala Gly Ala Gly Val Pro Gly Leu Gly Ala Gly Ala Gly Val Pro Gly
305                 310                 315                 320
Leu Gly Ala Gly Ala Gly Val Pro Gly Leu Gly Ala Gly Ala Gly Val
                325                 330                 335
Pro Gly Leu Gly Ala Gly Ala Gly Val Pro Gly Leu Gly Ala Gly Ala
            340                 345                 350
Gly Val Pro Gly Leu Gly Ala Gly Ala Gly Val Pro Gly Leu Gly Ala
        355                 360                 365
Gly Ala Gly Val Pro Gly Leu Gly Ala Gly Ala Gly Val Pro Gly Leu
    370                 375                 380
Gly Ala Gly Ala Gly Val Pro Gly Leu Gly Ala Gly Ala Gly Val Pro
385                 390                 395                 400
Gly Leu Gly Ala Gly Ala Gly Val Pro Gly Leu Gly Ala Gly Ala Gly
                405                 410                 415
Val Pro Gly Leu Gly Ala Gly Ala Gly Val Pro Gly Leu Gly Ala Gly
            420                 425                 430
Ala Gly Val Pro Gly Leu Gly Ala Gly Ala Gly Val Pro Gly Leu Gly
        435                 440                 445
Ala Gly Ala Gly Val Pro Gly Leu Gly Ala Gly Ala Gly Val Pro Gly
    450                 455                 460
Leu Gly Ala Gly Ala Gly Val Pro Gly Leu Gly Ala Gly Ala Gly Val
465                 470                 475                 480
Pro Gly Leu Gly Ala Gly Ala Gly Val Pro Gly Leu Gly Ala Gly Ala
                485                 490                 495
Gly Val Pro Gly Leu Gly Ala Gly Ala Gly Val Pro Gly Leu Gly Ala
            500                 505                 510
Gly Ala Gly Val Pro Gly Leu Gly Ala Gly Ala Gly Val Pro Gly Leu
        515                 520                 525
Gly Ala Gly Ala Gly Val Pro Gly Leu Gly Ala Gly Ala Gly Val Pro
```

```
                535                 540
        530
Gly Leu Gly Ala Gly Ala Gly Val Pro Gly Leu Gly Ala Gly
545                 550                 555                 560

Val Pro Gly Leu Gly Ala Gly Ala Gly Val Pro Gly Leu Gly Ala Gly
                565                 570                 575

Ala Gly Val Pro Gly Leu Gly Ala Gly Ala Gly Val Pro Gly Leu Gly
                580                 585                 590

Ala Gly Ala Gly Val Pro Gly Leu Gly Ala Gly Ala Gly Val Pro Gly
                595                 600                 605

Leu Gly Ala Gly Ala Gly Val Pro Gly Leu Gly Ala Gly Ala Gly Val
                610                 615                 620

Pro Gly Leu Gly Ala Gly Ala Gly Val Pro Gly Leu Gly Ala Gly Ala
625                 630                 635                 640

Gly Val Pro Gly Leu Gly Ala Gly Ala Gly Val Pro Gly Leu Gly Ala
                645                 650                 655

Gly Ala Gly Val Pro Gly Leu Gly Ala Gly Ala Gly Val Pro Gly Leu
                660                 665                 670

Gly Ala Gly Ala Gly Val Pro Gly Leu Gly Ala Gly Ala Gly Val Pro
                675                 680                 685

Gly Leu Gly Ala Gly Ala Gly Val Pro Gly Leu Gly Ala Gly Ala Gly
                690                 695                 700

Val Pro Gly Leu Gly Ala Gly Ala Gly Val Pro Gly Leu Gly Ala Gly
705                 710                 715                 720

Ala Gly Val Pro Gly Leu Gly Ala Gly Ala Gly Val Pro Gly Leu Gly
                725                 730                 735

Ala Gly Ala Gly Val Pro Gly Leu Gly Ala Gly Ala Gly Val Pro Gly
                740                 745                 750

Leu Gly Ala Gly Ala Gly Val Pro Gly Leu Gly Ala Gly Ala Gly Val
                755                 760                 765

Pro Gly Leu Gly Ala Gly Ala Gly Val Pro Gly Leu Gly Ala Gly Ala
                770                 775                 780

Gly Val Pro Gly Leu Gly Ala Gly Ala Gly Val Pro Gly Leu Gly Ala
785                 790                 795                 800

Gly Ala Gly Val Pro Gly Leu Gly Ala Gly Ala Gly Val Pro Gly Leu
                805                 810                 815

Gly Ala Gly Ala Gly Val Pro Gly Leu Gly Ala Gly Ala Gly Val Pro
                820                 825                 830

Gly Leu Gly Ala Gly Ala Gly Val Pro Gly Leu Gly Ala Gly Ala Gly
                835                 840                 845

Val Pro Gly Leu Gly Ala Gly Ala Gly Val Pro Gly Leu Gly Ala Gly
                850                 855                 860

Ala Gly Val Pro Gly Leu Gly Ala Gly Ala Gly Gly
865                 870                 875

<210> SEQ ID NO 27
<211> LENGTH: 12
<212> TYPE: PRT
<213> ORGANISM: Artificial Sequence
<220> FEATURE:
<223> OTHER INFORMATION: Synthetic construct

<400> SEQUENCE: 27

Gly Val Pro Gly Leu Gly Val Gly Ala Gly Gly Gly
1               5                   10
```

```
<210> SEQ ID NO 28
<211> LENGTH: 5
<212> TYPE: PRT
<213> ORGANISM: Artificial Sequence
<220> FEATURE:
<223> OTHER INFORMATION: Synthetic construct

<400> SEQUENCE: 28

Gly Gly Val Pro Gly
1               5

<210> SEQ ID NO 29
<211> LENGTH: 15
<212> TYPE: PRT
<213> ORGANISM: Artificial Sequence
<220> FEATURE:
<223> OTHER INFORMATION: Synthetic construct

<400> SEQUENCE: 29

Gly Gly Gly Gly Ser Gly Gly Gly Gly Ser Gly Gly Gly Gly Ser
1               5                   10                  15

<210> SEQ ID NO 30
<211> LENGTH: 5
<212> TYPE: PRT
<213> ORGANISM: Artificial Sequence
<220> FEATURE:
<223> OTHER INFORMATION: Synthetic construct

<400> SEQUENCE: 30

Gly Gly Gly Gly Ser
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic construct

<400> SEQUENCE: 31

Gly Gly Gly Gly Ser Gly Gly Gly Gly Ser
1               5                   10

<210> SEQ ID NO 32
<211> LENGTH: 20
<212> TYPE: PRT
<213> ORGANISM: Artificial Sequence
<220> FEATURE:
<223> OTHER INFORMATION: Synthetic construct

<400> SEQUENCE: 32

Gly Gly Gly Gly Ser Gly Gly Gly Gly Ser Gly Gly Gly Gly Ser Gly
1               5                   10                  15

Gly Gly Gly Ser
            20

<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

Gly Gly Gly Ser Gly
1               5
```

<210> SEQ ID NO 34
<211> LENGTH: 6
<212> TYPE: PRT
<213> ORGANISM: Artificial Sequence
<220> FEATURE:
<223> OTHER INFORMATION: Synthetic construct

<400> SEQUENCE: 34

Ser Ser Tyr Arg Trp Asn
1               5

<210> SEQ ID NO 35
<211> LENGTH: 16
<212> TYPE: PRT
<213> ORGANISM: Artificial Sequence
<220> FEATURE:
<223> OTHER INFORMATION: Synthetic construct

<400> SEQUENCE: 35

Tyr Ile Asn Ser Ala Gly Ile Ser Asn Tyr Asn Pro Ser Leu Lys Arg
1               5                   10                  15

<210> SEQ ID NO 36
<211> LENGTH: 11
<212> TYPE: PRT
<213> ORGANISM: Artificial Sequence
<220> FEATURE:
<223> OTHER INFORMATION: Synthetic construct

<400> SEQUENCE: 36

Ser Asp Asn Met Gly Thr Thr Pro Phe Thr Tyr
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic construct

<400> SEQUENCE: 37

Arg Ser Ser Lys Ser Leu Leu Tyr Ser Asp Gly Lys Thr Tyr Leu Asn
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: Synthetic construct

<400> SEQUENCE: 38

Trp Met Ser Thr Arg Ala Ser
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic construct

<400> SEQUENCE: 39

Gln Gln Gly Leu Glu Phe Pro Thr
1               5

```
<210> SEQ ID NO 40
<211> LENGTH: 20
<212> TYPE: PRT
<213> ORGANISM: Artificial Sequence
<220> FEATURE:
<223> OTHER INFORMATION: Synthetic construct

<400> SEQUENCE: 40

Gly Gly Gly Ser Gly Gly Gly Ser Gly Gly Gly Ser Gly Gly
1               5                   10                  15

Gly Gly Ser Gly
            20

<210> SEQ ID NO 41
<211> LENGTH: 8
<212> TYPE: PRT
<213> ORGANISM: Artificial Sequence
<220> FEATURE:
<223> OTHER INFORMATION: Synthetic construct

<400> SEQUENCE: 41

Ser Ile Ile Asn Phe Glu Lys Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

Lys Val Pro Arg Asn Gln Asp Trp Leu
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic construct

<400> SEQUENCE: 43

Thr Trp His Arg Tyr His Leu Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic construct

<400> SEQUENCE: 44

Ser Val Tyr Asp Phe Phe Val Trp Leu
1               5

<210> SEQ ID NO 45
<211> LENGTH: 120
<212> TYPE: PRT
<213> ORGANISM: Artificial Sequence
<220> FEATURE:
<223> OTHER INFORMATION: Synthetic construct

<400> SEQUENCE: 45

Glu Val Gln Leu Gln Glu Ser Gly Pro Gly Leu Val Lys Pro Ser Gln
```

-continued

```
               1               5                  10                 15
          Ser Leu Ser Leu Thr Cys Ser Val Thr Gly Tyr Ser Ile Thr Ser Ser
                          20                 25                 30

Tyr Arg Trp Asn Trp Ile Arg Lys Phe Pro Gly Asn Cys Leu Glu Trp
                          35                 40                 45

Met Gly Tyr Ile Asn Ser Ala Gly Ile Ser Asn Tyr Asn Pro Ser Leu
                 50                 55                 60

Lys Arg Arg Ile Ser Ile Thr Arg Asp Thr Ser Lys Asn Gln Phe Phe
           65                 70                 75                 80

Leu Gln Val Asn Ser Val Thr Thr Glu Asp Ala Ala Thr Tyr Tyr Cys
                          85                 90                 95

Ala Arg Ser Asp Asn Met Gly Thr Thr Pro Phe Thr Tyr Trp Gly Gln
                         100                105                110

Gly Thr Leu Val Thr Val Ser Ser
                         115                120
```

```
<210> SEQ ID NO 46
<211> LENGTH: 111
<212> TYPE: PRT
<213> ORGANISM: Artificial Sequence
<220> FEATURE:
<223> OTHER INFORMATION: Synthetic construct

<400> SEQUENCE: 46

Asp Ile Val Met Thr Gln Gly Thr Leu Pro Asn Pro Val Pro Ser Gly
 1               5                  10                 15

Glu Ser Val Ser Ile Thr Cys Arg Ser Ser Lys Ser Leu Leu Tyr Ser
                20                 25                 30

Asp Gly Lys Thr Tyr Leu Asn Trp Tyr Leu Gln Arg Pro Gly Gln Ser
            35                 40                 45

Pro Gln Leu Leu Ile Tyr Trp Met Ser Thr Arg Ala Ser Gly Val Ser
         50                 55                 60

Asp Arg Phe Ser Gly Ser Gly Ser Gly Thr Asp Phe Thr Leu Lys Ile
 65                 70                 75                 80

Ser Gly Val Glu Ala Glu Asp Val Gly Ile Tyr Tyr Cys Gln Gln Gly
                85                 90                 95

Leu Glu Phe Pro Thr Phe Gly Cys Gly Thr Lys Leu Glu Leu Lys
            100                105                110
```

```
<210> SEQ ID NO 47
<211> LENGTH: 8
<212> TYPE: PRT
<213> ORGANISM: Artificial Sequence
<220> FEATURE:
<223> OTHER INFORMATION: Synthetic construct

<400> SEQUENCE: 47

Cys Gly Cys Gly Cys Gly Cys Gly
 1               5
```

IMMUNE TOLERANT ELASTIN-LIKE PEPTIDE TETRAMER GUIDED NANOPARTICLES AND METHODS OF USE

CROSS REFERENCE TO RELATED APPLICATIONS

This application claims the benefit of U.S. Provisional Applications Nos. 62/568,949, and 62/568,880 filed Oct. 6, 2017. The content of these earlier filed applications is hereby incorporated by reference herein in their entirety.

INCORPORATION OF THE SEQUENCE LISTING

The present application contains a sequence listing that is submitted via EFS-Web herewith, containing the file name "21101_0350U2 Sequenc_Listing.txt" which is 28,672 bytes in size, created on Dec. 18, 2020, and is herein incorporated by reference in its entirety.

BACKGROUND

Cancer immune checkpoint therapy has achieved remarkable clinical successes in various cancers. Current immune checkpoint inhibitors, however, block the checkpoint of the immune cells that are important to cancer therapy as well as the immune cells that are irrelevant to the therapy. Such indiscriminate blockade limits efficacy and causes autoimmune toxicity of the therapy. A therapeutic approach that uses a carrier to target immune checkpoint inhibitors to cancer-reactive immune cells is needed.

SUMMARY

Disclosed herein are nanoparticles comprising: a) one or more immune-tolerant elastin-like polypeptide (iTEP)-tetramers, wherein the one or more iTEP-tetramers comprise in amino terminal-to-carboxy terminal order (i) four MHC class I monomers, (ii) a first iTEP sequence, (iii) a second iTEP sequence and (iv) a cysteine containing tag; and b) one or more iTEP-fusion molecules, wherein the one or more iTEP-fusion molecules comprise (i) a HisTag; (ii) a linker; (iii) therapeutic agent; (iv) a first iTEP sequence; (v) a second iTEP sequence and (vi) a cysteine containing tag.

Disclosed herein are methods of making immune immune-tolerant elastin-like polypeptide (iTEP)-tetramers, the methods comprising: mixing one or more iTEP fusion peptides with four or more biotinylated MHC class I monomers, wherein the one or more iTEP fusion peptides comprise in amino terminal-to-carboxy terminal order a (i) a HisTag; (ii) a linker; (iii) four or more streptavidin moieties, (iv) a first iTEP sequence, (v) a second iTEP sequence and (vii) a cysteine containing tag under conditions to allow four or more biotinylated MHC class I monomers to bind to the four or more streptavidin moieties of the iTEP fusion peptide, wherein the binding of the four or more biotinylated MHC class I monomers to the four or more streptavidin moieties of the iTEP fusion peptide results in an iTEP-tetramer.

Disclosed herein are methods of making nanoparticles, the methods comprising:
a) mixing one or more immune-tolerant elastin-like polypeptide (iTEP) fusion peptides with four or more biotinylated MHC class I monomers, wherein the one or more iTEP fusion peptides comprise in amino terminal-to-carboxy terminal order a (i) a HisTag; (ii) a linker; (iii) four or more streptavidin moieties, (iv) a first iTEP sequence, (v) a second iTEP sequence and (vii) a cysteine containing tag under conditions to allow four or more biotinylated MHC class I monomers to bind to the four or more streptavidin moieties of the iTEP fusion peptide, wherein the binding of the four or more biotinylated MHC class I monomers to the four or more streptavidin moieties of the iTEP fusion peptide results in an iTEP-tetramer; b) mixing the iTEP-tetramer with an iTEP-fusion molecule, wherein the iTEP-fusion molecule comprises (i) a HisTag; (ii) a linker; (iii) single chain variable fragment (scFv); (iv) a first iTEP sequence; (v) a second iTEP sequence and (vi) a cysteine containing tag, wherein the iTEP-tetramer and iTEP-fusion molecule are mixed at a ratio of 10:1; and wherein the cysteine containing tag in a) and the cysteine containing tag in b) are crosslinked via one or more disulfide bonds; and c) oxidizing the one or more disulfide bonds between the iTEP-tetramer and iTEP-fusion molecule, thereby forming a stable nanoparticle.

Disclosed herein are kits comprising: a) one or more immune-tolerant elastin-like polypeptide (iTEP)-tetramers, wherein the one or more iTEP-tetramers comprise in amino terminal-to-carboxy terminal order (i) four MHC class I monomers, (ii) a first iTEP sequence, (iii) a second iTEP sequence and (iv) a cysteine containing tag; and b) one or more iTEP-fusion molecules, wherein the one or more iTEP-fusion molecules comprise in amino terminal-to-carboxy terminal order (i) a HisTag; (ii) a linker; (iii) single chain variable fragment (scFv); (iv) a first iTEP sequence; (v) a second iTEP sequence and (vi) a cysteine containing tag.

BRIEF DESCRIPTION OF THE DRAWINGS

The accompanying figures, which are incorporated in and constitute a part of this specification, illustrate several aspects and together with the description serve to explain the principles of the invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

FIG. 1A shows the sequence design of αPD-1-iTEP fusion. FIG. 1B shows an agarose gel image of DNA digestion products from three plasmids, pET-25b(+) with the scFv coding gene (lane 1), pET-25b(+) with the iTEP coding gene (lane 2), and pET-25b(+) with the fusion coding gene (lane 3). FIG. 1C is a photograph of an SDS-PAGE gel that contains intact αPD-1 (lane 1), αPD-1-iTEP fusion (lane 2), and αPD-1 sc-FV (lane 3). Twenty μg of each protein was loaded onto each lane.

FIG. 3A shows the DLS spectra of intact αPD-1 (blue), the αPD-1-iTEP fusion after NP assembly (green), and the amphiphilic iTEP after NP assembly (black). FIG. 3B shows direct binding of αPD-1 scFv, the soluble αPD-1-iTEP fusion, αPD-1 NP, and intact αPD-1 to EL4 cells. FIG. 3C shows that the PD-L1 binding to EL4 cells is blocked. In both B and C, the x-axis labels are αPD-1 equivalent concentrations in each sample.

FIGS. 4A-B show that αPD-1-iTEP fusion is functional in vivo. FIG. 4A shows that blood glucose concentrations of all mice treated with intact αPD-1, the soluble αPD-1-iTEP fusion, and αPD-1 NP. Each line represents glucose concentration changes of one mouse. Data of PBS-treated mice were not included for the simplicity of the figure. In addition, none of PBS-treated mice showed glucose levels higher than 250 mg/dL, a threshold level of diabetes (red dash line), during the observation period. FIG. 4B shows the diabetes-free survival of the mice that received PBS, intact αPD-1, the soluble fusion, and αPD-1 NP. Red arrows indicate the date of treatments.

FIG. 5 shows that the tetramer-guided αPD-1 NP preferentially delivers αPD-1 to tumor-reactive CTLs such as melanoma-reactive CTLs because it has a higher avidity to the CTLs than to all other PD-1 positive cells.

Figure 6:
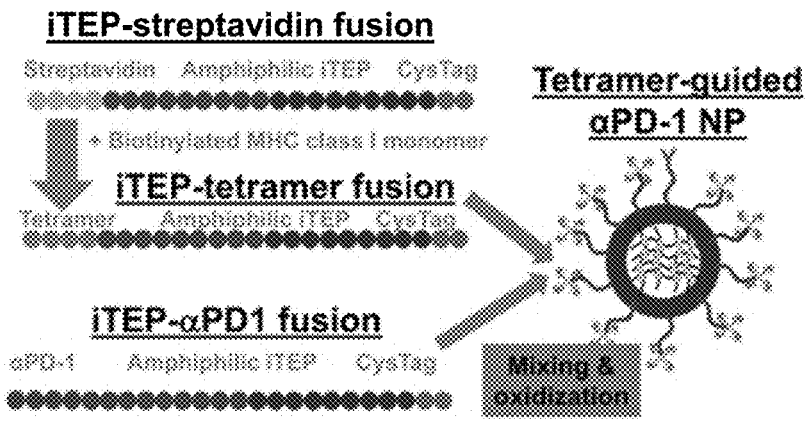

FIG. 6 shows the tetramer-guided αPD-1 NP can be assembled from two fusions and stabilized by disulfide bonds.

Figure 7A:
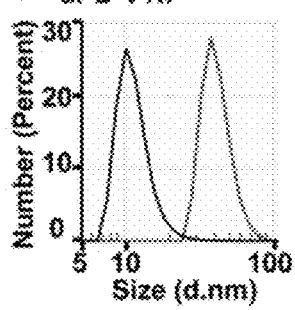
Figure 7B:
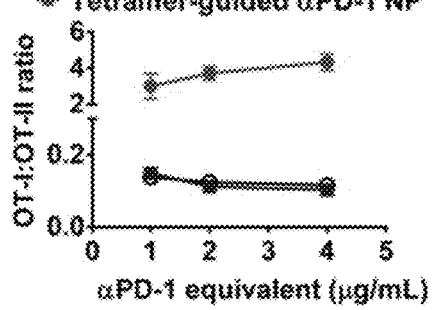
Figure 7C:
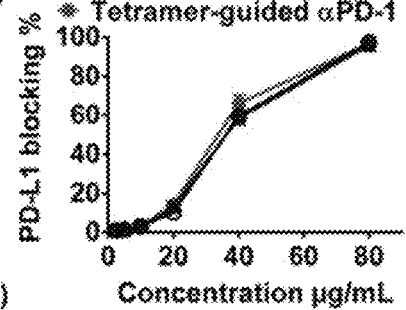

FIGS. 7A-C shows results using the tetramer-guided αPD-1 NP. FIG. 7A illustrates the results of the DLS analysis showing that guided αPD-1 NPs are 42.6±9.6 nm in size while free αPD-1 is 11.6±3.4 nm. FIG. 7B shows that after labeling, the guided αPD-1 NP was incubated with an OT-POT-II T cell mixture (ratio 1:1), the NP labeled more OT-I T cells (cognate to the tetramer) than OT-II T cells (non-cognate, PD-1 positive cells) at the tested concentrations. FIG. 7C shows that αPD-1 on the guided NP blocked the binding of PD-1 ligand 1 (PD-L1) to PD-1-positive cells as effectively as free αPD-1 or unguided αPD-1 NP. The data suggested that the NP structure did not interfere the binding capacity of αPD-1.

Figure 8:
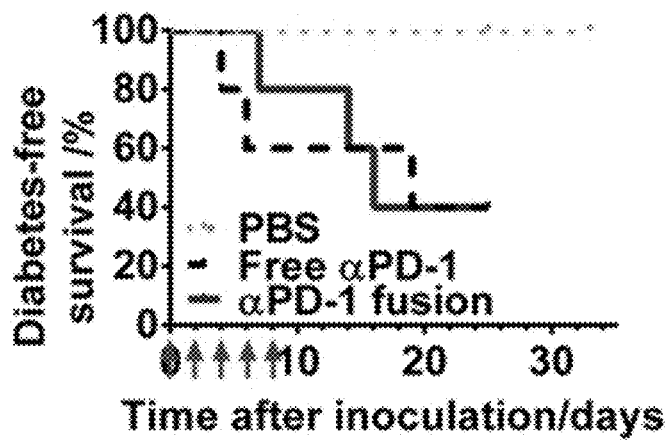

FIG. 8 shows that the αPD-1-iTEP fusion accelerated diabetes occurrence in NOD mice as effectively as free αPD-1 as evidenced by similar diabetes-free survival curves. The arrows point to dosing days (N=5). The data suggested that αPD-1 on the NP is functional.

Figure 9:
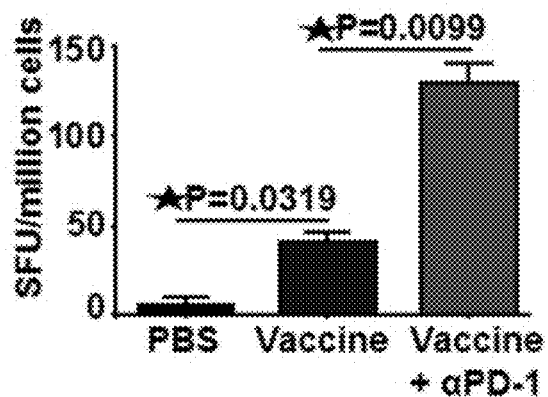

FIG. 9 shows that mice with B16 tumors were vaccinated with Trp-2 peptide vaccines. Some mice were further treated with free αPD-1 (200 ug/mouse).

Figure 10:
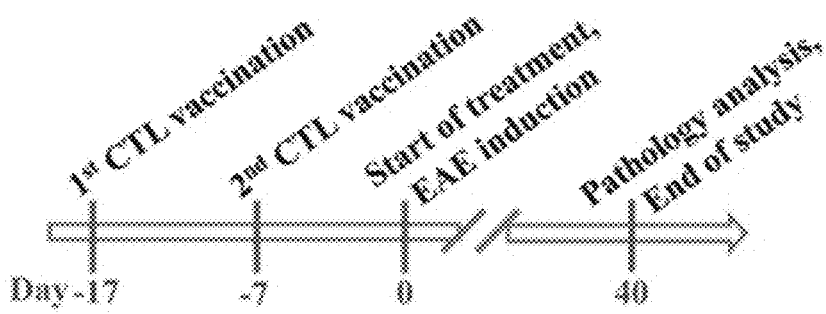

FIG. 10 shows the timeline of the toxicity evaluation.

Figure 11:
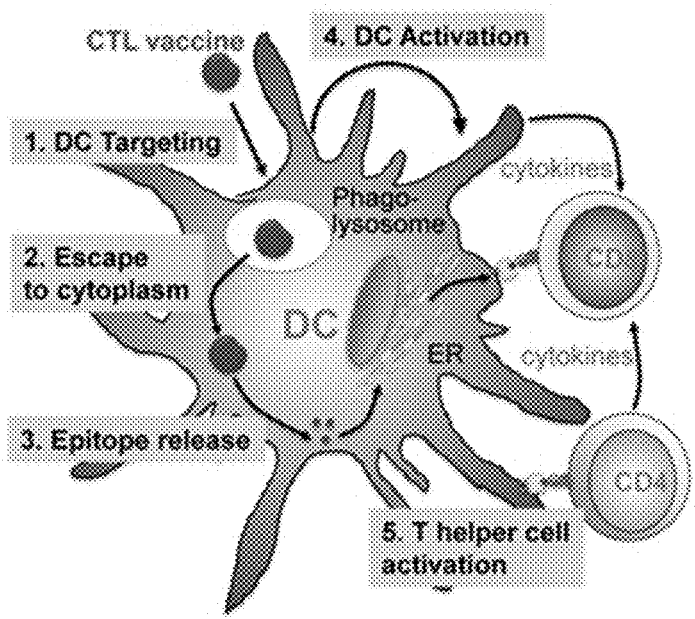

FIG. 11 is a schematic illustration of barriers of CTL vaccines.

Figure 12:
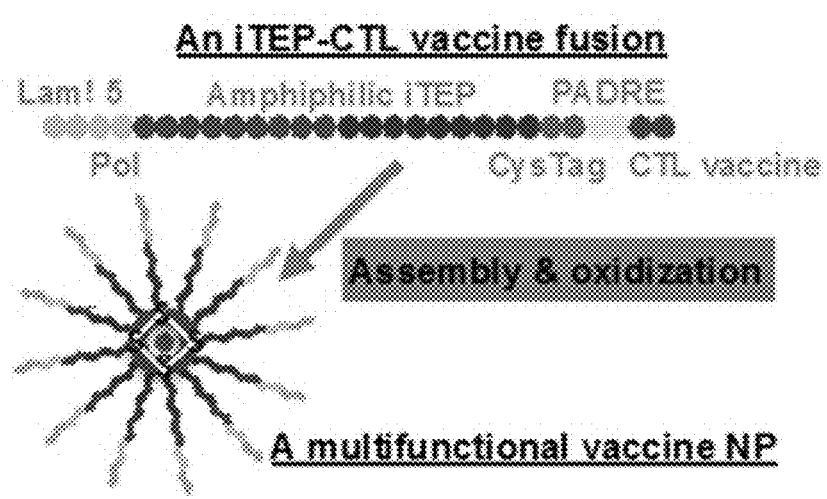

FIG. 12 is a schematic illustration showing the multifunctional vaccine NP that is assembled from a single vaccine fusion polypeptide and stabilized by disulfide bonds.

FIG. 13 shows that Lamα5-iTEP (15 μM) activates DCs as effectively as LPS (10 ng, positive control) evidenced by TNF-α secretion from the treated DCs (N=3).

FIGS. 14A-D show the results of experiments using vaccine NPs. FIG. 14A shows the DLS results of assembled vaccine NPs. FIG. 14B shows the subcellular distribution of the vaccine NPs and their controls in DC2.4 cells after the cells were incubated with 5 μM of the samples for 2 h. FIGS. 14C-D show DC2.4 cells treated with the vaccine NPs and their controls for 20 h. FIG. 14C shows that the culture media of DCs were assayed for TNF-α and IL-6 (unshown) as activation markers by ELISA. FIG. 14D shows the cells were analyzed for CD40 and CD80 (unshown) expression as maturation markers.

Figure 15:
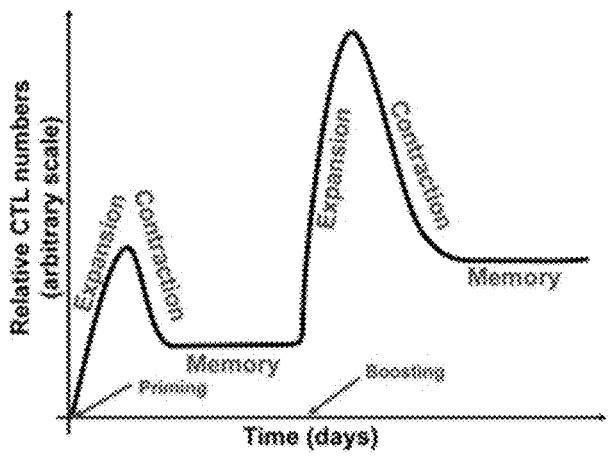

FIG. 15 shows the typical kinetics of CTL responses after two vaccinations.

Figure 16:
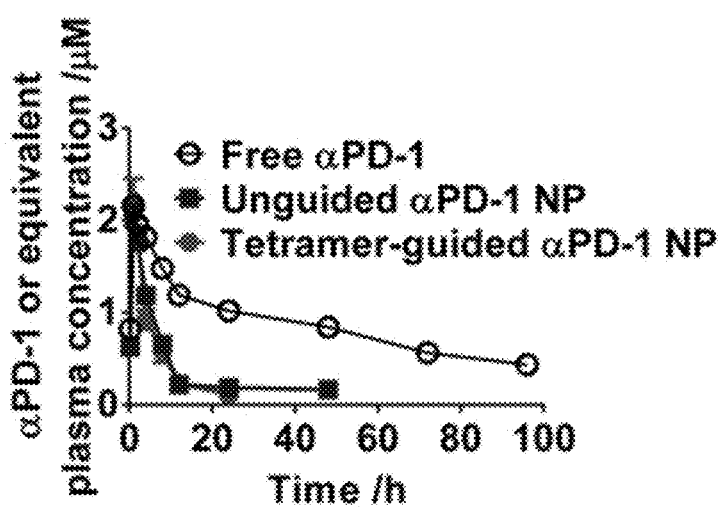

FIG. 16 shows the plasma αPD-1 changes after αPD-1 was administered intraperitoneally as free form, on unguided NPs, and guided NPs.

Figure 17:
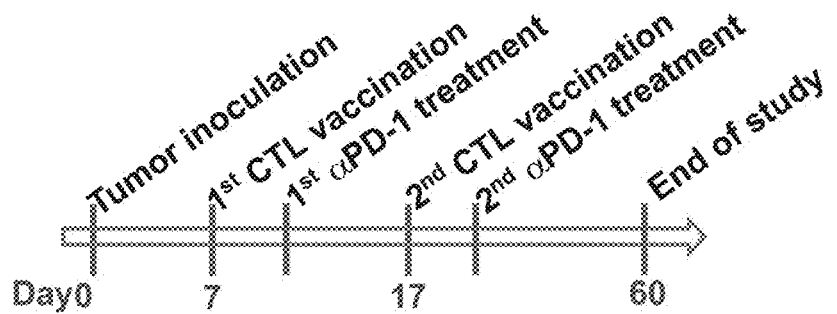

FIG. 17 shows the timeline of procedures described herein.

FIG. 18 is a schematic of tetramer-guided αCTLA-4 NPs having greater avidity to melanoma-reactive CTLs with cognate T cell receptors (TCRs) than cells without cognate TCRs, a difference that enables the NPs to target αCTLA-4 to the CTLs.

FIG. 19 is a schematic showing the process to assemble the NP.

DETAILED DESCRIPTION

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect.

It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "comprising" can include the aspects "consisting of" and "consisting essentially of."

As used herein, the term "iTEP" refers to an immune-tolerant, elastin-like polypeptide differing from previously disclosed elastin-like polypeptides (referred to as ELPs) as they have the phase transition property and are immune-tolerant.

Immune checkpoint inhibitors such as the anti-cytotoxic T lymphocyte antigen-4 antibody ($\alpha$CTLA-4) and the anti-programmed death-1 antibody ($\alpha$PD-1) have been approved to treat advanced melanoma, lung cancer, head and neck cancer, among others (Michielin, O., et al., Gaining momentum: New options and opportunities for the treatment of advanced $\alpha$. *Cancer Treat Rev* 2015, 41 (8), 660-70; Wolchok, J. D., et al., Nivolumab plus ipilimumab in advanced melanoma. *The New England Journal of Medicine* 2013, 369 (2), 122-33; Administration, U. S. F. a. D. pembrolizumab (KEYTRUDA). www.accessdata.fda.gov/drugsatfda_docs/label/2016/125514s009lbl.pdf; and Sharma, P., et al., Immune checkpoint targeting in cancer therapy: toward combination strategies with curative potential. *Cell* 2015, 161 (2), 205-14; and Larkin, J., et al., Combined Nivolumab and Ipilimumab or Monotherapy in Untreated Melanoma. *The New England Journal of Medicine* 2015). Some of these inhibitors have been approved by the FDA, such as Pembrolizumab and Nivolumab (Swaika, A., et al., Current state of anti-PD-L1 and anti-PD-1 agents in cancer therapy. *Molecular Immunology* 2015, 67 (2, Part A), 4-17). Recently, $\alpha$CTLA-4 and $\alpha$PD-1 were combined to further boost their efficacy (Wolchok, J. D., et al., Nivolumab plus ipilimumab in advanced melanoma. *The New England Journal of Medicine* 2013, 369 (2), 122-33; and Larkin, J., et al., Combined Nivolumab and Ipilimumab or Monotherapy in Untreated Melanoma. *The New England Journal of Medicine* 2015). However, the further improvement of the immune checkpoint therapy is hindered by its autoimmune toxicity. For example, in the above combination therapy, 55% of the combination therapy patients suffered from high-grade (grades 3-4) toxicity, and 36% of the patients had to discontinue the therapy due to the toxicity (Larkin, J., et al., Combined Nivolumab and Ipilimumab or Monotherapy in Untreated Melanoma. *The New England Journal of Medicine* 2015). In contrast to the pressing need to reduce the toxicity, the current toxicity mitigating method, non-specific immune suppression, is apparently not effective enough because one third of the treated patients had to stop the therapy even after using this method, not to mention that the method has its own side effects (e.g., immune deficiency) (Tarhini, A., Immune-mediated adverse events associated with ipilimumab ctla-4 blockade therapy: the underlying mechanisms and clinical management. *Scientifica* (Cairo) 2013, 2013, 857519). Previously, intra-tumor injection of the inhibitors was attempted and proven effective (Fransen, M. F., et al., Controlled local delivery of CTLA-4 blocking antibody induces CD8+T-cell-dependent tumor eradication and decreases risk of toxic side effects. *Clinical Cancer Research: an Official Journal of the American Association for Cancer Research* 2013, 19 (19), 5381-9); however, this method is not practical for advanced cancer patients as it is almost impossible to inject inhibitors into metastatic tumors. Therefore, new strategies are needed to reduce the toxicity of immune checkpoint inhibitors.

Intrinsically, immune checkpoints (e.g., PD-1 and CTLA-4) protect tumors from immune elimination (Topalian, S. L., et al., Targeting the PD-1/B7-H1 (PD-L1) pathway to activate anti-tumor immunity. *Current Opinion in Immunology* 2012, 24 (2), 207-212; and Baksh, K., et al., Immune checkpoint protein inhibition for cancer: preclinical justification for CTLA-4 and PD-1 blockade and new combinations. *Semin Oncol* 2015, 42 (3), 363-77), and also prevent autoimmune toxicity in healthy tissues (Pentcheva-Hoang, T., et al., Negative regulators of T-cell activation: potential targets for therapeutic intervention in cancer, autoimmune disease, and persistent infections. *Immunological reviews* 2009, 229 (1), 67-87). The cause of the toxicity is that the checkpoint inhibitors indiscriminately block the checkpoint in all cells that utilize the checkpoints (Pentcheva-Hoang, T., et al., Negative regulators of T-cell activation: potential targets for therapeutic intervention in cancer, autoimmune disease, and persistent infections. *Immunological reviews* 2009, 229 (1), 67-87; Gelao, L., et al., Immune checkpoint blockade in cancer treatment: a double-edged sword cross-targeting the host as an "innocent bystander". *Toxins* 2014, 6 (3), 914-33; Nishino, M., et al., Anti-PD-1-Related Pneumonitis during Cancer Immunotherapy. *New England Journal of Medicine* 2015, 373 (3), 288-290; Kochupurakkal, N. M., et al., Blockade of the programmed death-1 (PD1) pathway undermines potent genetic protection from type 1 diabetes. *PloS one* 2014, 9 (2), e89561; Frebel, H., et al., The risks of targeting co-inhibitory pathways to modulate pathogen-directed T cell responses. *Trends in immunology* 2013, 34 (5), 193-9; and Read, S., et al., Blockade of CTLA-4 on CD4+CD25+ regulatory T cells abrogates their function in vivo. *Journal of immunology* 2006, 177 (7), 4376-83). Thus, to resolve the toxicity of the inhibitors, it is desirable to target the inhibitors to those cells that are important for tumor treatment but also suppressed by the checkpoint. Such targeting also has the potential to boost the efficacy of the inhibitors because it concentrates the inhibitors to those cells targeted for cancer therapy, whereas the current non-specific blockade wastes inhibitors in tumor treatment-unrelated interactions. Recently, a platelet-based carrier was used to target an immune checkpoint inhibitor, anti-PD-L1 antibody, to tumors, which resulted in better prevention of tumor recurrence under a post-surgery setting (Wang, C., et al., In situ activation of platelets with checkpoint inhibitors for post-surgical cancer immunotherapy. *Nature Biomedical Engineering* 2017, 1, 0011). However, it is unclear whether the carrier reduced the toxicity of the immune checkpoint inhibitors. Thus, drug carriers that can target immune checkpoint inhibitors and reduce their toxicity are needed.

Patients with advanced melanoma suffered a five-year survival rate of 16.6% due to the lack of an effective therapy (Howlader N, et al. SEER Cancer Statistics Review, 1975-2012. National Cancer Institute, 2015). Among the new therapies developed, the αPD-1 therapy has achieved lasting responses in some patients (Brahmer JR, et al. Safety and activity of anti-PD-L1 antibody in patients with advanced cancer. The New England Journal of Medicine. 2012; 366 (26):2455-65; Hamid O, et al. Safety and tumor responses with lambrolizumab (anti-PD-1) in melanoma. The New England Journal of Medicine. 2013; 369(2):134-44; and Herbst RS, et al. Predictive correlates of response to the anti-PD-L1 antibody MPDL3280A in cancer patients. Nature. 2014; 515(7528):563-7). Two αPD-1s, Keytruda® and Opdivo®, have been approved for treating advanced melanoma; however, deficiencies exist in the current αPD-1 therapy. Among melanoma patients who were selected for αPD-1 clinical trials, response rates were less than 50% (Brahmer JR, et al. Safety and activity of anti-PD-L1 antibody in patients with advanced cancer. The New England Journal of Medicine. 2012; 366(26):2455-65; Hamid O, et al. Safety and tumor responses with lambrolizumab (anti-PD-1) in melanoma. The New England Journal of Medicine. 2013; 369(2):134-44; and Herbst RS, et al. Predictive correlates of response to the anti-PD-L1 antibody MPDL3280A in cancer patients. Nature. 2014; 515(7528):563-7). Among the treated patients, 15% of them reported high grade (grades 3-4) treatment-related toxicity (Larkin J, et al. Combined Nivolumab and Ipilimumab or Monotherapy in Untreated Melanoma. The New England Journal of Medicine. 2015; and Topalian SL, et al. Safety, activity, and immune correlates of anti-PD-1 antibody in cancer. The New England Journal of Medicine. 2012; 366(26):2443-54), and 5-7% of them had to discontinue the treatment because they were never able to recover from the toxicity (Larkin J, et al. Combined Nivolumab and Ipilimumab or Monotherapy in Untreated Melanoma. The New England Journal of Medicine. 2015; and Topalian SL, et al. Safety, activity, and immune correlates of anti-PD-1 antibody in cancer. The New England Journal of Medicine. 2012; 366(26):2443-54). Even more alarming is that 4% of treated patients died from the toxicity (Topalian SL, et al. Safety, activity, and immune correlates of anti-PD-1 antibody in cancer. The New England Journal of Medicine. 2012; 366(26):2443-54). These numbers highlight the importance of reducing the toxicity of αPD-1 therapy and reveal the ineffectiveness of current αPD-1 toxicity mitigation methods. Furthermore, the current mitigation methods, primarily non-specific immune suppression, exposed the treated patients to immune deficiency and serious infections (Tarhini A. Immune-mediated adverse events associated with ipilimumab ctla-4 blockade therapy: the underlying mechanisms and clinical management. Scientifica (Cairo). 2013; 2013:857519). Patients with autoimmune disorders and chronic infections were excluded from αPD-1 clinical trials because they are sensitive to the αPD-1 toxicity (Robbins PF, et al. Mining exomic sequencing data to identify mutated antigens recognized by adoptively transferred tumor-reactive T cells. Nature medicine. 2013; 19(6):747-52). Although the exact exclusion rates were never published, records at the University of Utah Hospital show that 5% melanoma patients reported autoimmune disorders (unpublished data). In addition, the fact that ~50 million Americans have autoimmune disorders hints at the possible scope of the exclusion (American Autoimmune Related Diseases Association I. Autoimmune Statistics 2015. Available from: www.aarda.org/autoimmune-information/autoimmune-statistics/). Furthermore, the exclusion may miss those patients who could respond to the therapy better than other patients. For example, melanoma patients with vitiligo, an autoimmune disorder, actually respond better to immunotherapy (Uchi H, S et al. Unraveling the complex relationship between cancer immunity and autoimmunity: lessons from melanoma and vitiligo. Advances in immunology. 2006; 90:215-41). These deficiencies can be attributed to, for example, the indiscriminate PD-1 blockade of the current therapy. To resolve these deficiencies, a targeted anti-PD-1 antibody (αPD-1) therapy that enacts a cell-specific PD-1 blockade was developed and described herein.

Immune checkpoint inhibitors are able to block the immune checkpoint of anti-cancer T cells and boost anti-cancer immunity. However, the blockade conferred by these inhibitors is not specific. These inhibitors block the checkpoint of anti-cancer T cells and the checkpoint of other T cells that should otherwise be suppressed to maintain immune stasis. Consequently, the undesired blockade leads to autoimmune toxicity or worsen conditions in those cancer patients with autoimmune disorders. The toxicity limits the application broadness and duration of these inhibitors. Disclosed herein are compositions and methods that permit specific blockade and therefore may reduce the toxicity associated with the use and administration of these inhibitors.

Herein, methods to load therapeutic inhibitors into carriers are described. In some aspects, the anti-programmed death-1 antibody (αPD-1) was used as a model immune checkpoint inhibitor. Some of the Examples describe the generation of a recombinant single-chain variable fragment (scFv) of αPD-1 (and α-CTLA-4) and the design and production of fusion proteins comprising the scFv and an amphiphilic immune-tolerant elastin-like polypeptide (iTEP). In some aspects, because the iTEP is amphiphilic, the fusion is able to self-assemble into a nanoparticle (NP). The NP was proved to block the PD-1 immune checkpoint in vitro and in vivo. Particularly, the NP exacerbated diabetes development in non-obese diabetic mice as effectively as natural, intact αPD-1. In summary, αPD-1 was successfully expressed as a recombinant protein and linked αPD-1 to a NP, which lays a foundation to develop a delivery system to target αPD-1 to a subpopulation of immune cells.

Disclosed herein are new αPD-1 therapies that may resolve current deficiencies of existing PD-1 therapy. The new therapies will benefit a broader patient population and achieve even higher response rates than the current PD-1 therapy.

Also described herein are MHC Class I tetramer-guided PD-1 (and CTLA-4) nanoparticles and paired vaccine nanoparticles that can be used as an alternative to existing PD-1 (and CTLA-4) therapies.

Disclosed herein are nanoparticles that serve as a carrier for the delivery of therapeutic agents, for example, immune checkpoint inhibitors, αPD-1 (and αCTLA-4). Different from the previously reported carriers of these inhibitors (Bae Y, et al. Intelligent polymeric micelles from functional poly(ethylene glycol)-poly(amino acid) block copolymers. Advanced Drug Delivery Reviews. 2009; 61(10):768-84), αPD-1 and its carrier molecule, iTEP (American Autoimmune Related Diseases Association I. Autoimmune Statistics 2015. Available from: www.aarda.org/autoimmune-information/autoimmune-statistics/; Tarhini A. Immune-mediated adverse events associated with ipilimumab ctla-4 blockade therapy: the underlying mechanisms and clinical management. Scientifica (Cairo). 2013; 2013:857519; and Uchi H, S et al. Unraveling the complex relationship between cancer immunity and autoimmunity: lessons from melanoma and vitiligo. Advances in immunology. 2006; 90:215-41), are generated together as a recombinant fusion polypeptide. As disclosed herein, the fusion polypeptide can self-assemble into a nanoparticle (NP). This NP can effectively block, for example, the PD-1 immune checkpoint in vitro and in vivo. Further disclosed herein are NPs that can be integrated with cell targeting moieties so that the NP can bind with tumor-reactive immune cells. Thus, the NP can target, for example, αPD-1, as well as other inhibitors, to these cells. Disclosed herein are cell-targeting carriers for immune checkpoint inhibitors.

Also disclosed herein are MHC class I tetramer-guided αCTLA-4 nanoparticles (NP) (FIG. 18) that have reduced toxicity. As an approved medication to treat advanced melanoma, αCTLA-4 significantly extended the survival time of melanoma patients as a part of a combination therapy (Michielin, O., et al., Gaining momentum: New options and opportunities for the treatment of advanced α. Cancer Treat Rev 2015, 41 (8), 660-70). However, αCTLA-4 also tripled the likelihood of severe treatment-related adverse effects among these patients (Michielin, O., et al., Gaining momentum: New options and opportunities for the treatment of advanced α. Cancer Treat Rev 2015, 41 (8), 660-70), 36% of the patients experiencing the adverse effects had to discontinue use of αCTLA-4 (Michielin, O., et al., Gaining momentum: New options and opportunities for the treatment of advanced α. Cancer Treat Rev 2015, 41 (8), 660-70); and some of the adverse effects are even lethal (Wolchok, J. D., et al Nivolumab plus ipilimumab in advanced melanoma. The New England Journal of Medicine 2013, 369 (2), 122-33). Currently, the toxicity is managed using nonspecific immune suppression which has its own side effects (Administration, U. S. F. a. D. pembrolizumab (KEYTRUDA). www.accessdata.fda.gov/drugsatfda_docs/label/2016/125514s009lbl.pdf). More importantly, the suppression is not effective enough to resolve the adverse effects as some patients never recovered from the adverse events even after applying the suppression (Wolchok, J. D., et al., Nivolumab plus ipilimumab in advanced melanoma. The New England Journal of Medicine 2013, 369 (2), 122-33; and Sharma, P., et al., Immune checkpoint targeting in cancer therapy: toward combination strategies with curative potential. Cell 2015, 161 (2), 205-14). A new strategy, intra-melanoma injection of αCTLA-4, was shown to reduce the toxicity (Larkin, J., et al., Combined Nivolumab and Ipilimumab or Monotherapy in Untreated Melanoma. The New England Journal of Medicine 2015). However, advanced melanoma has liver, brain, and lung metastasis and is not suitable for direct injection. Thus, there is a pressing need to develop a safe and effective strategy to reduce this toxicity.

Targeting αCTLA-4 to melanoma-reactive cytotoxic T lymphocytes (CTLs) could reduce the toxicity of αCTLA-4. The cause of the toxicity is that αCTLA-4 indiscriminately activates all CTLA-4-positive cells. While the activation of some CTLA-4-positive cells, particularly melanoma-reactive CTLs, is important for the therapy (Larkin, J., et al., Combined Nivolumab and Ipilimumab or Monotherapy in Untreated Melanoma. The New England Journal of Medicine 2015; and Swaika, A., et al., Current state of anti-PD-L1 and anti-PD-1 agents in cancer therapy. Molecular Immunology 2015, 67 (2, Part A), 4-17), the activation of some other cells is unnecessary for the therapy and causes the toxicity. Targeting αCTLA-4 to melanoma-reactive CTLs will reduce the exposure of αCTLA-4 to those CTLA-4-positive cells that cause the toxicity and will diminish the toxicity. Meanwhile, the targeting increases exposure of αCTLA-4 to melanoma-reactive CTLs and hence can improve the efficacy of αCTLA-4.

The dual-NP approach disclosed herein is driven by the following drug delivery ideas: (1) using MHC class I tetramers to anchor αPD-1 to melanoma-reactive CTLs, (2) using the mixed-micelle approach to create a high tetramer-to-αPD-1 ratio on the NP so that the NP has a higher avidity to melanoma-reactive CTLs as compared to other PD-1 positive cells, and (3) using a multifunctional CTL vaccine NP to address barriers in CTL vaccination to activate and amplify melanoma-reactive CTLs. The NP described herein is assembled from a single polypeptide. The dual NPs based on iTEPs are designed as described herein due to the following features: (1) iTEPs are safe, biodegradable, and humorally immune tolerated; thus, carrier-specific antibody responses are not a concern (Cho S, et al. Immune-tolerant elastin-like polypeptides (iTEPs) and their application as CTL vaccine carriers. J Drug Target. 2016; 24(4):328-39); (2) through genetic engineering, the sequences, amphiphilicity, and NP-forming capacity of iTEPs can be controlled; proteins and peptide loads can be accurately fused with iTEP carriers (Cho S, et al. Immune-tolerant elastin-like polypeptides (iTEPs) and their application as CTL vaccine carriers. J Drug Target. 2016; 24(4):328-39; and Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78); and (3) iTEPs and their fusions can be reproduced consistently and purified easily by cycling their thermally-induced, reversible phase transitions.

Disclosed herein is a drug delivery technology that permits a T cell clone-specific immune checkpoint therapy. This technology allows the delivering of immune checkpoint inhibitors to target specific clones of CD8 T cells, and hence block the immune checkpoint in these T cells.

The compositions described herein are illustrated in FIGS. 5 and 18, and involve a mixed micelle-like nanoparticle (NP). On the surface of this NP, there are multiple copies of a CD8 T cell-targeting moiety, MHC class I tetramer. Also on the surface of the NP are immune checkpoint inhibitors such as αPD-1 and αCTLA-4. The copy number ratio between the tetramer and the inhibitors should be larger than 1.0. The tetramer can be CD8 T cell clone-specific; the tetramer binds with CD8 T cells that have T cell receptors cognate to the tetramer. By altering types of tetramer on the NP, the NP can be used to target different T cell receptors and consequently different clone of CD8 T cells. In this way, the NP can be used to deliver immune checkpoint inhibitors to a defined clone of CD8 T cells. In cancer therapy, specifically, the inhibitors can be delivered to cancer-reactive CD8 T cells using this technology and block the immune checkpoint of these cells. These nanoparticles are referred to herein as MHC class I tetramer-guided NP or tetramer-guided NPs.

Compositions

Nanoparticles. Disclosed herein are nanoparticles. In an aspect, the nanoparticles can comprise one or more immune-tolerant elastin-like polypeptide (iTEP)-tetramers. The nanoparticles can also comprise one or more iTEP-fusion molecules. In an aspect, the one or more iTEP-tetramers and the one or more iTEP-fusion molecules described herein can self-assemble into nanoparticles.

iTEP-tetramers. Disclosed herein are iTEP-tetramers. In an aspect, the one or more iTEP-tetramers can comprise (i) four MHC class I monomers, (ii) a first iTEP sequence, (iii) a second iTEP sequence, and (iv) a cysteine containing tag. In an aspect, the one or more iTEP-tetramers can comprise in amino terminal-to-carboxy terminal order (i) four MHC class I monomers, (ii) a first iTEP sequence, (iii) a second iTEP sequence, and (iv) a cysteine containing tag.

MHC class I monomers.Disclosed herein are major histocompatibility complex (MHC) class 1 monomers. The MHC class I monomers can be biotinylated. Four MHC class I monomers can form a MHC tetramer. In an aspect, the four or more biotinylated MHC class I monomers can be H2-$D^b$/gp100 epitope, H2-$K^b$/TRP-1 epitope, H2-$K^b$/TRP-2 epitope, or the other complexes of MHC class I/tumor-associated epitopes. Each of the four or more biotinylated MHC class I monomers can be the same. In other words, for each tetramer, the same MHC class I/tumor-associated epitopes or MHC class I monomers can be used. The tetravalent structure can be produced by biotinylating soluble MHC class I monomers. In some aspects, each nanoparticle would also have the same tetramer (e.g., same MHC class I/tumor-associated epitopes or MHC class I monomers). In some aspects, each nanoparticle can also have one or more tetramers such that the MHC class I/tumor-associated epitopes or MEW class I monomers differ. Thus, a nanoparticle can have a combination of biotinylated MHC class I monomers as long as the biotinylated MHC class I monomers are the same for each tetramer.

iTEP sequences. The iTEP sequences described herein can be used to form tetramers (e.g. iTEP-tetramers). The iTEP sequences described herein can also be a part of an iTEP-fusion molecule. In an aspect, the first iTEP sequence comprises amino acid sequence $(Gly-Ala-Gly-Val-Pro-Gly)_{70}$ (SEQ ID NO: 20) or $(Gly-Val-Leu-Pro-Gly-Val-Gly)_{56}$ (SEQ ID NO: 21). In an aspect, the second iTEP sequence comprises amino acid sequence $(Gly-Ala-Gly-Val-Pro-Gly)_{70}$ (SEQ ID NO: 20) or $(Gly-Val-Leu-Pro-Gly-Val-Gly)_{56}$ (SEQ ID NO: 21). In an aspect, the first and second iTEP sequences can be different. iTEP sequences can be hydrophilic or hydrophobic. In an aspect, the first iTEP sequence can be hydrophilic and the second iTEP sequence can be hydrophobic. In an aspect, the first iTEP sequence can be hydrophobic and the second iTEP sequence can be hydrophilic. The first and second iTEP sequences can be joined to form an amphiphilic diblock co-polypeptide. The first and second iTEP sequences can be selected such that one sequence is hydrophilic and the other sequence is hydrophobic, forming an amphiphilic diblock molecule. Determining the hydrophobicity of a peptide sequence is within the ability of one of ordinary skill in the art.

As described herein, the first and second iTEP sequences can be joined to form an amphiphilic diblock co-polypeptide. As used herein, "amphiphilic diblock co-polypeptide" can also be referred to as an amphiphilic co-polypeptide, amphiphilic diblock polypeptide, recombinant polypeptide, a recombinant fusion polypeptide, a fusion polypeptide, diblock copolymers, fusion proteins or iTEP fusions and the like.

The iTEP sequences disclosed herein can comprise one or more homologous amino acid repeats. Generally, each iTEP-tetramer comprises an amphilphilic polypeptide. In an aspect, the one or more iTEP-tetramers can comprise one or more amphiphilic polypeptides. In an aspect, the one or more iTEP-fusion molecules can comprise one or more amphiphilic polypeptides. In an aspect, the amphiphilic polypeptides can be amphiphilic co-polypeptides. In an aspect, the amphiphilic polypeptides can comprise two or more homologous amino acid repeats linked together by covalent bonds. One or more cysteine residues can be inserted between the amphiphilic polypeptides and a therapeutic (e.g., a vaccine, pOVA is a vaccine). The number of cysteine residues can be 1, 2, 3, 4, 5, 10, 15, 20, or more or any number in between. In an aspect, the number of cysteine residues is four. The cysteine residues can be separated by one or more glycine residues. The number of glycine residues can vary and depend on the number of cysteine residues inserted between the amphiphilic polypeptides and pOVA. The number of glycine residues between two cycteines can be 1, 2, 3, 4, 5, 10, 15, 20, or more or any number in between. In an aspect, the number of glycine residues can be eight. For example, when four cysteine residues are inserted between the amphiphilic polypeptides and pOVA, eight glycine residues can be inserted to separate the adjacent cysteine residues. In an aspect, the fusion proteins can be amphiphilic. In some aspects, the amphiphilic polypeptides or fusion proteins can be fused with a therapeutic agent (e.g., a vaccine, pOVA).

Also described herein, are iTEP sequences comprising an amino acid sequence conforming to the formula: Val-Pro-Gly-$Xaa_1$-Gly-$Xaa_2$-Gly-Ala-Gly wherein $Xaa_1$ is Leu or Phe and $Xaa_2$ is Ala or Val (SEQ ID NOs: 16-19), wherein the amino acid sequence is repeated. The recombinant polypeptide can further comprise one or more residues positioned at the N-terminus, C-terminus, or both the N-terminus and C-terminus of the recombinant polypeptide. In an aspect, the one or more residues are glycine, alanine or serine or a combination thereof. In an aspect, the recombinant polypeptide comprises the amino acid sequence Gly-$(Val-Pro-Gly-Phe-Gly-Ala-Gly-Ala-Gly)_{21}$-Gly-Gly (SEQ ID NO: 25); or Gly-$(Val-Pro-Gly-Leu-Gly-Ala-Gly-Ala-Gly)_{96}$-Gly-Gly (SEQ ID NO: 26); or Gly-(Val-Pro-Gly-Leu-Gly-Val-Gly-Ala-gly-Gly-Gly)(SEQ ID NO: 27). In some aspects, the recombinant polypeptide comprises SEQ ID NO: 5, wherein SEQ ID NO: 5 can have one or more glycine residues at both the C-terminus and the N-terminus ends (e.g., SEQ ID NO: 27). In some aspects, SEQ ID NO: 5 can be repeated 2, 3, 4, 5, 10, 15, 20, 30, 40, 50, 100, 150, 200 or any number in between. In some aspects, the recombinant polypeptide can have the general formula: XX-$(\text{homologous amino acid repeat})_x$-XX. As described below, "XX" can be one or more glycine residues at both the C-terminus and the N-terminus ends; and "x" can be 2, 3, 4, 5, 10, 15, 20, 30, 40, 50, 100, 150, 200 or any number in between. In an aspect, the identified molecular weight of the recombinant polypeptide can be between 10 and 100 kDa.

Homologous amino acid repeat. As used herein, the term "homologous amino acid repeat" or "monomer" refers to an amino acid sequence comprising any of the 20 protein amino acids and is reiterated or duplicated linearly. The homologous amino acid repeat sequence can be repeated 2, 3, 4, 5, 10, 15, 20, 30, 40, 50, 100, 150, 200 times or more or any number of times in between. In an aspect, the homologous amino acid repeat comprises no more than 100 repeats. In another aspect, the homologous amino acid repeat comprises at least 20 repeats. In an aspect, the homologous amino acid repeat comprises at least 50 repeats. In an aspect, the homologous amino acid repeat comprises at least 70 repeats.

In an aspect, the homologous amino acid repeat can be the sequence Gly-Val-Leu-Pro-Gly-Val-Gly (SEQ ID NO: 1; iTEP$_A$); Gly-Ala-Gly-Val-Pro-Gly (SEQ ID NO: 2; iTEP$_B$); Val-Pro-Gly-Phe-Gly-Ala-Gly-Ala-Gly (SEQ ID NO: 3; iTEP$_C$); Val-Pro-Gly-Leu-Gly-Ala-Gly-Ala-Gly (SEQ ID NO: 4; iTEP$_D$); Val-Pro-Gly-Leu-Gly-Val-Gly-Ala-Gly (SEQ ID NO: 5; iTEP$_E$); Gly-Val-Leu-Pro-Gly-Val-Gly-Gly (SEQ ID NO: 6); Gly-Val-Leu-Pro-Gly (SEQ ID NO: 7); Gly-Leu-Val-Pro-Gly-Gly (SEQ ID NO: 8); Gly-Leu-Val-Pro-Gly (SEQ ID NO: 9); Gly-Val-Pro-Leu-Gly (SEQ ID NO: 10); Gly-Ile-Pro-Gly-Val-Gly (SEQ ID NO: 11); Gly-Gly-Val-Leu-Pro-Gly (SEQ ID NO: 12); Gly-Val-Leu-Pro-Gly (SEQ ID NO: 13); Gly-Val-Gly-Val-Leu-Pro-Gly (SEQ ID NO: 14); or Gly-Val-Pro-Gly (SEQ ID NO: 15). Table 1 lists homologous amino acid repeat sequences.

In an aspect, the first or second iTEP sequence can comprise a homologous amino acid repeat comprising four or more amino acid residues wherein one of the amino acid residues is proline and one or more of the amino acid residues is valine, having at least 75% amino acid sequence identity to the amino acid repeat, and wherein the amino acid repeat is: Gly-Val-Leu-Pro-Gly-Val-Gly (SEQ ID NO: 1; iTEP$_A$); Gly-Ala-Gly-Val-Pro-Gly (SEQ ID NO: 2 iTEP$_B$); Val-Pro-Gly-Phe-Gly-Ala-Gly-Ala-Gly (SEQ ID NO: 3; iTEP$_C$); Val-Pro-Gly-Leu-Gly-Ala-Gly-Ala-Gly (SEQ ID NO: 4; iTEP$_D$); Val-Pro-Gly-Leu-Gly-Val-Gly-Ala-Gly (SEQ ID NO: 5; iTEP$_E$); Gly-Val-Leu-Pro-Gly-Val-Gly-Gly (SEQ ID NO: 6); Gly-Val-Leu-Pro-Gly (SEQ ID NO: 7); Gly-Leu-Val-Pro-Gly-Gly (SEQ ID NO: 8); Gly-Leu-Val-Pro-Gly (SEQ ID NO: 9); Gly-Val-Pro-Leu-Gly (SEQ ID NO: 10); Gly-Ile-Pro-Gly-Val-Gly (SEQ ID NO: 11); Gly-Gly-Val-Leu-Pro-Gly (SEQ ID NO: 12); Gly-Val-Leu-Pro-Gly (SEQ ID NO: 13); Gly-Val-Gly-Val-Leu-Pro-Gly (SEQ ID NO: 14); or Gly-Val-Pro-Gly (SEQ ID NO: 15).

TABLE 1

Homologous Amino Acid Repeat Sequences.

| SEQ ID NO: | Homologous Amino Acid Repeat |
|---|---|
| 1 | Gly-Val-Leu-Pro-Gly-Val-Gly |
| 2 | Gly-Ala-Gly-Val-Pro-Gly |
| 3 | Val-Pro-Gly-Phe-Gly-Ala-Gly-Ala-Gly |
| 4 | Val-Pro-Gly-Leu-Gly-Ala-Gly-Ala-Gly |
| 5 | Val-Pro-Gly-Leu-Gly-Val-Gly-Ala-Gly |
| 6 | Gly-Val-Leu-Pro-Gly-Val-Gly-Gly |
| 7 | Gly-Val-Leu-Pro-Gly |
| 8 | Gly-Leu-Val-Pro-Gly-Gly |
| 9 | Gly-Leu-Val-Pro-Gly |
| 10 | Gly-Val-Pro-Leu-Gly |
| 11 | Gly-Ile-Pro-Gly-Val-Gly |
| 12 | Gly-Gly-Val-Leu-Pro-Gly |
| 13 | Gly-Val-Leu-Pro-Gly |
| 14 | Gly-Val-Gly-Val-Leu-Pro-Gly |
| 15 | Gly-Val-Pro-Gly |

In another aspect, the homologous amino acid repeat is not the amino acid sequence: Gly-Gly-Val-Pro-Gly (SEQ ID NO: 28).

In an aspect, the homologous amino acid repeat sequence comprises four or more amino acid residues. In an aspect, the one or more of the amino acids residues is proline, and one or more of the amino acid residues is a valine. The proline and valine residues can be adjacent to each other. Alternatively, the proline and valine residues are not adjacent to each other. In some aspects, no more than one proline is present in the homologous amino acid repeat. The homologous amino acid repeat sequence can exist as a naturally occurring sequence in an elastin. The homologous amino acid repeat sequence can also be naturally flanked by one or more glycine residues at both the N-terminus and C-terminus ends.

In an aspect, the homologous amino acid repeat can be elastin-derived. The homologous amino acid repeat sequence can be derived from a mouse and/or human elastin. The homologous amino acid repeat sequence can be derived from a mouse and/or human elastin that can be further flanked by one or more glycine residues at both the C-terminus and the N-terminus ends.

In an aspect, the homologous amino acid repeat can exhibit a certain degree of identity or homology to the homologous amino acid repeat, and wherein the homologous amino acid repeat is one or more of SEQ ID NOs: 1-15, etc. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The homologous amino acid repeat of a recombinant polypeptide described herein can have at least or about 25%, 50%, 65%, 75%, 80%, 85%, 90%, 95%, 96%, 97%, 98%, or 99% identity or homology to the homologous amino acid repeat, and wherein the homologous amino acid repeat is one or more of SEQ ID NOs: 1-15, etc.

In an aspect, the recombinant polypeptide described herein can further comprise one or more residues positioned at the N-terminus, C-terminus, or both the N-terminus and C-terminus of the recombinant polypeptide. The one or more residues can be glycine, alanine or serine or a combination thereof. The one or more residues described herein can be any residue that reduces immunogenicity.

Cysteine tag. The nanoparticles described herein can comprise a cysteine containing tag. In an aspect, the iTEP-tetramers can comprise a cysteine containing tag. In an aspect, the iTEP-fusion molecules can comprise a cysteine containing tag. In an aspect, the cysteine containing tag can be $(Gly_nCys)_m$, wherein n=1 to 8; and m=4 to 8. In an aspect, the cysteine containing tag can comprise a tetracysteine motif. In an aspect, the cysteine containing tag can be a Gly-Cys-Gly-Cys-Gly-Cys-Gly-Cys (SEQ ID NO: 22). In an aspect, the cysteine containing tag can be Gly-Gly-Gly-Gly-Cys-Gly-Gly-Gly-Cys-Gly-Gly-Gly-Cys-Gly-Gly-Gly-Gly-Cys (SEQ ID NO: 23) or Gly-Gly-Gly-Gly-Gly-Gly-Gly-Cys-Gly-Gly-Gly-Gly-Gly-Gly-Gly-Cys-Gly-Gly-Gly-Gly-Gly-Gly-Gly-Cys-Gly-Gly-Gly-Gly-Gly-Gly-Gly-Cys (SEQ ID NO: 24). In an aspect, the cysteine containing tags of the one or more iTEP-tetramers and the cysteine containing tags of the one or more iTEP-fusion molecules can be crosslinked by forming one or more disulfide bonds. In an aspect, the cysteine containing tag in an iTEP-tetramer and the cysteine containing tag in an iTEP-fusion molecule form an interfusion disulfide bond.

iTEP-fusion molecules. Disclosed herein are iTEP-fusion molecules. In an aspect, the one or more iTEP-fusion molecules can comprise (i) a HisTag; (ii) a linker; (iii) a therapeutic agent; (iv) a first iTEP sequence; (v) a second iTEP sequence and (vi) a cysteine containing tag. In an aspect, the one or more iTEP-fusion molecules can comprise in amino terminal-to-carboxy terminal order (i) a HisTag; (ii) a linker; (iii) a therapeutic agent; (iv) a first iTEP sequence; (v) a second iTEP sequence and (vi) a cysteine containing tag. In an aspect, the one or more iTEP-tetramers can be amphiphilic. The order of the various components of the iTEP-fusion molecule can depend on a variety of factors including but not limited to whether the therapeutic agent is a peptide. When the therapeutic agent is not a peptide, but a small molecule, the small molecule can be included or attached to the N-terminal.

In an aspect, the ratio of iTEP-tetramers to iTEP-fusion molecules can be 10:1. In an aspect, the ratio of iTEP-tetramers to iTEP-fusion molecules can be 20:1. In an aspect, the ratio of iTEP-tetramers to iTEP-fusion molecules can be 30:1. In an aspect, the ratio of iTEP-tetramers (N) to iTEP-fusion molecules can be N:1, wherein N can be greater than 5.

HisTag. In an aspect, the one or more iTEP-fusion molecules can include a HisTag. In an aspect, the HisTag can be a polyhistidine-tag. Polyhistidine-tags are amino acid motifs comprising at least six histidine residues. In an aspect, the HisTag can be positioned at the N-terminus of the iTEP-fusion molecules. HisTags can be positioned at the N- or C-terminus of an iTEP-fusion molecule.

Linkers. The nanoparticles described herein can further comprise a one or more linkers. In an aspect, the one or more iTEP-fusion molecules can comprise one or more linkers. The linkers can be of any length, of a flexible sequence and not have any charges. Examples of linkers that can be useful in the present compositions can be found in "Fusion protein linkers: Property, design and functionality" 2013; Advanced Drug Delivery Reviews, Volume 65, Pages 1357-1369 which is incorporated by reference herein in its entirety. In an aspect, the one or more linkers are peptide-based. In an aspect, the one or more linkers can be GGGGSGGG-GSGGGGS (SEQ ID NO: 29), GGGGS (SEQ ID NO: 30), GGGGSGGGGS (SEQ ID NO: 31), or GGGGSGG-GGSGGGGSGGGGS (SEQ ID NO: 32). In an aspect, the linker of the one or more iTEP-fusion molecules can be GGGSG (SEQ ID NO: 33)

The linker can be a covalent bond. To form covalent bonds, a chemically reactive group can be used, for instance, that has a wide variety of active carboxyl groups (e.g., esters) where the hydroxyl moiety is physiologically acceptable at the levels required to modify the iTEP sequence.

Any of the iTEP sequences described herein and incorporated into the nanoparticles can be modified to chemically interact with, or to include, a linker as described herein. These modified iTEP sequences and peptide-linker constructs are within the scope of the present disclosure and can be packaged as a component of a kit with instructions for completing the process of conjugation, for example, to a therapeutic agent. Conjugation refers to the coupling, linking, for example, through a covalent bond, connecting, associating two or more molecules. The iTEP sequences can be modified to include a cysteine residue or other thio-bearing moiety (e.g., C—SH) at the N-terminus, C-terminus, or both.

In an aspect, the one or more iTEP-fusion molecules described herein can comprise a linker between the HisTag and the therapeutic agent.

Therapeutic agent. A wide variety of therapeutic agents can be incorporated, associated, or linked to the nanoparticles described herein. In an aspect, the one or more iTEP-fusion molecules can comprise a therapeutic agent. The therapeutic agent can be a chemical compound, a protein, a peptide, an antibody, a small molecule, or a cell. In an aspect, the therapeutic agent can be a peptide. In an aspect, the peptide can be a single chain variable fragment (svFv) or a biologically active variant thereof. In an aspect, the single chain variable fragment (scFv) can be a single chain variable fragment of αCTLA-4 or αPD-1 or a biologically active variant thereof. The scFv can be further engineered.

Examples of therapeutic agents include peptide vaccines, antibodies, nucleic acids (e.g., siRNA) and cell-based agents (e.g., stem cells, CAR-T cells). In some aspects, the therapeutic agents can be an anti-cancer agent. The anti-cancer agent can be an agent, vaccine or drug that has anti-cancer properties. In an aspect, the therapeutic agent can be an antibody or a fragment of an antibody. In an aspect, the anti-cancer agent has anti-microbial or anti-viral properties. In an aspect, the therapeutic agent can be an immune checkpoint inhibitor.

In an aspect, the therapeutic agent can be a scFv that binds (or specifically binds) to an immune checkpoint receptor. Examples of immune checkpoint receptors include but are not limited to PD-1, CTLA-4, CD28, ICOS, lymphocyte activation gene 3 (LAG3), T cell immunoglobulin and mucin-3 (TIM3), T cell immunoreceptor with Ig and ITIM domains (TIGIT), CD137 (4-1BB), OX40, CD27, and B- and T-lymphocyte attenuator (BTLA) or biological variants thereof. In an aspect, the immune checkpoint receptor can be PD-1 or CTLA-4.

In other aspects, the iTEP-fusion molecules, described herein, can comprise a scFv of an anti-programmed cell death protein 1 (PD-1) antibody. In an aspect, the therapeutic agent can be a peptide. In an aspect, the peptide can be a scFv. In an aspect, the scFv can be derived from an anti-PD-1 antibody. The scFv can be derived from any anti-PD-1 antibody. Examples of anti-PD-1 antibodies include but are not limited to nivolumab, pembrolizumab, pidilizumab, MEDI0680, BMS-936559, clone J116, Keytruda®, Opdivo® or a biologically active variant thereof.

In an aspect, the therapeutic agent can be a scFv of a cytotoxic T-lymphocyte-associated protein 4 (CTLA-4). In an aspect, the scFv can be derived from an anti-CTLA-4 antibody. The scFv can be derived from any anti-CTLA-4 antibody. Examples of anti-CTLA-4 antibodies include but are not limited to ipilimumab, tremelimumab and UC10-4F10 clone or biological variants thereof. In an aspect, the anti-CTLA-4 antibody can be ipilimumab.

In an aspect, the scFv can be designed based on CDR information of an anti-PD-1 antibody. In an aspect, complementarity-determining regions (CDRs) of the heavy chain or light chain of an anti-PD-1 antibody can be used in to prepare an anti-PD-1 antibody or a fragment thereof (e.g. scFv). For example, disclosed herein are anti-PD-1 antibodies comprising one or more of CDRs including CDRs of the heavy chain: SSYRWN (SEQ ID NO: 34), YINSAGISNYNPSLKR (SEQ ID NO: 35), and SDNMGTTPFTY (SEQ ID NO: 36); or CDRs of the light chain: RSSKSLLYSDGKTYLN (SEQ ID NO: 37), WMSTRAS (SEQ ID NO: 38), and QQGLEFPT (SEQ ID NO: 39).

Disclosed herein are anti-PD-1 antibodies comprising mutations in the $V_H$ and $V_L$, respectively of an αPD-1. For example, two mutations can be $V_H$: R45C; $V_L$: G104C. In an aspect, disclosed herein can be an antibody or antigen-binding portion thereof, comprising: a heavy chain sequence and a light chain sequence, wherein the heavy chain sequence comprises SEQ ID NO: 45 and wherein the light chain sequence comprises SEQ ID NO: 46. In an aspect, the heavy and light chain sequences can exhibit a certain degree of identity or homology to the SEQ ID NOs: 45 or 46. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The heavy and light chain sequences of an anti-PD-1 antibody comprising one or more mutations $V_H$ and $V_L$, respectively of an αPD-1 as described herein can have at least or about 25%, 50%, 65%, 75%, 80%, 85%, 90%, 95%, 96%, 97%, 98%, or 99% identity or homology to SEQ ID NOs: 45 and/or 46.

In an aspect, one or more of the heavy or light chain CDR sequences can comprise at least one substitution or at least one amino acid substitution compared to the parent heavy or light chain sequence (e.g., SEQ ID Nos: 45 or 46). In an aspect, one or more of the heavy or light chain CDR sequences can comprise at least one substitution or at least one amino acid substitution compared to the parent CDR (e.g., SEQ ID Nos: 34, 35, 36, 37, 38 or 39).

In some aspects, the CDRs disclosed herein can also include variants. Generally, the amino acid identity between individual variant CDRs can be at least 90%, 91%, 92%, 93%, 94%, 95%, 96%, 97%, 98%, 99% or 100%. Thus, a "variant CDR" can be one with the specified identity to the parent CDR as disclosed herein, and shares biological function, including, but not limited to, 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

Disclosed herein are anti-PD-1 antibodies comprising mutations in the $V_H$ and $V_L$, respectively of an αPD-1. For example, two mutations can be $V_H$: R45C; $V_L$: G104C. In an aspect, disclosed herein is an antibody or antigen-binding portion thereof, comprising: a heavy chain sequence and a light chain sequence, wherein the heavy chain sequence comprises SEQ ID NO: 45 and wherein the light chain sequence comprises SEQ ID NO: 46, and wherein the antibody comprises one or more of CDRs selected from the group of SSYRWN (SEQ ID NO: 34), YINSAGISNYNPSLKR (SEQ ID NO: 35), SDNMGTTPFTY (SEQ ID NO: 36), RSSKSLLYSDGKTYLN (SEQ ID NO: 37), WMSTRAS (SEQ ID NO: 38), and QQGLEFPT (SEQ ID NO: 39).

Disclosed herein are antibodies or antigen-binding portion thereof, comprising: a heavy chain sequence and a light chain sequence, wherein the heavy chain sequence comprises SEQ ID NO: 45 and wherein the light chain sequence comprises SEQ ID NO: 46, and wherein the antibody comprises one or more of CDRs selected from the group of SSYRWN (SEQ ID NO: 34), YINSAGISNYNPSLKR (SEQ ID NO: 35), SDNMGTTPFTY (SEQ ID NO: 36), RSSKSLLYSDGKTYLN (SEQ ID NO: 37), WMSTRAS (SEQ ID NO: 38), and QQGLEFPT (SEQ ID NO: 39).

Disclosed herein are antibodies or antigen-binding portion thereof, comprising: a heavy chain sequence and a light chain sequence, wherein the heavy chain sequence consists of SEQ ID NO: 45 and wherein the light chain sequence consists of SEQ ID NO: 46.

Disclosed herein are antibodies or antigen-binding portion thereof, comprising: a heavy chain sequence and a light chain sequence, wherein the heavy chain sequence consists of SEQ ID NO: 45 and wherein the light chain sequence consists of SEQ ID NO: 46, and wherein the antibody comprises one or more of CDRs selected from the group of SSYRWN (SEQ ID NO: 34), YINSAGISNYNPSLKR (SEQ ID NO: 35), SDNMGTTPFTY (SEQ ID NO: 36), RSSKSLLYSDGKTYLN (SEQ ID NO: 37), WMSTRAS (SEQ ID NO: 38), and QQGLEFPT (SEQ ID NO: 39).

Disclosed herein are antibodies or antigen-binding portion thereof, comprising: a heavy chain sequence and a light chain sequence, wherein the heavy chain sequence consists of SEQ ID NO: 45 and wherein the light chain sequence consists of SEQ ID NO: 46, and wherein the antibody comprises one or more of CDRs selected from the group of SSYRWN (SEQ ID NO: 34), YINSAGISNYNPSLKR (SEQ ID NO: 35), SDNMGTTPFTY (SEQ ID NO: 36), RSSKSLLYSDGKTYLN (SEQ ID NO: 37), WMSTRAS (SEQ ID NO: 38), and QQGLEFPT (SEQ ID NO: 39).

As described herein, SEQ ID NO: 45 is an example of a heavy chain sequence and SEQ ID NO: 46 is an example of a light chain sequence In an aspect, the scFv can be from an anti-PD-1 antibody comprising mutations in the $V_H$ and $V_L$, respectively of an αPD-1. An example of two are $V_H$: R45C; $V_L$: G104C. In an aspect, disclosed herein is an antibody or antigen-binding portion thereof, comprising: a heavy chain sequence and a light chain sequence, wherein the heavy chain sequence comprises SEQ ID NO: 45 and wherein the light chain sequence comprises SEQ ID NO: 46, and wherein the antibody comprises one or more of CDRs selected from the group of SSYRWN (SEQ ID NO: 34), YINSAGIS-NYNPSLKR (SEQ ID NO: 35), SDNMGTTPFTY (SEQ ID NO: 36), RSSKSLLYSDGKTYLN (SEQ ID NO: 37), WMSTRAS (SEQ ID NO: 38), and QQGLEFPT (SEQ ID NO: 39).

In an aspect, the scFv can be from an antibody or antigen-binding portion thereof, comprising: a heavy chain sequence and a light chain sequence, wherein the heavy chain sequence comprises SEQ ID NO: 45 and wherein the light chain sequence comprises SEQ ID NO: 46, and wherein the antibody comprises one or more of CDRs selected from the group of SSYRWN (SEQ ID NO: 34), YINSAGISNYNPSLKR (SEQ ID NO: 35), SDNMGTTPFTY (SEQ ID NO: 36), RSSKSLLY-SDGKTYLN (SEQ ID NO: 37), WMSTRAS (SEQ ID NO: 38), and QQGLEFPT (SEQ ID NO: 39).

In an aspect, the scFv can be from antibody or antigen-binding portion thereof, comprising: a heavy chain sequence and a light chain sequence, wherein the heavy chain sequence consists of SEQ ID NO: 45 and wherein the light chain sequence consists of SEQ ID NO: 46.

In an aspect, the scFv can be from antibody or antigen-binding portion thereof, comprising: a heavy chain sequence and a light chain sequence, wherein the heavy chain sequence consists of SEQ ID NO: 45 and wherein the light chain sequence consists of SEQ ID NO: 46, and wherein the antibody comprises one or more of CDRs selected from the group of SSYRWN (SEQ ID NO: 34), YINSAGIS-NYNPSLKR (SEQ ID NO: 35), SDNMGTTPFTY (SEQ ID NO: 36), RSSKSLLYSDGKTYLN (SEQ ID NO: 37), WMSTRAS (SEQ ID NO: 38), and QQGLEFPT (SEQ ID NO: 39)

In an aspect, the scFv can be from antibody or antigen-binding portion thereof, comprising: a heavy chain sequence and a light chain sequence, wherein the heavy chain sequence consists of SEQ ID NO: 45 and wherein the light chain sequence consists of SEQ ID NO: 46, and wherein the antibody comprises one or more of CDRs selected from the group of SSYRWN (SEQ ID NO: 34), YINSAGIS-NYNPSLKR (SEQ ID NO: 35), SDNMGTTPFTY (SEQ ID NO: 36), RSSKSLLYSDGKTYLN (SEQ ID NO: 37), WMSTRAS (SEQ ID NO: 38), and QQGLEFPT (SEQ ID NO: 39)

In an aspect, the scFv can be from an anti-programmed death-1 antibody. In an aspect, the scFv can be from Keytruda® or Opdivo®.

If the therapeutic agent is a non-peptide, then the therapeutic agent can be prepared as a fusion conjugate. The therapeutic agent can be substituted for a conjugate (referred to as a fusion conjugate or a therapeutic conjugate) such that the one or more iTEP-fusion molecules comprise a (i) a HisTag; (ii) a linker; (iii) therapeutic conjugate; (iv) a first iTEP sequence; (v) a second iTEP sequence and (vi) a cysteine containing tag. In some aspects, the therapeutic conjugate can be associated with or linked to the first iTEP sequence at its amino terminus.

Disclosed herein are vectors. In an aspect, vectors can comprise nucleic acids that encode the nanoparticles described herein. In an aspect, the vectors can comprise nucleic acids that encode any of the components described herein of the nanoparticles.

Design. In an aspect, the iTEPs described herein can be designed as polymers of peptides derived from elastin. The individual iTEP sequences should be humorally tolerant in mice and humans. The iTEPs selected should not intrinsically induce an autoimmune response (i.e., the sequences should not intrinsically bind to B cell or T cell receptors).

To reduce the possibility of generating recombinant polypeptides that are immunogenic, two strategies can be employed. First, common, existing peptide repeats within human and mouse elastins can be used as a component of the homologous amino acid repeat to limit generating extrinsic junction sequences. Second, when one or more extrinsic junction sequences were produced, the homologous amino acid repeats should be four residues or longer and from elastins; and be flanked by one or more glycine residues at the N- and C-terminuses. By using homologous amino acid repeats that are longer rather than shorter, the number of extrinsic junction sequences can be reduced. Reducing or eliminating extrinsic junction sequences may reduce the immunogenicity of the recombinant polypeptide or homologous amino acid repeat.

In some aspects, for the homologous amino acid repeats to have the phase transition property, they can be designed to have one proline residue and one or more valine residues.

The iTEPs useful as iTEP fusions, iTEP-fusion molecules or as iTEP-tetramers can be produced by synthetic methods and recombinant techniques used routinely to produce proteins from nucleic acids. The iTEPs can be stored in an unpurified or in an isolated or substantially purified form until later use.

In an aspect, the therapeutic agent can be encapsulated or loaded onto the first iTEP sequence (or iTEP fusion or recombinant polypeptide) using methods known to one of ordinary skill in the art. The encapsulated therapeutic agent can be determined by high performance liquid chromatography.

Configurations. Each part of the nanoparticles, including the MHC class I monomers, iTEP sequences, cysteine containing tags, HisTags, therapeutic agents, and linkers, can be selected independently. One of ordinary skill in the art would understand that the component parts need to be associated in a compatible manner. The nanoparticles can be used to deliver therapeutic agents to a patient for the treatment of cancer or autoimmune disorders or diseases. The nanoparticles disclosed herein can be used to selectively target cancer-reactive cells or activated cytotoxic T cells. The number of therapeutic agents per nanoparticle can be controlled by adding more iTEP-fusion molecules (e.g., diblock polymers, iTEP fusion proteins). Accordingly, in some aspects, the therapeutic agents can be two or more.

In some aspects, the iTEP-tetramers and the iTEP-fusion molecules can be present in a ratio of 1:1 (iTEP-tetramer: iTEP-fusion molecules). The iTEP-tetramer:iTEP-fusion molecule ratio can also be 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 35:1, 40:1, 45:1, 50:1 or any other combinations thereof.

Labels. The nanoparticles described herein can further comprise one or more labels or detection tags. (e.g., FLAG™ tag, epitope or protein tags, such as myc tag, 6 His, and fluorescent fusion protein). In an aspect, the label (e.g., FLAG™ tag) can be fused to a component of the nanoparticle (e.g., iTEP). In an aspect, the disclosed methods and compositions further comprise a fusion protein, or a polynucleotide encoding the same. In various aspects, the fusion protein comprises at least one epitope-providing amino acid sequence (e.g., "epitope-tag"), wherein the epitope-tag is selected from an epitope-tag added to the N- and/or C-terminus of the protein (e.g., iTEP). In some aspects, the label can be encapsulated inside the nanoparticles (e.g., attached to the iTEP). In some aspects, the lable can be attached to the outer surface of the nanoparticles.

Epitope tags are short stretches of amino acids to which a specific antibody can be raised, which in some aspects allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western blotting"), and affinity chromatography. Epitope tags add a known epitope (e.g., antibody binding site) on the subject protein, to provide binding of a known and often high-affinity antibody, and thereby allowing one to specifically identify and track the tagged protein that has been added to a living organism or to cultured cells. Examples of epitope tags include, but are not limited to, myc, T7, GST, GFP, HA (hemagglutinin), V5 and FLAG tags. The first four examples are epitopes derived from existing molecules. In contrast, FLAG is a synthetic epitope tag designed for high antigenicity (see, e.g., U.S. Pat. Nos. 4,703,004 and 4,851,341). Epitope tags can have one or more additional functions, beyond recognition by an antibody.

In an aspect, the disclosed methods and compositions comprise an epitope-tag wherein the epitope-tag has a length of between 6 to 15 amino acids. In an alternative aspect, the epitope-tag has a length of 9 to 11 amino acids. The disclose methods and compositions can also comprise a fusion protein comprising two or more epitope-tags, either spaced apart or directly in tandem. Further, the disclosed methods and composition can comprise 2, 3, 4, 5 or even more epitope-tags, as long as the fusion protein maintains its biological activity/activities (e.g., "functional").

In an aspect, the epitope-tag is a VSV-G tag, CD tag, calmodulin-binding peptide tag, S-tag, Avitag, SF-TAP-tag, strep-tag, myc-tag, FLAG-tag, T7-tag, HA (hemagglutinin)-tag, His-tag, S-tag, GST-tag, or GFP-tag. The sequences of these tags are described in the literature and well known to the person of skill in art.

As described herein, the term "immunologically binding" is a non-covalent form of attachment between an epitope of an antigen (e.g., the epitope-tag) and the antigen-specific part of an antibody or fragment thereof. Antibodies are preferably monoclonal and must be specific for the respective epitope tag(s) as used. Antibodies include murine, human and humanized antibodies. Antibody fragments are known to the person of skill and include, amongst others, single chain Fv antibody fragments (scFv fragments) and Fab-fragments. The antibodies can be produced by regular hybridoma and/or other recombinant techniques. Many antibodies are commercially available.

The construction of fusion proteins from domains of known proteins, or from whole proteins or proteins and peptides, is well known. Generally, a nucleic acid molecule that encodes the desired protein and/or peptide portions are joined using genetic engineering techniques to create a single, operably linked fusion oligonucleotide. Appropriate molecular biological techniques can be found in Sambrook et al. (Molecular Cloning: A laboratory manual Second Edition Cold Spring Harbor Laboratory Press, Cold spring harbor, NY, USA, 1989). Examples of genetically engineered multi-domain proteins, including those joined by various linkers, and those containing peptide tags, can be found in the following patent documents: U.S. Pat. No. 5,994,104 ("Interleukin-12 fusion protein"); U.S. Pat. No. 5,981,177 ("Protein fusion method and construction"); U.S. Pat. No. 5,914,254 ("Expression of fusion polypeptides transported out of the cytoplasm without leader sequences"); U.S. Pat. No. 5,856,456 ("Linker for linked fusion polypeptides"); U.S. Pat. No. 5,767,260 ("Antigen-binding fusion proteins"); U.S. Pat. No. 5,696,237 ("Recombinant antibody-toxin fusion protein"); U.S. Pat. No. 5,587,455 ("Cytotoxic agent against specific virus infection"); U.S. Pat. No. 4,851,341 ("Immunoaffinity purification system"); U.S. Pat. No. 4,703,004 ("Synthesis of protein with an identification peptide"); and WO 98/36087 ("Immunological tolerance to HIV epitopes").

The placement of the functionalizing peptide portion (epitope-tag) within the subject fusion proteins can be influenced by the activity of the functionalizing peptide portion and the need to maintain at least substantial fusion protein, such as TCR, biological activity in the fusion. Two methods for placement of a functionalizing peptide are: N-terminal, and at a location within a protein portion that exhibits amenability to insertions. Though these are not the only locations in which functionalizing peptides can be inserted, they serve as good examples, and will be used as illustrations. Other appropriate insertion locations can be identified by inserting test peptide encoding sequences (e.g., a sequence encoding the FLAG peptide) into a construct at different locations, then assaying the resultant fusion for the appropriate biological activity and functionalizing peptide activity, using assays that are appropriate for the specific portions used to construct the fusion. The activity of the subject proteins can be measured using any of various known techniques, including those described herein.

Methods of Making Immune-Tolerant Elastin-Like Polypeptides Tetramers

As used herein, the term "immune-tolerant elastin-like polypeptide (iTEP)-tetramers" refers to a protein comprising in amino terminal-to-carboxy terminal order (i) four MHC class I monomers, (ii) a first iTEP sequence, (iii) a second iTEP sequence and (iv) a cysteine containing tag.

Disclosed herein are methods that can be used to produce iTEP-tetramers disclosed herein. The methods can include mixing one or more iTEP fusion peptides with four or more biotinylated MHC class I monomers under conditions to allow four or more biotinylated MHC class I monomers to bind to the four or more streptavidin moieties of the iTEP fusion peptide. The binding of the four or more biotinylated MHC class I monomers to the four or more streptavidin moieties of the iTEP fusion peptide results in an iTEP-tetramer. In an aspect, the one or more iTEP fusion peptides can comprise in amino terminal-to-carboxy terminal order a (i) a HisTag; (ii) a linker; (iii) four or more streptavidin moieties, (iv) a first iTEP sequence, (v) a second iTEP sequence and (vii) a cysteine containing tag. In an aspect, the four or more biotinylated MHC class I monomers can be H2-D$^b$/gp100 epitope, H2-K$^b$/TRP-1 epitope, H2-K$^b$/TRP-2 epitope, or the other complexes of MHC class I/tumor-associated epitopes. Each of the four or more biotinylated MHC class I monomers can be the same. In other words, for each tetramer, the same MHC class I/tumor-associated epitopes or MHC class I monomers can be used. In some aspects, each nanoparticle would also have the same tetramer (e.g., same MHC class I/tumor-associated epitopes or MHC class I monomers). In some aspects, each nanoparticle can also have one or more tetramers such that the MHC class I/tumor-associated epitopes or MHC class I monomers differ. Thus, a nanoparticle can have a combination of biotinylated MHC class I monomers as long as the biotinylated MHC class I monomers are the same for each tetramer.

Disclosed herein are purified iTEP-tetramers produced by the method disclosed herein. Purification techniques are within the ability of one of ordinary skill in the art.

In some aspects, the method of making or producing iTEP-tetramers can include a) expressing an iTEP fusion (e.g., a first iTEP sequence fused to a second iTEP sequence) in a genetically modified cell, b) solubilizing the iTEP fusion; and c) mixing (or binding) the iTEP fusion peptide with four biotinylated MHC class I monomers. In an aspect, the iTEP fusion peptide comprises in amino terminal-to-carboxy terminal order a (i) a HisTag; (ii) a linker; (iii) streptavidin, (iv) a first iTEP sequence, (v) a second iTEP sequence and (vii) a cysteine containing tag. The streptavidin is bound to the biotin, thereby producing the iTEP tetramer.

In the methods disclosed herein, other proteins that bind biotin with a high affinity can be used. In an aspect, avidin can be used in place of the streptavidin.

In an aspect, the iTEP fusion disclosed herein can be a recombinant iTEP fusion or diblock polypeptide or diblock polymer.

In an aspect, the step of expressioning an iTEP fusion in a genetically modified cell can be performed in a bacterial expression system. It can be expressed in a variety of expression systems (e.g., *Escherichia coli*, yeast, insect cell, and mammalian cell cultures; and plants). In an aspect, the bacterial expression system can be an *Escherichia coli* expression system. Examples of bacterial expression systems that can be used in the methods disclosed herein include but are not limited to yeast protein expression systems (e.g., *Saccharomyces cerevisiae*), insect cell expression systems (e.g., sf9 and sf21) and mammalian cell expression systems (e.g., HEK293 and CHO).

Briefly, a plasmid DNA encoding any of the iTEP fusions described herein can be transfected into cells of any of the expression systems described above. After the iTEP fusion (e.g., (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21)) is produced in any one of these systems, they can then also be purified, lyophilized and stored until use.

Methods of Making Nanoparticles

Disclosed herein are methods of producing the nanoparticles described herein. The method can include: mixing one or more immune-tolerant elastin-like polypeptide (iTEP) fusion peptides with four or more biotinylated MHC class I monomers under conditions that allow four or more biotinylated MHC class I monomers to bind to the four or more streptavidin moieties of the iTEP fusion peptide. The binding of the four or more biotinylated MHC class I monomers to the four or more streptavidin moieties of the iTEP fusion peptide results in an iTEP-tetramer. The one or more iTEP fusion peptides can comprise in amino terminal-to-carboxy terminal order a (i) a HisTag; (ii) a linker; (iii) four or more streptavidin moieties, (iv) a first iTEP sequence, (v) a second iTEP sequence and (vii) a cysteine containing tag. The method can also include the step of mixing the iTEP-tetramer with an iTEP-fusion molecule. The iTEP-tetramer and the iTEP-fusion molecule can be mixed at a ratio of, for example, 10:1. The ratio of the iTEP-tetramer and the iTEP-fusion molecule can be any ratio disclosed herein. The cysteine containing tag in the first mixing step and the cysteine containing tag in the second mixing step can be crosslinked via one or more disulfide bonds. The iTEP-fusion molecule can comprise (i) a HisTag; (ii) a linker; (iii) single chain variable fragment (scFv); (iv) a first iTEP sequence; (v) a second iTEP sequence and (vi) a cysteine containing tag. The method can further include the step of oxidizing the one or more disulfide bonds between the iTEP-tetramer and iTEP-fusion molecule, thereby forming a stable nanoparticle. In an aspect, the single chain variable fragment (scFv) can be a single chain variable fragment of αCTLA-4 or αPD-1 or a biologically active variant thereof.

In an aspect, the method can further comprise prior to the first mixing step, expressing the iTEP fusion in a genetically modified cell. Further, in another aspect, the method can include the step of solubilizing the iTEP fusion immediately prior to the first mixing step.

The methods disclosed herein related to the process of producing the nanoparticles as described herein can be readily modified to produce a pharmaceutically acceptable salt of the nanoparticles. Pharmaceutical compositions including such salts and methods of administering them are within the scope of the present disclosure.

Pharmaceutical Compositions

As disclosed herein, are pharmaceutical compositions, comprising the nanoparticles (the iTEP-tetramers and iTEP-fusion molecules) and a pharmaceutical acceptable carrier described above. In some aspects, the therapeutic agent can be a single chain variable fragment (scFv) of αCTLA-4 or αPD-1 and the pharmaceutical composition can be formulated for intravenous administration. The compositions of the present disclosure also contain a therapeutically effective amount of the nanoparticles as described herein. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the nanoparticles. Thus, compositions can be prepared for parenteral administration that includes nanoparticles dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein, are methods of treating a patient with cancer, the method comprising: (a) identifying a patient in need of treatment; and (b) administering to the patient a therapeutically effective amount of the pharmaceutical composition comprising nanoparticles. The nanoparticles can comprise: a) one or more immune-tolerant elastin-like polypeptide (iTEP)-tetramers, wherein the one or more iTEP-tetramers comprise in amino terminal-to-carboxy terminal order (i) four MHC class I monomers, (ii) a first iTEP sequence, (iii) a second iTEP sequence and (iv) a cysteine containing tag; and b) one or more iTEP-fusion molecules, wherein the one or more iTEP-fusion molecules comprise (i) a HisTag; (ii) a linker; (iii) therapeutic agent; (iv) a first iTEP sequence; (v) a second iTEP sequence and (vi) a cysteine containing tag, and a pharmaceutically acceptable carrier.

The pharmaceutical compositions described above can be formulated to include a therapeutically effective amount of the nanoparticles disclosed hererin. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of cancer or autoimmune disease or disorder. In some aspects, the patient has an autoimmune disease or disorder. In some aspects, the autoimmune disease can be non-Hodgkin's lymphoma, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In other aspects, the autoimmune disease can be Type I diabetes mellitus, multiple sclerosis, or rheumatoid arthritis. In an aspect, the autoimmune disease can be Type I diabetes mellitus. In an aspect, the autoimmune disease can be multiple sclerosis.

The compositions described herein can be formulated in a variety of combinations. The particular combination of any of the nanoparticles with a second and different composition (including another nanoparticle composition disclosed herein) can vary according to many factors, for example, the particular type and severity of the cancer or autoimmune disease or disorder.

Any of the compositions described herein can be administered as a "combination."

The pharmaceutical compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with cancer (or autoimmune disease or disorder) in an amount sufficient to at least partially improve a sign or symptom or to inhibit the progression of (and preferably arrest) the symptoms of the condition, its complications, and consequences. In some aspects, compositions can be administered to a subject (e.g., a human patient) already with or diagnosed with cancer (or an autoimmune disease or disorder). In some aspects, compositions can be administered to a subject (e.g., a human patient) already with or diagnosed with cancer and with or diagnosed with an autoimmune disease or disorder in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effect amount includes amounts that provide a treatment in which the onset or progression of the cancer (or autoimmune disease or disorder) is delayed, hindered, or prevented, or a symptom of the cancer (or autoimmune disease or disorder) is ameliorated. One or more of the symptoms can be less severe. Recovery can be accelerated in an individual who has been treated.

In some aspects, the cancer can be a primary or secondary tumor. In other aspects, the primary or secondary tumor can be within the patient's breast, lung, skin, kidneys, bladder, head, neck, lymphatic system, liver, brain, esophagus, digestion system, stomach or ovaries.

Disclosed herein, are methods of treating a patient with cancer. The cancer can be any cancer. In some aspects, the cancer can be breast cancer, ovarian cancer, lung cancer (e.g., non-small cell lung cancer, melanoma, kidney cancer, renal cell cancer, bladder cancer, head and neck cancers, lymphomas (including but not limited to Hodgkin's lymphoma), stomach cancer, ovarian cancer, brain cancer, glioblastoma, esophageal cancer, gastroesophageal cancer, stomach/esophagus junction cancer, multiple myeloma, skin cancer or gastric cancer. In an aspect, the cancer can be melanoma.

Amounts effective for this use can depend on the severity of the cancer and the weight and general state and health of the subject, but generally range from about 0.1 mg/Kg body to about 10.0 mg/Kg body weight per dose per subject. Suitable regimes for initial administration and booster administrations are typified by an initial administration followed by repeated doses at one or more hourly, daily, weekly, or monthly intervals by a subsequent administration. For example, a subject can receive nanoparticles in the range of about 0.1 mg/Kg body weight to about 10 mg/Kg body weight per dose one or more times per week (e.g., 2, 3, 4, 5, 6, or 7 or more times per week). For example, a subject can receive 0.1 mg/Kg body weight to 10 mg/Kg body weight (e.g., 0.3, 1.0, 3.0, 10.0 mg/Kg body weight) dose per week. A subject can also receive nanoparticles in the range of 0.1 mg/Kg body weight to 10 mg/Kg body weight per dose once every two or three weeks. The total effective amount of an nanoparticles in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of one or more of the therapeutic agents present within the compositions described herein and used in the methods as disclosed herein applied to mammals (e.g., humans) can be determined by one of ordinary skill in the art with consideration of individual differences in age, weight, and other general conditions (as mentioned above).

Because the nanoparticles of the present disclosure can be stable in serum and the bloodstream and in some cases more specific, the dosage of the nanoparticles including any individual component can be lower (or higher) than an effective dose of any of the individual components when unbound or not a part of the nanoparticle. Accordingly, in some aspects, the therapeutic agent administered has increased efficacy or reduced toxicity or side effects when administered as part of the nanoparticle as compared to when the therapeutic agent is administered alone or not as part of the nanoparticle.

Disclosed herein, are methods of treating a patient with cancer, the method comprising: (a) identifying a patient in need of treatment; and (b) administering to the patient a therapeutically effective amount of the pharmaceutical composition comprising any of the nanoparticles disclosed herein. The pharmaceutical composition can also include a pharmaceutically acceptable carrier. In an aspect, the administration of the pharmaceutical composition described herein can be combined with a second and different pharmaceutical composition.

The method includes, for example, administering a therapeutically effective amount of: 1) a nanoparticle comprising a scFv of an anti-PD-1 antibody alone; 2) a nanoparticle comprising a scFv of an anti-PD-1 antibody in combination with a cancer vaccine (e.g., TEGVAX, Fu, J. et al., Preclinical evidence that PD-1 blockade cooperates with cancer vaccine TEGVAX to elicit regression of established tumors, Cancer Research, 2014 Aug. 1; 74(15):4042-52); 3) a nanoparticle comprising a scFv of an anti-CTLA-4 antibody alone; 4) a nanoparticle comprising a scFv of an anti-CTLA-4; antibody in combination with a cancer vaccine; 5) a nanoparticle comprising a scFv of an anti-PD-1 antibody in combination with any cancer chemotherapeutic agent(s); 6) a nanoparticle comprising a scFv of an anti-CTLA-4 antibody in combination with any cancer chemotherapeutic agent(s) (e.g., dacarbazine, Robert et al., Ipilimumab plus Dacarbazine for Previously Untreated Metastatic Melanoma, N Engl J Med 2011, 364:2517-2526); and 7) a nanoparticle comprising a scFv of an anti-PD-1 antibody in combination with a nanoparticle comprising a scFv of an anti-CTLA-4 antibody.

The combination therapies disclosed herein can be administered as one or more pharmaceutical compositions and, if separately, can be administered simultaneously or sequentially in any order.

In some aspects, the compositions can include a mixture of two or more such compounds in equal or unequal amounts.

The particular combination of agents can vary according to many factors, for example, the particular kind of cancer, the severity of the cancer, any comorbidities, and the health of the patient.

When a combination of any of the compositions disclosed herein is administered to the same patient, they can be administered in a single formulation (e.g., a co-formulation) or in separate formulations (which may be the same or different) that can be administered concurrently or sequentially.

Kits

The nanoparticles and compositions described herein can be packaged in a suitable container labeled, for example, for use as a therapy to treat cancer or an autoimmune disease or disorder or for use in in any of the methods disclosed herein. Accordingly, packaged products (e.g., sterile containers containing the nanoparticles or compositions described herein and packaged for storage, shipment, or sale at concentrated or ready-to-use concentrations) and kits, including at least one or more immune-tolerant elastin-like polypeptide (iTEP)-tetramers and one or more iTEP-fusion molecules as described herein and instructions for use, are also within the scope of the disclosure. A product can include a container (e.g., a vial, jar, bottle, bag, or the like) containing the nanoparticles or compositions described herein. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The compositions or nanoparticles can be ready for administration (e.g., present in dose-appropriate units), and may include a pharmaceutically acceptable adjuvant, carrier or other diluent. Alternatively, the compositions or nanoparticles can be provided in a concentrated form with a diluent and instructions for dilution.

In an aspect, the kits disclosed herein can comprise: a) one or more immune-tolerant elastin-like polypeptide (iTEP)-tetramers, wherein the one or more iTEP-tetramers comprise in amino terminal-to-carboxy terminal order (i) four MHC class I monomers, (ii) a first iTEP sequence, (iii) a second iTEP sequence and (iv) a cysteine containing tag; and b) one or more iTEP-fusion molecules, wherein the one or more iTEP-fusion molecules comprise (i) a HisTag; (ii) a linker; (iii) single chain variable fragment (scFv); (iv) a first iTEP sequence; (v) a second iTEP sequence and (vi) a cysteine containing tag. In an aspect, the cysteine containing tags of the one or more iTEP-tetramers and the cysteine tags of the one or more iTEP-fusion molecules are not crosslinked. In an aspect, the kit further comprises a reducing agent. In an aspect, the kit further comprises an oxidizing agent. In an aspect, the thiol groups of the cysteine containing tags of the one or more iTEP-tetramers and the cysteine tags of the one or more iTEP-fusion molecules can be protected.

EXAMPLES

Figure 1A:
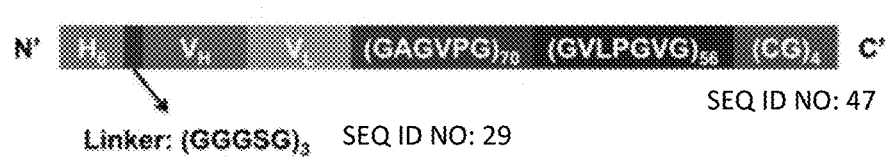
FIG. 1A-C shows the PD-1(scFv)-iTEP fusion and sizes of the fusion gene.
Figure 1B:
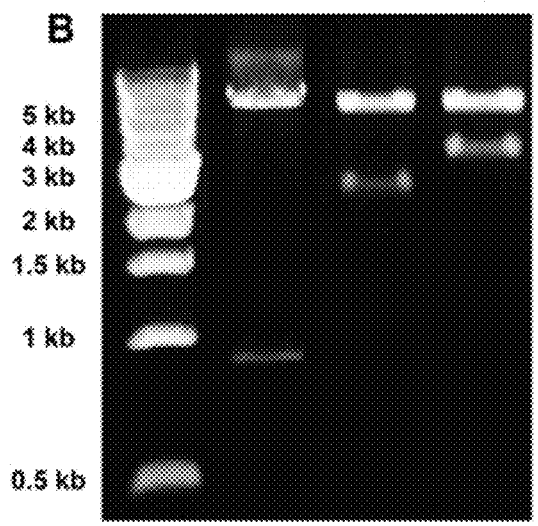
Figure 2:
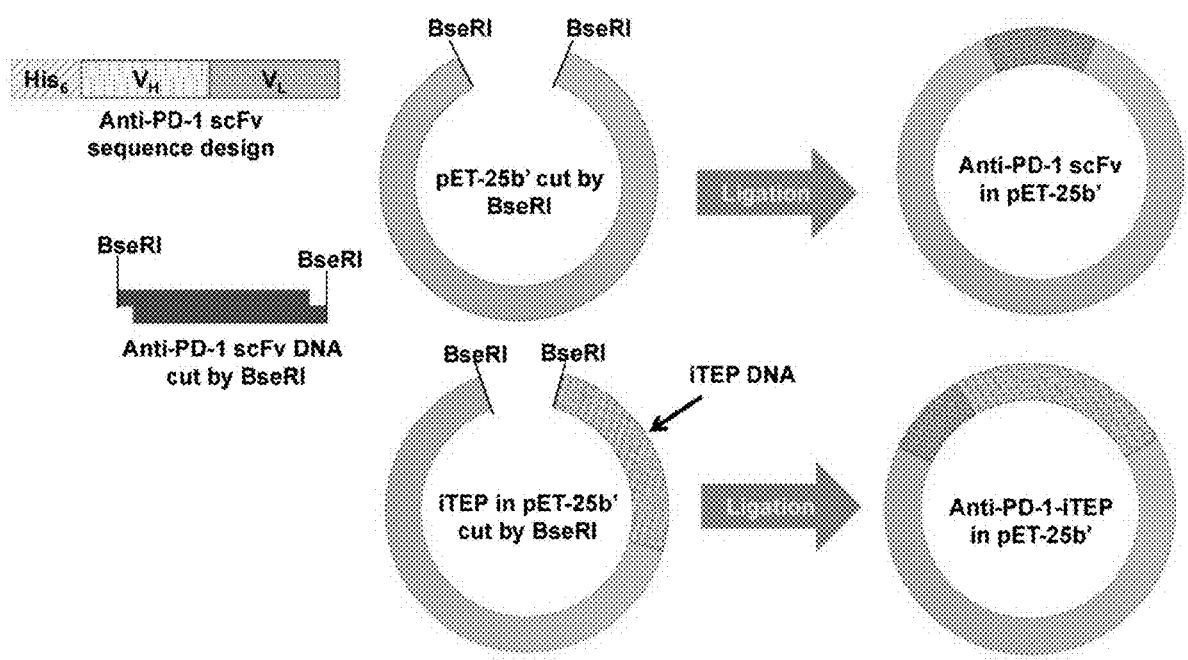
FIG. 2 is a schematic example of the insertion of the coding genes of the scFv and the iTEP fusion into the pET-25b(+) expression vector.

Example 1: Design and Generation of αPD-1 scFv and αPD-1-iTEP Fusion as Recombinant Proteins Both the heavy chain and light chain cDNAs of the αPD-1 (RMP1-14 clone) were sequenced. According to the sequencing results, the three complementarity-determining regions (CDRs) of the heavy chain are: SSYRWN (SEQ ID NO: 34), YINSAGISNYNPSLKR (SEQ ID NO: 35), and SDNMGTTPFTY (SEQ ID NO: 36); the three CDRs of the light chain are: RSSKSLLYSDGKTYLN (SEQ ID NO: 37), WMSTRAS (SEQ ID NO: 38), and QQGLEFPT (SEQ ID NO: 39). Based on the CDR information, an scFv of the αPD-1, $NH_2$-Histag($H_6$)-(GGGSG)$_3$-$V_H$-(GGGSG)$_4$-$V_L$—COOH was designed, and a coding gene was synthesized to express the scFv as a recombinant protein. Next, an αPD-1(scFv)-iTEP fusion was designed as illustrated in FIG. 1A. The amphiphilic diblock iTEP, $NH_2$-(GAGVPG)$_{70}$-(GVLPGVG)$_{56}$-(GC)$_4$—COOH, was included to drive the fusion to self-assemble into a micelle-like NP. The coding genes of the scFv and the fusion were inserted into the pET-25b(+) expression vector (FIG. 2). The sizes of the coding genes were examined using gel electrophoresis after the genes from their host pET-25b(+) vector were cleaved. On the basis of the gel image (FIG. 1B), the size of the scFv gene is between 0.5 kb and 1.0 kb; the size of the fusion gene is between 3.0 kb and 4.0 kb. These estimated sizes are consistent with the theoretical sizes of the scFv gene and the fusion gene, 792 bp and 3252 bp, respectively. Three plasmids were digested with two restriction enzymes, BamHI and XbaI, which flanked the BseRI sites by which the genes were inserted into the pET-25b(+) vector. The upper bands of each lane represent the pET-25b(+) vectors; the lower bands of each lane represent the coding genes. These two coding genes were also fully sequenced to confirm their accuracy. Amino acid residual numbers, theoretical sizes of their coding genes, and theoretical molecular weight of the scFv and the fusion were listed in Table 2.

TABLE 2

A summary amino acid residual numbers, theoretical sizes of the coding genes, theoretical molecular weight of the αPD-1 scFv, the αPD-1-iTEP fusion.

|  | Number of residues | Sizes of coding genes | Molecular weight/ kDa |
| --- | --- | --- | --- |
| αPD-1 scFv | 264 | 792 | 28.2 |
| αPD-1-iTEP fusion | 1084 | 3252 | 91.9 |

Figure 1C:
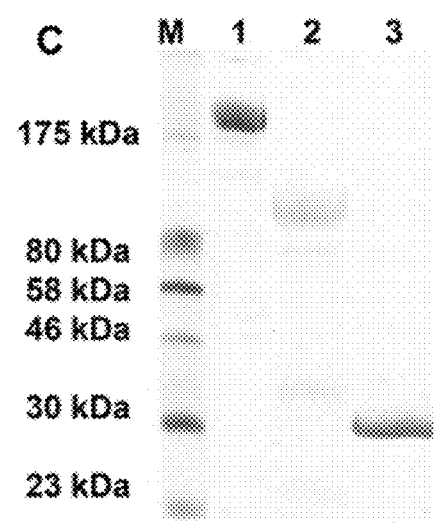

The SHuffle T7 *E. coli* strain was chosen to express the scFv and the fusion because the scFv has the two disulfide bonds that are important to its structure. The strain was engineered to express fully functional, disulfide bond-containing proteins (de Marco, A., Strategies for successful recombinant expression of disulfide bond-dependent proteins in *Escherichia coli*. *Microbial Cell Factories* 2009, 8, 26-26). An intact αPD-1 was also generated from RPM1-14 hybridoma inoculated mice. After these proteins were purified, SDS-PAGE was used to analyze the sizes and the purity of these proteins. On the SDS-PAGE gel, the intact αPD-1 showed a band migrating slower than the 175 kDa marker, indicating that the molecular weight of the intact αPD-1 is larger than 175 kDa. The SDS-PAGE results also confirmed the purity of the intact αPD-1 sample. It is noted that the intact αPD-1 sample was not reduced before being loaded on the gel so that the two heavy chains and two light chains of the antibody (IgG) migrated together. On the gel, the fusion sample showed a major band migrating slower than the 80 kDa marker; the scFv sample showed a major band migrating slightly faster than the 30 kDa marker (FIG. 1C). These migration results are consistent with their theoretical MWs, 91.9 kDa for the fusion and 28.2 kDa for the scFV, respectively (Table 2).

Materials. EL4 (ATCC® TIB-39™) cells were purchased from ATCC. Hybridoma RMP1-14 was used for αPD-1 production. DH5α competent *E. coli* cells were purchased from Thermo Fisher Scientific Inc. (Waltham, Mass.). SHuffle® T7 Competent *E. coli* cells were purchased from New England Biolabs (Ipswich, Mass.). Expression vector pET-25b(+) was purchased from EMD Millipore (Billerica, Mass.). Restriction endonucleases were purchased from New England Biolabs (Ipswich, Mass.). LB media were prepared using the standard formula. Cell culture media and supplements including RPMI-1640, Dulbecco's Modified Eagle Medium (DMEM), and fetal bovine serum (FBS) were purchased from Thermo Fisher Scientific Inc. (Waltham, Mass.). B6.129S7-Rag1$^{tm1Mom}$/J mice and NOD/ShiLtJ mice were purchased from the Jackson Laboratory.

Design and generation of the expression vectors for αPD-1 scFv and αPD-1-iTEP fusion. The αPD-1 hybridoma clone was sequenced using the variable domain sequencing service from GenScript. The sample submitted for sequencing was prepared following the protocol from GenScript (www.genscript.com/mAb-sequencing.html). To generate the αPD-1 scFv, the variable regions of the αPD-1 heavy ($V_H$) chain and the αPD-1 light chains ($V_L$) were connected by a linker, (GGGSG)$_4$ (SEQ ID NO: 40). The resultant scFv is NH$_2$-V$_H$-Linker-V$_L$—COOH. To facilitate the purification, six histidine residues were added to the N-terminus of the scFv. The coding gene of the scFv was synthesized by Thermo Fisher Scientific Inc. The gene was flanked by two BseRI restriction sites at each end to facilitate the ligation of the gene into the pET-25b(+) vector.

The αPD-1(scFv)-iTEP fusion was designed as illustrated in FIG. 1. The amphiphilic iTEP, NH$_2$-(GAGVPG)$_{70}$-(GVLPGVG)$_{56}$-(GC)$_4$, has a hydrophilic iTEP segment (GAGVPG)$_{70}$ (SEQ ID NO: 20) and a hydrophobic segment (GVLPGVG)$_{56}$ (Cho, S., et al., Immune-tolerant elastin-like polypeptides (iTEPs) and their application as CTL vaccine carriers. *Journal of drug targeting* 2016, 24 (4), 328-39) (SEQ ID NO: 21). The multiple cysteine residues at the hydrophobic end of the iTEP are crosslinked to the PD-1-iTEP fusions through disulfide bonds after the fusions self-assemble in a NP. The crosslinking is to stabilize the NP. The gene encoding the iTEP sequence was generated as previously described and inserted into the pET-25b(+) vector (Cho, S., et al., Immune-tolerant elastin-like polypeptides (iTEPs) and their application as CTL vaccine carriers. *Journal of drug targeting* 2016, 24 (4), 328-39). To generate the expression vector for the αPD-1-iTEP fusion, the gene for the αPD-1 scFv was first digested with BseRI and then ligated into the BseRI-digested iTEP in pET-25b(+).

Production and purification of αPD-1 scFv and αPD-1-iTEP fusion. The expression vectors of the scFv and the αPD-1-iTEP fusion were transformed into the SHuffle® T7 Competent *E. coli* cells for protein expression. For protein production, the transformed *E. coli* cells were first cultured in LB medium at 32° C. until the OD$_{600}$ of the medium reached 0.6 when. Then, IPTG was added into the culture medium at a final concentration of 0.5 mM. After that, the culture was continued at 16° C. overnight before the cells were harvested from the culture. To purify the scFv and the αPD-1-iTEP fusion from the harvested cells, the cells were lysed in PBS by sonication; the PBS contained 1 mM PMSF (Sigma-Aldrich, St. Louis, Mo.) for an inhibition of proteolysis. After the cell lysate was centrifuged at 20,000 g for 60 min at 4° C. to remove cell debris, the supernatant of the lysate was collected and loaded onto HisPur Ni-NTA spin columns (Thermo Fisher Scientific Inc). The scFv and the αPD-1-iTEP fusion were purified according to the protocol from Thermo Fisher Scientific Inc. The elute from the columns was dialyzed against PBS at 4° C. for 24 hours with three buffer changes. The purity and integrity of the collected proteins were examined by an SDS-PAGE analysis.

Production and purification of intact αPD-1. The αPD-1 was generated from ascetic fluid of the B6.129S7-Rag1$^{tm1/Mom}$/J mice that were inoculated by RMP-1-14 hybridoma cells (Yamazaki, T., et al., Blockade of B7-H1 on Macrophages Suppresses CD4+ T Cell Proliferation by Augmenting IFN-γ-Induced Nitric Oxide Production. *The Journal of Immunology* 2005, 175 (3), 1586-1592). The procedure of the inoculation and the fluid harvest were performed as previously reported (Noeman, S. A., et al., Growth of rat-mouse hybridomas in nude mice and nude rats. *Journal of immunological methods* 1982, 55 (3), 319-326). The αPD-1 was purified from the fluid according to a published protocol (Reik, L. M., et al., A simple, non-chromatographic purification procedure for monoclonal antibodies. Isolation of monoclonal antibodies against cytochrome P450 isozymes. *J Immunol Methods* 1987, 100 (1-2), 123-30). The yield was 30-50 mg αPD-1 per mouse.

Assembly of αPD-1 NP. The αPD-1-iTEP fusion was incubated at a high concentration (100 μM) at 37° C. for 20 min to promote the self-assembly of the fusion into the NP. Then, $H_2O_2$ was added into the sample to reach a final concentration of 0.3%, which was to oxidize cysteines in the fusion and promote the crosslink between the fusion inside the NP for 1 hr. Last, the fusion sample was dialyzed against PBS to remove $H_2O_2$. The same approach was applied to the amphiphilic iTEP used in the fusion when an iTEP NP was generated.

Size characterization of protein samples by dynamic light scattering (DLS). Intact aPD-1, the αPD-1-iTEP fusion and the amphiphilic iTEP used in the fusion were measured using the Malvern Zetasizer Nano (Malvern, Chester County, Pa.) at 37° C. The fusion and the iTEP samples were treated to assemble NPs before the measurement. All samples were measured at a concentration of 20 μM. Each sample was measured in triplicate. The instrument settings for the measurement are: material RI=1.59, material absorption=0.010, water dispersant RI=1.330, and viscosity=0.6864 cP. The default value, 4.65 mm, was used as the measurement position. The count rate, duration, and attenuator were automatically optimized by the program of Malvern Zetasizer Nano. Additionally, the αPD-1-iTEP fusion was measured at two concentrations (0.25 μM and 20 μM) at two temperatures (25° C. and 37° C.), and at two different redox status. The oxidization procedure was same as the described above. To reduce the sample, αPD-1-iTEP fusion was incubated with 20 mM TCEP overnight.

These studies demonstrate the generation of the first recombinant αPD-1, the αPD-1 scFv. A fusion protein of αPD-1 and iTEP as well as an αPD-1 NP were generated. These proteins may facilitate the improvement of αPD-1 immune therapy. For example, these proteins can be useful in the development of delivery systems to realize a cell-specific αPD-1 therapy, which is important to resolve the cause of αPD-1 toxicity.

Example 2: In Vitro Characterization of the αPD-1-iTEP Fusion

Figure 3A:
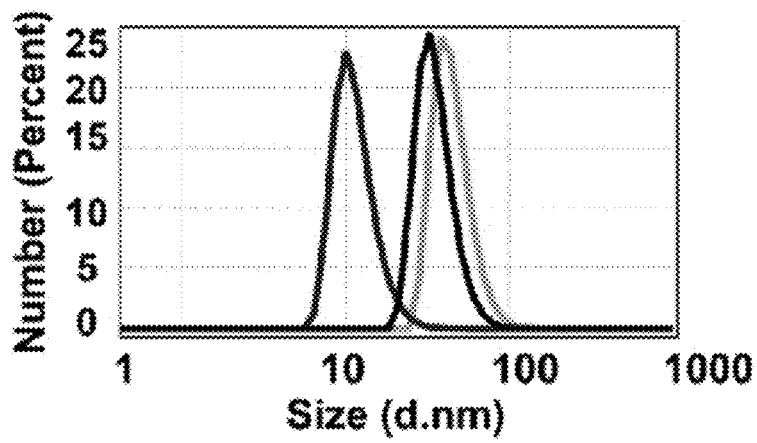
FIGS. 3A-C show in vitro characterization of the αPD-1-iTEP fusion.
Figure 3B:
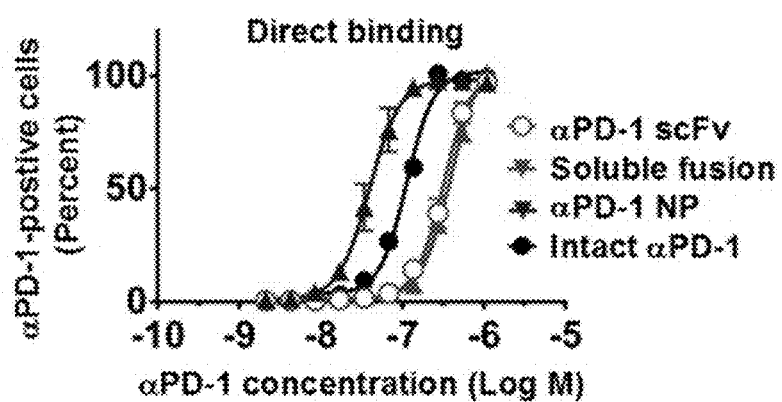
Figure 3C:
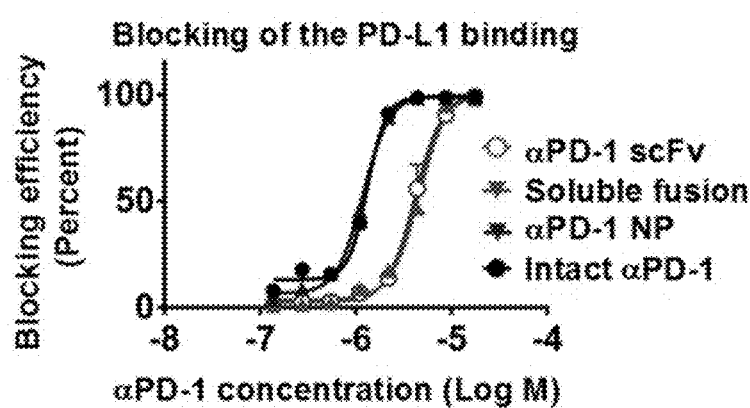

According to the DLS data, the fusion had a hydrodynamic diameter of 45.02±12.77 nm at 37° C. The amphiphilic iTEP used in the fusion had a hydrodynamic diameter of 35.62±10.16 nm (FIG. 3A). Thus, both the fusion and the iTEP appeared to form NPs. The NP form of the fusion was termed αPD-1 NP hereafter. αPD-1 NP has the capacity to multi-display αPD-1 on its surface as αPD-1 was located at the hydrophilic terminus of the fusion. 20 μM of each protein was used for the DLS analysis at 37° C. The included table lists hydrodynamic diameters of each protein. In contrast, intact αPD-1 had hydrodynamic diameters of 11.63±3.76 nm respectively (FIG. 3). The size of intact αPD-1 is consistent with reported sizes of natural, intact IgGs (Lavoisier, A., et al., Early developability screen of therapeutic antibody candidates using Taylor dispersion analysis and UV area imaging detection. *MAbs* 2015, 7 (1), 77-83). The hydrodynamic diameters of the αPD-1-iTEP fusion were measured at different temperatures, concentrations, and redox conditions. The results of these measurements are summarized in Table 3. The hydrodynamic diameters of the oxidized sample did not change significantly between two tested concentrations, 25 μM and 0.25 μM, suggesting that the NP assembled from the fusion was stabilized by oxidization and cross-linking. The diameters of the reduced sample were very different between the two tested concentrations, suggesting that the NP, without cross-linking through disulfide bonds, dissociated upon dilution. The above two conclusions are valid at the both temperatures used, 37° C. and 25° C. In addition, diameter values of the fusion did not change between the two temperatures.

Next, the binding of the αPD-1-iTEP fusion, in both its soluble form and its NP form, was examined with EL4 cells, a PD-1-positive cell line (Oestreich, K. J., et al., NFATc1 regulates PD-1 expression upon T cell activation. *Journal of immunology* (Baltimore, Md.: 1950) 2008, 181 (7), 4832-9). The cells were incubated with different concentrations of labeled sample before being analyzed by flow cytometry. According to the results of a direct binding assay (FIG. 3B), the soluble fusion and the scFv have comparable binding avidities to EL4 cells (EC50=0.40 μM, 95% CI 0.38~0.41 μM vs. EC50=0.32 μM, 95% CI 0.30~0.35 μM). Thus, adding the amphiphilic iTEP to the scFv did not significantly compromise the binding of the scFv to its antigens. However, the avidities of both the soluble fusion and the scFv are weaker than intact αPD-1 (EC50=0.11 μM, 95% CI 0.10~0.12 μM), suggesting that scFv loses some of its binding avidity as compared to its intact, parental antibody. Such loss is not uncommon for scFvs (Ahmad, Z. A., et al., scFv Antibody: Principles and Clinical Application. *Clinical and Developmental Immunology* 2012, 2012, 15). αPD-1 NP, in contrast, possesses a 4-times stronger avidity than intact αPD-1 (EC50=0.039 μM with 95% CI 0.036~0.043 μM). The stronger avidity may be attributed to a potentially multivalent display of the scFvs by the NP and a synergistic effect between the binding of first scFv on the NP and the binding of another scFv on the NP. This effect was described as a area of influence previously (Cuesta, A. M., et al., Multivalent antibodies: when design surpasses evolution. *Trends Biotechnol* 2010, 28 (7), 355-62).

How well the soluble αPD-1-iTEP fusion and αPD-1 NP inhibit the binding of PD-L1 to the PD-1-positive cells, the working mechanism of PD-1 immune checkpoint therapy (Hirano, F., et al., Blockade of B7-H1 and PD-1 by monoclonal antibodies potentiates cancer therapeutic immunity. *Cancer Res* 2005, 65 (3), 1089-96; Iwai, Y., et al., Involvement of PD-L1 on tumor cells in the escape from host immune system and tumor immunotherapy by PD-L1 blockade. *Proceedings of the National Academy of Sciences of the United States of America* 2002, 99 (19), 12293-7; and Deyev, S. M., et al., Multivalency: the hallmark of antibodies used for optimization of tumor targeting by design. *Bioessays* 2008, 30 (9), 904-18) was examined. To accomplish the examination, a PD-L1 binding inhibition assay was designed and used. Specifically, the fact that PD-L1-human Fc, a fusion protein of mouse PD-L1 fusion and human IgG Fc, bound with EL4 cells, and that the bound PD-L1-human Fc can be detected by an anti-human Fc antibody was taken advantage of. The blocking efficiencies were plotted against sample concentrations. Various concentrations of each listed αPD-1 sample were used to compete with the PD-L1-human Fc fusion (10 μg/mL) for binding to EL4 cells. The bound PD-L1 fusion was detected by an Alexa Fluor 488-labeled, anti-human Fc antibody. According to results of the binding inhibition assay (FIG. 3C), the soluble fusion and the scFv have the same inhibition capacity (EC50=4.59 µM with 95% CI 4.26~4.94 µM vs. EC50=4.16 µM with 95% CI 3.87~4.48 µM). However, both the soluble fusion and the scFv have a three times lower inhibition capacity than intact αPD-1 (EC50=1.32 µM with 95% CI 1.25~1.38 µM), a result consistent with the result of the direct binding assay. On the other hand, αPD-1 NP possesses a three times higher inhibition capacity than the soluble αPD-1-iTEP fusion, (EC50=1.19 µM with 95% CI 1.15~1.23 µM). Indeed, the inhibition capacity of the NP is slightly but significantly higher than intact αPD-1. Again, these results reinforce the advantage of multi-displaying antibodies by the NP.

TABLE 3

Hydrodynamic diameters of αPD-1-iTEP under different redox status, concentrations, and temperatures.

| Redox status | Concentration (µM) | Temperature | |
|---|---|---|---|
| | | 37° C. | 25° C. |
| Oxidized | 25 | 44.1 ± 12.8 | 38.3 ± 11.3 |
| | 0.25 | 43.9 ± 12.8 | 35.2 ± 10.7 |
| Reduced | 25 | 42.9 ± 12.3 | 39.2 ± 11.4 |
| | 0.25 | 8.9 ± 2.2* | 5.7 ± 1.5* |

Note:
The values of the hydrodynamic diameters are mean ± standard deviation.
*These small hydrodynamic diameter values suggest that sample does not have a NP structure.

The direct binding assay. The assay was used to examine the binding between αPD-1 samples and PD-1-positive EL4 cells. The αPD-1 samples include soluble αPD-1-iTEP fusion, αPD-1 NP, the αPD-1 scFv, and intact αPD-1. First, all αPD-1 samples were labelled with Alexa Fluor 647. Next, each of these samples was incubated with 1 million of EL4 cells on ice for 30 min. The fraction of EL4 cells in each incubation mixture that were Alexa Fluor 647-positive was quantified by flow cytometry on a BD FACSCANTO II (BD Biosciences, San Jose, Calif.). The percentages were plotted against concentration for each αPD-1 sample. EC50 and the 95% confidence interval (95% CI) of the EC50 were generated for each sample by fitting the curve of the sample to a built-in, Sigmoidal dose-response model of GraphPad V5.0.

The blocking assay of PD-L1 binding. The blocking of the PD-L1 binding to EL4 cells was determined through a competition binding assay. In this assay, soluble αPD-1-iTEP fusion, αPD-1 NP, the αPD-1 scFv, and intact αPD-1 were paired and competed with a PD-L1 sample (PD-L1-human Fc fusion, R&D Systems Inc. Minneapolis, Minn., USA), respectively. Specifically, each of the above αPD-1 samples was serially diluted and incubated with 1 million EL4 cells in 5 ml test tubes on ice for 30 min. Next, the PD-L1 fusion was added into the incubation mixtures at the final concentration of 10 µg/mL; the mixtures were kept on ice for additional 30 min. Then, an Alexa Fluor 488-labeled, goat-anti-human Fc antibody (Thermo Fisher Scientific Inc.) was added into the mixtures to stain the PD-L1 fusion; the mixtures were kept on ice for another 30 min. After the incubation, unbound proteins were washed away with a FACS buffer, PBS with 1% FBS; the EL4 cells in the mixtures were collected. The fractions of EL4 cells that were Alexa Fluor 488-positive were quantified using flow cytometry on a BD FACSCANTO II flow cytometer (BD Biosciences, San Jose, Calif.). In two separate experiments, EL4 cells were treated with an 100% blocking condition (an incubation with the anti-human Fc antibody) and a 0% blocking condition (an incubation with the anti-human Fc antibody plus the PD-L1 fusion); the fractions of Alexa Fluor 488-positive EL4 cells after these two treatments were quantified using flow cytometry. Lastly, all fractions values of Alexa Fluor 488-positive EL4 cells that resulted from the above αPD-1 treatments were transformed into blocking efficiencies (%) through normalization of these values against the fraction values of 100% and 0% blocking. The blocking efficiencies were plotted against the concentrations of the corresponding samples. EC50 and its 95% CI were generated for each sample by fitting the curve of the sample to a Sigmoidal dose-response model using GraphPad V5.0.

As mentioned above, an scFv of αPD-1 and a NP that delivers αPD-1 has been successfully generated. These studies also show that αPD-1 on the NP carrier is able to block the PD-1 immune checkpoint.

The finding that αPD-1 NP effectively blocks the PD-1 checkpoint is a success that underscores the importance of multivalency in interactions between antibodies and the cells expressing the corresponding antigens. The αPD-1 scFv has a reduced avidity to PD-1-positive cell and a weaker inhibition on the PD-L1 binding to the cells as compared to intact αPD-1. A similar deficiency has been reported for scFv previously (Cuesta, A. M., et al., Multivalent antibodies: when design surpasses evolution. *Trends Biotechnol* 2010, 28 (7), 355-62; and Deyev, S. M., et al., Multivalency: the hallmark of antibodies used for optimization of tumor targeting by design. *Bioessays* 2008, 30 (9), 904-18). The possible reasons of the deficiency include that (1) scFv is monovalent while intact αPD-1 is divalent; and (2) scFv may have a lower thermodynamic stability than αPD-1, which comprises its binding with its antigens[32]. The deficiency was, nevertheless, resolved by the αPD-1 NP. The NP indeed showed stronger binding to PD-1-positive cells and greater PD-L1 binding inhibition than intact αPD-1, which clearly demonstrated the impact of multivalency as the NP can display multiple scFvs on its surface. It is notable that the EC50 of the NP is about three times smaller than that of intact αPD-1 according to the direct binding results; however, the EC50 of the NP is slightly lower than that of intact αPD-1 according to the PD-L1 binding inhibition results. This apparent discrepancy may be due to the different methodologies of the two experiments. Another plausible reason for the discrepancy is that not all of the αPD-1 scFVs on the NP that were bound with PD-1-positive cells actually engaged with PD-1 on the cell surface. These unengaged scFvs, therefore, were able to inhibit the PD-L1 binding. The existence of these "unengaged" scFvs may be caused by a steric effect between scFvs on the NP and accessibility of adjacent PD-1 on the cells.

In summary, an αPD-1 NP was generated that is functional and possesses the advantage of multivalency. This NP could serve as a foundation to develop carriers for αPD-1 and other immune checkpoint inhibitors that target the inhibitors to a specific subpopulation of PD-1-positive cells.

Example 3: In Vivo Characterization of the αPD-1-iTEP Fusion

αPD-1 exacerbates diabetes development in non-obese diabetic (NOD)/ShiLtJ mice because it blocks the PD-1 immune checkpoint and worsens the autoimmune disorders of the mice (Ansari, M. J. I., et al., The Programmed Death-1 (PD-1) Pathway Regulates Autoimmune Diabetes in Nonobese Diabetic (NOD) Mice. *The Journal of Experimental Medicine* 2003, 198 (1), 63-69). This effect was used to examine whether the αPD-1-iTEP fusion is functional in vivo (FIG. 4A) and diabetes-free survival was utilized as an outcome to evaluate the effect (FIG. 4B). Blood glucose concentrations were monitored up to 30 days after the initial treatment. The diabetes-free survival data were analyzed by the Kaplan-Meier method. According to the survival data, both the soluble αPD-1-iTEP fusion and αPD-1 NP significantly accelerated diabetes development in NOD mice as compared to PBS (median survival time, Log rank test, p=0.049 and p=0.049). The median diabetes-free survival time of the soluble fusion- and the αPD-1 NP-treated mice are 16 days and 21 days, respectively. In contrast, none of the PBS-treated mice developed diabetes before all these mice were censored on day 30 after the treatment initiation. Further, the effect of the soluble fusion and αPD-1 NP on diabetes development are not statistically different from intact αPD-1 (P=0.771 and p=0.900). The median diabetes-free survival time for intact αPD-1-treated mice is 19 days. Last, the effect of the soluble fusion and αPD-1 NP are not different (p=0.775). Together, these results suggest that the αPD-1-iTEP fusion, either in its soluble form or in its NP form, is functional in vivo and is as effective as intact αPD-1 in blocking the PD-1 immune checkpoint and promoting diabetes in NOD mice.

Diabetes exacerbation. Ten-week-old female NOD/ShiLtJ mice were separated into four groups. Each group of the mice was intraperitoneally injected five times with one of the four samples: soluble αPD-1-iTEP fusion, αPD-1 NP, intact αPD-1, or PBS. The first dose was 0.5 mg αPD-1 equivalent per mouse on day 0 except for the PBS group; the remaining four doses were 0.25 mg αPD-1 equivalent per mouse on day 2, 4, 6, and 8. Blood was drawn from the tails of these mice every other day from day 0. Glucose concentrations in these blood samples were measured by a OneTouch UltraMini meter (LifeScan, Inc., Milpitas, Calif.). The sampling and monitoring were continued for every mouse until that mouse was confirmed for diabetes. The criterion of diabetes is that blood glucose concentration reached or surpassed 250 mg/deciliter (dL) for three consecutive measurements (Ansari, M. J. I., et al., The Programmed Death-1 (PD-1) Pathway Regulates Autoimmune Diabetes in Nonobese Diabetic (NOD) Mice. *The Journal of Experimental Medicine* 2003, 198 (1), 63-69). The first date that confirmed diabetes was observed was recorded and used to calculate diabetes-free survival days. Diabetes-free survival was analyzed by the Kaplan-Meier method, and the median survival of each treatment group was compared using the Log rank test with GraphPad V5.0.

Example 4: Development of Tetramer-Guided αPD-1 NPs to Target Melanoma-Reactive CTLs The targeted αPD-1 therapy will use a novel, dual nanoparticle (NP) approach. The first NP will be guided by an MHC class I tetramer and hence target αPD-1 to melanoma-reactive cytotoxic T lymphocytes (CTLs) (Gubin M M, et al. Checkpoint blockade cancer immunotherapy targets tumour-specific mutant antigens. Nature. 2014; 515(7528): 577-81) while directing αPD-1 away from the PD-1 positive cells that cause the toxicity (FIG. 5, right side, showing the mechanism) (Frebel H, et al. The risks of targeting co-inhibitory pathways to modulate pathogen-directed T cell responses. Trends in immunology. 2013; 34(5):193-9; and Kochupurakkal N M, et al. Blockade of the programmed death-1 (PD1) pathway undermines potent genetic protection from type 1 diabetes. PloS one. 2014; 9(2)). The higher avidity is due to interactions between the tetramer and T cell receptor (TCR) on the CTLs. In contrast, free αPD-1 does not have this property. This NP will permit a melanoma-reactive CTL-specific PD-1 blockade. The second NP will be a multi-functional melanoma CTL vaccine NP that enhances the CTL-specific blockade by amplifying the CTLs. The specific blockade will reduce the toxicity and boost the efficacy of αPD-1, and lead to the resolution of the aforementioned deficiencies. Therefore, targeted αPD-1 therapy will have improved efficacy and reduced toxicity compared to the current αPD-1 therapy.

A mixed-micelle approach (Bae Y, et al. Intelligent polymeric micelles from functional poly(ethylene glycol)-poly (amino acid) block copolymers. Advanced Drug Delivery Reviews. 2009; 61(10):768-84) will be used to generate tetramer-guided αPD-1 NPs displaying both αPD-1 and tetramers that recognize melanoma-reactive CTLs. The NPs should have a higher avidity to CTLs versus other PD-1 positive cells. Next, the NPs will be examined to test whether they have improved efficacy and reduced toxicity in the B16 melanoma model and the experimental autoimmune encephalomyelitis (EAE) model, respectively.

Disclosed herein are targeted αPD-1 therapies that specifically block the PD-1 checkpoint of melanoma-reactive CTLs. This therapy may address the above deficiencies because the indiscriminate blockade of the checkpoint is a cause of these deficiencies. Intrinsically, the PD-1 checkpoint plays a role in protecting tumors from immune elimination (Topalian S L, et al. Targeting the PD-1/B7-H1(PD-L1) pathway to activate anti-tumor immunity. Current Opinion in Immunology. 2012; 24(2):207-12) and also maintains immune stasis and prevents autoimmune destruction in healthy tissues, such as pancreatic islets (Pentcheva-Hoang T, et al. Negative regulators of T-cell activation: potential targets for therapeutic intervention in cancer, autoimmune disease, and persistent infections. Immunological reviews. 2009; 229(1):67-87). Therefore, the indiscriminate blockade of the checkpoint, while boosting anti-cancer immunity, has two adverse consequences that contribute to the deficiencies. First, the blockade causes autoimmune toxicity in normal tissues (Hamid O, et al. Safety and tumor responses with lambrolizumab (anti-PD-1) in melanoma. The New England Journal of Medicine. 2013; 369(2):134-44; Topalian S L, et al. Safety, activity, and immune correlates of anti-PD-1 antibody in cancer. The New England Journal of Medicine. 2012; 366(26):2443-54; Gelao L, et al. Immune checkpoint blockade in cancer treatment: a double-edged sword cross-targeting the host as an "innocent bystander". Toxins. 2014; 6(3):914-33; and Nishino M, et al. Anti-PD-1-Related Pneumonitis during Cancer Immunotherapy. New England Journal of Medicine. 2015; 373(3): 288-90); and second, the blockade wastes αPD-1 in melanoma treatment-unrelated interactions and lowers its access to melanoma-reactive immune cells that require αPD-1 to block their PD-1 checkpoint. This is the case when the administered mAb does not saturate all PD-1 positive cells. The lowered access likely weakens the potency of the mAb. In contrast, the targeted αPD-1 therapy permits CTL-specific blockade by using guided NPs to target αPD-1 to melanoma-reactive CTLs, the primary tumor-killing cells that require the PD-1 blockade (Chen Daniel S, et al. Oncology Meets Immunology: The Cancer-Immunity Cycle. Immunity. 2013; 39(1):1-10; Chapon M, et al. Progressive upregulation of PD-1 in primary and metastatic melanomas associated with blunted TCR signaling in infiltrating T lymphocytes. The Journal of investigative dermatology. 2011; 131(6):1300-7; and Tumeh P C, et al. PD-1 blockade induces responses by inhibiting adaptive immune resistance. Nature. 2014; 515(7528):568-71), and uses vaccine NPs to amplify these CTLs. This way the targeted αPD-1 therapy may eliminate the cause of the deficiencies and benefit those patients who suffered from the deficiencies.

For patients who do not respond to the current αPD-1 therapy, the targeted αPD-1 therapy will also provide a benefit. The targeted αPD-1 therapy may strengthen the existing, anti-melanoma immunity in non-responding patients and enable them to respond to therapy. Several recent reports showed that the non-responders have fewer neo tumor antigens than the responders (Le D T, et al. PD-1 Blockade in Tumors with Mismatch-Repair Deficiency. New England Journal of Medicine. 2015; 372(26):2509-20; Rizvi N A, et al. Mutational landscape determines sensitivity to PD-1 blockade in non-small cell lung cancer. Science. 2015; 348(6230):124-8; Hugo W, et al. Genomic and Transcriptomic Features of Response to Anti-PD-1 Therapy in Metastatic Melanoma. *Cell.* 2016; 165(1):35-44). Since tumor antigens in non-responders cannot be increased, one way to facilitate a response to the αPD-1 therapy is to leverage their existing tumor antigens and enhance their anti-melanoma immunity based on these antigens. Based on this premise, the targeted αPD-1 therapy will have provide an improved response rate among the non-responders because it amplifies melanoma-reactive CTLs that recognize and eliminate tumor cells and it reinforces the tumor-killing function of the CTLs by concentrating αPD-1 to the CTLs. Support for this idea is that a greater extent of T cell clonal expansions (amplification of a small number of CTL clones) was observed in the responders than the non-responders after PD-1 therapy (Tumeh P C, et al. PD-1 blockade induces responses by inhibiting adaptive immune resistance. Nature. 2014; 515(7528):568-71). The targeted therapy with reduced toxicity also allows the patients to take higher doses of αPD-1 for a longer duration, which may permit the non-responders to respond to the therapy. Indeed, it was reported that a high dose of αPD-1 (10 mg/kg per two weeks) resulted in a greater patient response rate when compared with a low dose (2 mg/kg per three weeks), 56% vs 14% (Hamid O, et al. Safety and tumor responses with lambrolizumab (anti-PD-1) in melanoma. The New England journal of medicine. 2013; 369(2):134-44). For patients who suffer high-grade adverse effects from the current αPD-1 therapy as well as the side effects of the current αPD-1 toxicity management methods, the targeted therapy with reduced toxicity may also benefit them. The targeted therapy will be less likely to cause high-grade adverse effects. The therapy addresses the cause of the toxicity; patients taking this therapy do not have to experience non-specific immune deficiency or serious infections that are associated with the current toxicity management methods. As an outcome, no or fewer patients will need to discontinue the therapy either due to the toxicity or the toxicity management. For melanoma patients with pre-existing autoimmune disorders and chronic infections, the targeted αPD-1 therapy will be applicable to them because the therapy has reduced toxicity. Reduced toxicity is expected because guided αPD-1 NPs "divert" αPD-1 away from those PD-1-positive cells that cause autoimmune toxicity, and amplified melanoma-reactive CTLs by vaccine NPs will also "draw" αPD-1 away from the toxicity-causing cells.

Together, the targeted αPD-1 therapy may benefit considerably more advanced melanoma patients than the current PD-1 therapy which has a response rate between 17-37%.

A tetramer-guided αPD-1 NP was generated that preferentially delivers αPD-1 to a specific clone of CTLs. αPD-1 on this NP is functional. In addition, an αPD-1-iTEP fusion is functional in vivo. These data suggest it is feasible to use NPs to target αPD-1 to melanoma-reactive CTLs.

A B16 tumor model was established and proved that melanoma vaccines and αPD-1 are effective in this model.

The studies described herein will answer whether a targeted αPD-1 therapy outperforms an indiscriminate αPD-1 therapy. Currently, αPD-1 activates all PD-1-positive cells. However, it is unclear whether such indiscriminate activation is necessary. In contrast, the targeted αPD-1 therapy activates a few defined CTL clones that are possibly the most important for eliminating melanoma. If the therapy described herein delivers comparable or better efficacy than the current therapy, it suggests that the αPD-1 therapy does not need to activate immune cells as broadly and indiscriminately as it does now. Instead, the αPD-1 therapy can be improved from a completely different direction, delivering αPD-1 to those immune cells that are the most relevant for tumor eradication. This therapeutic improvement idea is practical because the trend that more and more melanoma-reactive immune cell clones are identified amid the research advancement of precision medicine and immuno genomics (Gubin M M, et al. Checkpoint blockade cancer immunotherapy targets tumour-specific mutant antigens. Nature. 2014; 515(7528):577-81; Robbins P F, et al. Mining exomic sequencing data to identify mutated antigens recognized by adoptively transferred tumor-reactive T cells. Nature medicine. 2013; 19(6):747-52; and van Rooij N, et al. Tumor Exome Analysis Reveals Neoantigen-Specific T-Cell Reactivity in an Ipilimumab-Responsive Melanoma. Journal of Clinical Oncology. 2013; 31(32):e439-e42).

Described herein is also a strategy to redistribute drugs that bind with cell surface molecules. It is challenging to use a carrier to concentrate αPD-1 to a subpopulation of PD-1 positive cells since αPD-1 binds with all PD-1-positive cells, and αPD-1 has to be exposed on the surface of the carrier to execute its function. To meet this challenge, a NP carrier will be developed that has a high tetramer-to-αPD-1 ratio on its surface. This is designed this way because avidities between tetramers and their cognate TCRs (<=10 nM) are comparable to two reported avidities between αPD-1 and PD-1 (3 nM, 20 nM) (Wang C, et al. In Vitro Characterization of the Anti-PD-1 Antibody Nivolumab, BMS-936558, and In Vivo Toxicology in Non-Human Primates. Cancer Immunology Research. 2014; 2(9):846-56; and Kim J K, et al. Prospects for targeting PD-1 and PD-L1 in various tumor types. Oncology Journal, Supplements. 2014), and hence a high tetramer-to-αPD-1 ratio should result in a NP that has a higher avidity to melanoma-reactive CTLs cognate to the tetramers, compared to the intrinsic avidities between αPD-1 and PD-1-positive cells. Indeed, FIG. 7B validates this redistribution strategy.

A targeted αPD-1 therapy that activates specific clones of melanoma-reactive CTLs will be developed. This targeted therapy is mechanistically different from the current non-specific αPD-1 therapy. This development may shift the paradigm of the αPD-1 therapy regarding whether a broad, nonspecific immune checkpoint blockade is necessary for the efficacy of the therapy.

The experiments described herein were accomplished in two phases: (1) generating and characterizing a prototype, guided αPD-1 NP using the SIINFEKL (SEQ ID NO: 41) peptide-restricted tetramer and (2) based on this prototype NP, generating guided NPs that target melanoma-reactive CTLs and evaluating the efficacy and toxicity of the NPs. The SIINFEKL (SEQ ID NO: 41) tetramer was used as a model because it is easy to obtain a large amount of CTLs cognate to this tetramer (OT-I CTLs) Hogquist K A, et al. T cell receptor antagonist peptides induce positive selection. Cell. 1994; 76(1):17-27), and because there are many immunological tools matching this tetramer.

The design of tetramer-guided αPD-1 NPs. The NPs are assembled from two iTEP fusions, iTEP-αPD-1 and iTEP-tetramer, using a physically mixed-micelle approach as illustrated in FIG. 6 (Bae Y, et al. Intelligent polymeric micelles from functional poly(ethylene glycol)-poly(amino acid) block copolymers. Advanced Drug Delivery Reviews. 2009; 61(10):768-84). iTEP-αPD-1 is a recombinant polypeptide. The iTEP-tetramer is generated via two steps: first, an iTEP-streptavidin fusion is generated as a recombinant polypeptide (Schultz J, et al. A Tetravalent Single-chain Antibody-Streptavidin Fusion Protein for Pretargeted Lymphoma Therapy. Cancer Research. 2000; 60(23):6663-9); second, the biotinylated MHC class I monomers (H2-Kb/SIINFEKL or ones containing melanoma-related epitopes) are mixed with the iTEP-streptavidin fusion to assemble the iTEP-tetramer fusion. An advantage of the mixed-micelle approach is that it allows for easy control of the ratio between the tetramers and αPD-1 on the guided NPs.

C57BL/6 (B6) mice as an animal model. The rationale for choosing this animal is: (1) the B16F10 tumor (abbreviation as B16 tumor hereafter) is syngeneic with B6 mice; the B16 tumor responds modestly to αPD-1 therapy (Holmgaard R B, et al. Indoleamine 2,3-dioxygenase is a critical resistance mechanism in antitumor T cell immunotherapy targeting CTLA-4. The Journal of experimental medicine. 2013; 210(7):1389-402; and Li B, et al. Anti-programmed death-1 synergizes with granulocyte macrophage colony-stimulating factor—secreting tumor cell immunotherapy providing therapeutic benefit to mice with established tumors. Clinical cancer research: an official journal of the American Association for Cancer Research. 2009; 15(5):1623-34), thus, this model can be used to reveal any efficacy improvement of the therapy; and (2) the B6-based EAE model is a well-established autoimmune model (Tsunoda I, et al. Contrasting Roles for Axonal Degeneration in an Autoimmune versus Viral Model of Multiple Sclerosis: When Can Axonal Injury Be Beneficial? The American Journal of Pathology. 2007; 170(1):214-26); the indiscriminate PD-1 blockade exacerbates EAE development (Salama A D, et al. Critical role of the programmed death-1 (PD-1) pathway in regulation of experimental autoimmune encephalomyelitis. The Journal of experimental medicine. 2003; 198(1):71-8; Zhu B, et al. Differential role of programmed death-ligand 1 [corrected] and programmed death-ligand 2 [corrected] in regulating the susceptibility and chronic progression of experimental autoimmune encephalomyelitis. Journal of immunology. 2006; 176(6):3480-9), which serves as a biomarker of the αPD-1 toxicity.

The choice of three melanoma-related tetramers that contain three peptide epitopes derived from three B16 tumor antigens, respectively. The epitopes are KVPRNQDWL (SEQ ID NO: 42) from glycoprotein 100 (gp100), TWHRYHLL (SEQ ID NO: 43) from tyrosinase-related protein-1 (Trp-1), and SVYDFFVWL (SEQ ID NO: 44) from tyrosinase-related protein-2 (Trp-2) (Overwijk W W, et al. gp100/pmel 17 is a murine tumor rejection antigen: induction of "self"-reactive, tumoricidal T cells using high-affinity, altered peptide ligand. The Journal of experimental medicine. 1998; 188(2):277-86; Dyall R, et al. Heteroclitic immunization induces tumor immunity. The Journal of experimental medicine. 1998; 188(9):1553-61; and Bloom M B, et al. Identification of tyrosinase-related protein 2 as a tumor rejection antigen for the B16 melanoma. The Journal of experimental medicine. 1997; 185(3):453-9). The epitopes bind with MHC class I alleles of B6 mice (Li B, et al. Anti-programmed death-1 synergizes with granulocyte macrophage colony-stimulating factor—secreting tumor cell immunotherapy providing therapeutic benefit to mice with established tumors. Clinical cancer research: an official journal of the American Association for Cancer Research. 2009; 15(5):1623-34). The CTL clones that are cognate to these three tetramers are important to inhibit the growth and metastasis of B16 tumors (Mansour M, et al. Therapy of established B16-F10 melanoma tumors by a single vaccination of CTL/T helper peptides in VacciMax. Journal of translational medicine. 2007; 5:20); therefore, it is plausible to target αPD-1 to these CTL clones. The human homologous proteins of these three antigens are important as immunotherapy of human melanoma; thus, results of these three antigens are easy to clinically translate (Phan G Q, et al. Immunization of patients with metastatic melanoma using both class I- and class II-restricted peptides from melanoma-associated antigens. J Immunother. 2003; 26(4): 349-56).

Results. A SIINFEKL (SEQ ID NO: 41) tetramer-guided αPD-1 NP has been generated (FIG. 7A). FIG. 7B shows that this NP is able to target αPD-1 to a specific clone of CTLs (the targeting efficiency is 37.3 at the 4 μg αPD-1/ml concentration). In contrast, unguided αPD-1 NP and free αPD-1 labeled fewer OT-I cells, indicating that OT-I cells expressed less PD-1 than OT-II cells. Targeting efficiency of the guided αPD-1 NP, which is defined as the OT-I:OT-II ratio of guided NPs divided by the OT-I:OT-II ratio of free αPD-1, is 37.3 when 4 μg/ml of αPD-1 was used. Thus, the guided NP very efficiently targeted αPD-1 to its cognate cells. FIG. 7C shows that αPD-1 on the NP is fully functional in vitro. FIG. 8 shows that αPD-1 in the iTEP-αPD-1 fusion is also fully functional in vivo. Together these data support the feasibility of using tetramer-guided αPD-1 NPs to target αPD-1 to melanoma-reactive CTLs. Further, in the relevant B16 tumor model, the effects of both melanoma vaccines and free αPD-1 were observed (FIG. 9). The ELISPOT data showed that the vaccine induced CTL responses in the tumored mice and αPD-1 tripled the responses (t-test, N=3).

Generate iTEP-tetramer (SIINFEKL; (SEQ ID NO: 41)) and iTEP-αPD-1 fusions. The iTEP-αPD-1 and the iTEP-streptavidin fusions were generated as recombinant proteins from *E. coli*. Both fusions were based on one amphiphilic diblock iTEP ($NH_2$-iTEP$_{B70}$-iTEP$_{A56}$—COOH) with a CysTag and a HisTag. The sequences of the two fusions are illustrated in the scheme below. The CysTag is included in both fusions because an inter-fusion molecule with disulfide bonds will be used to stabilize the micelle-like iTEP NPs (Zhao P, et al. An iTEP-salinomycin nanoparticle that specifically and effectively inhibits metastases of 4T1 orthotopic breast tumors. Biomaterials. 2016; 93:1-9). The HisTag is included for purification purposes. The fusions will be coded by their corresponding genes (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78). To assemble the SIINFEKL (SEQ ID NO: 41) tetramers, iTEP-streptavidin was mixed with the biotinylated H2-Kb/SIINFEKL monomer at a 1-to-4 ratio.

iTEP-αPD-1 fusion: $NH_2$-HisTag[$H_6$]-Linker[(GGGSG)]-αPD-1(scFV)-iTEP$_{B70}$[(GAGVPG)$_{70}$]-iTEP$_{A56}$ [(GVLPGVG)$_{56}$]-CysTag [(GC)$_4$]—COOH iTEP-streptavidin fusion: $NH_2$-HisTag-Streptavidin-Linker-iTEP$_{B70}$-iTEP$_{A56}$-CysTag—COOH Form andcharacterize the tetramer-guided αPD-1 NP. First, the iTEP-αPD-1 and iTEP-tetramer were mixed at a 1-to-10 ratio. Dynamic light scattering (DLS) analysis was used to confirm that these fusions form the NP. It is known that αPD-1 may bind with melanoma-reactive CTLs in lymph organs, blood, or tumors and exert their function according to preclinical and clinical data of αPD-1 (Topalian S L, et al. Safety, activity, and immune correlates of anti-PD-1 antibody in cancer. The New England Journal of Medicine. 2012; 366(26):2443-54; Curran M A, et al. PD-1 and CTLA-4 combination blockade expands infiltrating T cells and reduces regulatory T and myeloid cells within B16 melanoma tumors. Proceedings of the National Academy of Sciences of the United States of America. 2010; 107(9): 4275-80; and Li B, et al. Anti-programmed death-1 synergizes with granulocyte macrophage colony-stimulating factor—secreting tumor cell immunotherapy providing therapeutic benefit to mice with established tumors. Clinical cancer research: an official journal of the American Association for Cancer Research. 2009; 15(5):1623-34). Thus, it is not expected that the size of the NP to be a factor in this delivery strategy.

Second, the disulfide bonds were oxidized between fusion molecules to stabilize the NP using 0.3% $H_2O_2$ after the NP structure of the mixed iTEP fusions were confirmed. The disulfide-bonded NP is expected to be stable even after the NP sample is serially diluted. The NP structure was verified by DLS analysis with a size of 56.5±14.2 nm (FIG. 7A) and will be further investigated by a pyrene-based critical micelle concentration assay (Dreher M R, et al. Temperature triggered self-assembly of polypeptides into multivalent spherical micelles. Journal of the American Chemical Society. 2008; 130(2):687-94).

Third, the αPD-1-to-tetramer ratio in the NP is expected to be 1 to 10. To verify this prediction, the iTEP-tetramer and iTEP-αPD-1 fusions will be pre-labeled with Alexa-488 and Alexa-610, respectively, and then the labeled fusions will be used to assemble the NP. The tetramer-to-αPD-1 ratio will be estimated using the intensity ratio of the Alexa-488 and Alexa-610 emissions.

Examine the avidity of the guided αPD-1 NP to OT-I CTLs. The avidity between guided αPD-1 and OT-I CTLs will be determined as previously reported (Holmberg K, et al. TCR binding kinetics measured with MHC class I tetramers reveal a positive selecting peptide with relatively high affinity for TCR. Journal of immunology. 2003; 171 (5):2427-34; and Savage P A, et al. A Kinetic Basis For T Cell Receptor Repertoire Selection during an Immune Response. Immunity. 1999; 10(4):485-92). The avidity is expected to be higher than control avidities between free αPD-1 and OT-I CTLs, unguided αPD-1 and OT-I CTLs, as well as guided αPD-1 and active OT-II splenocytes (PD-1 positive but not cognate to the tetramer, from OT-II mice) (Barnden M J, et al. Defective TCR expression in transgenic mice constructed using cDNA-based [agr]- and [bgr]-chain genes under the control of heterologous regulatory elements. Immunol Cell Biol. 1998; 76(1):34-40). Alternatively, the guided αPD-1's avidities can be compared to OT-I CTLs and OT-II splenocytes indirectly using a preferential binding assay as described in FIG. 7B.

TABLE 4

The PD-L1 binding inhibition assay. All OT-I cells are stimulated by αCD3 to express PD-1 and then incubated with labeled PD-L1 and different forms of αPD-1.

| Group | αPD-1 | Expected binding of PD-L1 to OT-I CTL |
|---|---|---|
| 1 | Guided αPD-1 | ++ |
| 2 | Free αPD-1 | ++ |
| 3 | Unguided αPD-1 | ++ |
| 4 | Empty NP | +++++ |
| 5 | None | +++++ |

Examine the PD-1 checkpoint blockade function by guided αPD-1 NP in vitro. αPD-1 blocks the PD-1 immune checkpoint by inhibiting the binding between PD-L1 and PD-1 (Hirano F, et al. Blockade of B7-H1 and PD-1 by monoclonal antibodies potentiates cancer therapeutic immunity. Cancer Res. 2005; 65(3):1089-96; and Iwai Y, et al. Involvement of PD-L1 on tumor cells in the escape from host immune system and tumor immunotherapy by PD-L1 blockade. Proceedings of the National Academy of Sciences of the United States of America. 2002; 99(19):12293-7). A PD-L1 binding inhibition assay will be used to examine the functionality of αPD-1 on the guided αPD-1 NP, a method used to produce the data in FIG. 7B. Table 4 describes experimental treatments and the expected binding results of each treatment.

Examine the internalization of guided αPD-1 NPs by its cognate CTLs (target cells). The internalization kinetics of guided αPD-1 NPs and free αPD-1 will be compared using an acid dissociation method (Vainshtein I, et al. Quantitative measurement of the target-mediated internalization kinetics of biopharmaceuticals. Pharm Res. 2015; 32(1):286-99). Specifically, the Alexa-647-prelabled NPs or the Alexa-647-prelabled αPD-1 will be incubated with OT-I lymphocytes (PD-1-positive) for 0, 2, or 4 hr at 4° C. and 37° C. The 4° C. treatments serve as no-internalization controls. After the incubations, the surface bound NPs or αPD-1 will be removed by 0.2 M acetic acid, 0.5 M NaCl (pH2.5). The internalized NPs or αPD-1 will be quantified by flow cytometry. Internalization kinetics plots will be generated using percentage values of internalized samples over time. The internalization results will also be independently confirmed using confocal imaging (Vainshtein I, et al. Quantitative measurement of the target-mediated internalization kinetics of biopharmaceuticals. Pharm Res. 2015; 32(1): 286-99). The internalizations of the NP and free αPD-1 are expected to not be different or the difference will not be significant enough to affect the function of αPD-1 on the NPs because both the NP and free αPD-1 inhibit the PD-L1 binding equally effectively (FIG. 7B).

Construct melanoma tetramer guided αPD-1 NPs. Three melanoma-related tetramers, gp100, Trp-1, and Trp-2 will be used to generate three new NPs that deliver αPD-1. DLS will be to confirm that the new NPs do form. The new NPs will also be stabilized by using disulfide bonds and the tetramer-to-αPD-1 ratios of the new NPs will be determined.

Measureavidities of melanoma tetramer-guided αPD-1 with their cognate CTLs. The method as described herein will be used with the difference being the source of CTLs. To generate the CTLs, gp100, Trp-1 and Trp-1 epitopes will be used to elicit CTL responses in naive mice (100 µg vaccine equivalent per type of vaccine), respectively, and then amplify these CTLs in vitro. The protocol to amplify CTLs from B6 mouse splenocytes (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78) has been previously described. It is expected that the avidity between guided αPD-1 and their cognate CTLs will be higher than the control avidities between guided αPD-1 and OT-II splenocytes.

Determine whether guided αPD-1 NPs has reduced autoimmune toxicity as compared to free αPD-1. The EAE exacerbation effect of αPD-1 will be used as an indicator of the toxicity. Experimentally, EAE will be first induced and three clones of cognate CTLs of the guided NPs in B6 mice will be concurrently amplified. Then, these mice will be treated with guided αPD-1 NPs (a mixture of three tetramer-guided NPs) and controls (Table 4). The cognate CTLs are important for toxicity reduction because they are needed to "pull" guided NPs away from those PD-1-positive cells that accelerate the EAE. This study design is based on published EAE studies (errin P J, et al. CTLA-4 blockade enhances clinical disease and cytokine production during experimental allergic encephalomyelitis. Journal of immunology. 1996; 157(4):1333-6; Kuhns M S, et al. Cytotoxic T lymphocyte antigen-4 (CTLA-4) regulates the size, reactivity, and function of a primed pool of CD4+ T cells. Proceedings of the National Academy of Sciences of the United States of America. 2000; 97(23):12711-6; Miller S D, et al J. Experimental autoimmune encephalomyelitis in the mouse. Curr Protoc Immunol. 2007; Chapter 15: Unit 15 1; Yang K, et al. Deficiency of thrombospondin-1 reduces Th17 differentiation and attenuates experimental autoimmune encephalomyelitis. Journal of Autoimmunity. 2009; 32(2):94-103; Libbey J E, et al S. The effects of diet on the severity of central nervous system disease: One part of lab-to-lab variability. Nutrition. 2016; 32(7-8):877-83; and Tsunoda I, et al. Contrasting roles for axonal degeneration in an autoimmune versus viral model of multiple sclerosis: When can axonal injury be beneficial? Am J Pathol. 2007; 170(1):214-26). FIG. 10 shows a schedule of all experimental procedures.

TABLE 5

The treatments and their expected EAE scores (Yang K, et al. Deficiency of thrombospondin-1 reduces Th17 differentiation and attenuates experimental autoimmune encephalomyelitis. Journal of Autoimmunity. 2009; 32(2): 94-103).

| Treatment | Mean Max clinical Score |
| --- | --- |
| Guided αPD-1 NPs | 1.0~1.5 |
| Free αPD-1 | 3.0 |
| Unguided αPD-1 NPs | 3.0 |
| Guided, empty NPs | 1.0 |
| PBS | 1.0 |

The mice will be monitored and assigned EAE clinical scores according to a well-accepted scoring system for up to 40 days after the EAE induction (Miller S D, et al J. Experimental autoimmune encephalomyelitis in the mouse. Curr Protoc Immunol. 2007; Chapter 15: Unit 15 1; and Libbey J E, et al S. The effects of diet on the severity of central nervous system disease: One part of lab-to-lab variability. Nutrition. 2016; 32(7-8):877-83). Then, mean maximal clinical scores will be compared between the guided αPD-1 NP treatment and each of the four control treatments. The expected results are listed in Table 5. Pathology analysis will also be carried out on the central nervous system of these mice (Libbey J E, et al S. The effects of diet on the severity of central nervous system disease: One part of lab-to-lab variability. Nutrition. 2016; 32(7-8):877-83). The pathology results serve as an independent confirmation to the clinical score results.

Determine whether guided αPD-1 improves efficacy over free αPD-1. For this comparison, the mouse B16 melanoma model will be used and a dosing schedule previously described (Curran M A, et al. PD-1 and CTLA-4 combination blockade expands infiltrating T cells and reduces regulatory T and myeloid cells within B16 melanoma tumors. Proceedings of the National Academy of Sciences of the United States of America. 2010; 107(9):4275-80; and Holmgaard R B, et al. Indoleamine 2,3-dioxygenase is a critical resistance mechanism in antitumor T cell immunotherapy targeting CTLA-4. The Journal of experimental medicine. 2013; 210(7):1389-402). Table 6 lists all the treatment groups and expected results. The comparison will be carried out at a dosing level of 200 µg/mouse of guided αPD-1 or free αPD-1[45]. Tumor size and mouse survival will be used as two measures of the efficacy of the treatments. The guided αPD-1 mixture is the same as described above.

TABLE 6

The treatment design and expected efficacy.

| Group | Treatment | Expected efficacy |
| --- | --- | --- |
| 1 | Mixture of 3 guided αPD-1 NP | +++++ |
| 2 | gp100 tetramer-guided αPD-1 NP | ++ |
| 3 | Trp-1 tetramer guided αPD-1 NP | ++ |
| 4 | Trp-2 tetramer guided αPD-1 NP | ++ |
| 5 | PBS | − |
| 6 | Mixture of 3 guided NPs/No mAb | − |
| 7 | Free αPD-1 | ++ |

Determine the enhancement effect of guided αPD-1 to systematic and intra-melanoma CTL immunity. According to preclinical studies, αPD-1 cures melanoma or inhibits melanoma growth by increasing the number of active CTLs in the tumor and spleen (systematic)[35, 46]. Thus, experiments will investigate whether the expected improvement of the efficacy by guided αPD-1 (is accompanied with increases of targeted, melanoma-reactive CTLs in the tumor and spleen. Mice will treated as described above and in Table 6 except that intra-melanoma and splenic CD8 cells will be collected at 10 days after the last treatment. The CTLs will be quantified using ELISPOT or tetramer staining (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78; and Atanackovic D, et al. Vaccine-Induced CD4+ T Cell Responses to MAGE-3 Protein in Lung Cancer Patients. The Journal of Immunology. 2004; 172(5):3289-96). The activity of the CTLs collected from the tumor and spleen will be analyzed. A LDH-based CTL assay and intracellular cytokine staining (TNF-α, IFN-α) will be used to measure the activity (Li B, et al. Anti-programmed death-1 synergizes with granulocyte macrophage colony-stimulating factor—secreting tumor cell immunotherapy providing therapeutic benefit to mice with established tumors. Clinical cancer research: an official journal of the American Association for Cancer Research. 2009; 15(5):1623-34; Atanackovic D, et al. Vaccine-Induced CD4+ T Cell Responses to MAGE-3 Protein in Lung Cancer Patients. The Journal of Immunology. 2004; 172(5):3289-96; Yousef S, et al. Cancer-testis antigen SLLP1 represents a promising target for the immunotherapy of multiple myeloma. Journal of translational medicine. 2015; 13(1):

197; and Stubig T, et al. 5-Azacytidine Promotes an Inhibitory T-Cell Phenotype and Impairs Immune Mediated Antileukemic Activity. Mediators of Inflammation. 2014; 2014: 12). It is expected that guided αPD-1 will be more effective in amplifying active, melanoma-reactive CTLs in both the spleens and the melanoma than free αPD-1.

It is expected that the generated tetramer-guided αPD-1 NPs will preferentially bind melanoma-reactive CTLs and that the NPs will have improved efficacy and reduced autoimmune toxicity over free αPD-1.

Example 5: Develop Multifunctional Vaccine NPs to Amplify Melanoma-Reactive CTLs Multifunctional vaccine NPs to amplify melanoma-reactive CTLs was developed. To this end, the NPs were assembled from iTEP-fusion polypeptides. The NPs have multiple functional elements to overcome barriers of CTL vaccination: dendritic cell (DC) targeting, phagolysosomal escape, vaccine release, DC activation, and Th activation. How effectively the NPs amplify the CTLs will be evaluated.

The multifunctional vaccine NP that was assembled validated two functions of the NP. The CTL vaccine NP described herein is expected to address barriers of the vaccines. It is different in that a NP carrier can assume so many functionalities yet is simply assembled from one polypeptide.

Melanoma CTL epitope vaccines will be used to augment melanoma-reactive CTLs because these vaccines have unparalleled specificity and are suitable to amplify defined clones of CTLs (Purcell A W, et al. More than one reason to rethink the use of peptides in vaccine design. Nat Rev Drug Discov. 2007; 6(5):404-14). CTL vaccine NPs will be developed as a vaccine carrier since vaccine carriers have been proven to enhance CTL peptide vaccines (Bachmann M F, et al. Vaccine delivery: a matter of size, geometry, kinetics and molecular patterns. Nature reviews Immunology. 2010; 10(11):787-96; and Li W A, et al. Materials based tumor immunotherapy vaccines. Curr Opin Immunol. 2013; 25(2): 238-45. The vaccine NPs described herein are different and powerful since they will have the multi-functionalities to overcome the barriers between the administration of CTL vaccines to the onset of CTL immune responses (activation of CD8 T cells) as illustrated in FIG. 11: (1) the targeting of the vaccines to DCs, (2) the translocation of the vaccines from phagolysosome to cytosol, (3) the release of the epitope vaccines from their carriers, (4) the need of concurrent DC activation while inducing CTL responses, (5) the need for concurrent Th activation while inducing CTL responses[72, 75-77]. The NPs are also different because they can be assembled from a single fusion polypeptide as illustrated in FIG. 12. The fusion sequence is: NH2-Lamα5 (AQARSAASKVKVSMKF)-Pol(AVGAGATAEE)-iTEP-B70-iTEPA56-CysTag-PADRE(AKFVAAWTLKAAA)-CTL Vaccine—COOH. The design of the multifunctional vaccine NPs is based on the RED NP to address Barriers 1 and 3 (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78). A Pol peptide, AVGAGATAEE (SEQ ID NO: 19), that is derived from a DNA polymerase of HSV-1 was reported to promote the translocation of its fusion from the phagolysosome into cytosol (Barrier 2) (De Haan L, et al. Enhanced delivery of exogenous peptides into the class I antigen processing and presentation pathway. Infection and immunity. 2002; 70(6): 3249-58; and Loregian A, et al. Intranuclear delivery of an antiviral peptide mediated by the B subunit of *Escherichia coli* heat-labile enterotoxin. Proceedings of the National Academy of Sciences of the United States of America. 1999; 96(9):5221-6). Pol has double protonable glutamate residues to penetrate the vesicular membrane (De Haan L, et al. Enhanced delivery of exogenous peptides into the class I antigen processing and presentation pathway. Infection and immunity. 2002; 70(6):3249-58). A Lamα5 peptide, AQARSAASKVKVSMKF (SEQ ID NO: 16), that is derived from the αchain of laminin-10, a basement membrane protein, was previously reported to activate macrophages (Adair-Kirk T L, et al. A site on laminin alpha 5, AQARSAASKVKVSMKF, induces inflammatory cell production of matrix metalloproteinase-9 and chemotaxis. Journal of immunology. 2003; 171(1):398-406; and Adair-Kirk T L, et al. A chemotactic peptide from laminin alpha 5 functions as a regulator of inflammatory immune responses via TNF alpha-mediated signaling. Journal of immunology. 2005; 174(3):1621-9). FIG. 13 shows that Lamα5 potently activated DCs. Thus, Lamα5 might be a useful element to overcome Barrier 4. A commonly used Th vaccine, pan DR epitope (PADRE: AKFVAAWTLKAAA (SEQ ID NO: 17), is included in the multifunctional NPs so that the NPs are able to activate Th responses (Barrier 5)[82]. FIG. 14 shows that (1) an NP was generated as described in FIG. 12 (and described above) with a hydrodynamic diameter of 67.0±9.8 nm; (2) Pol on the NP enhanced the cytosolic accumulation of the NP; and (3) Lamα5 on the NP activated and matured DCs. Thus, w a multifunctional vaccine NP with two confirmed functionalities to overcome Barriers 2 and 4 was attained. Further, this NP likely overcomes Barriers 1 and 3 because it is based on the RED-NP (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78).

Since the proposed multifunctional vaccine NPs are expected to overcome the barriers of CTL vaccines, the NPs may likely outperform those CTL vaccine formulations used in clinical trials, such as Montanide ISA-51 (Pol J, et al. Trial Watch: Peptide-based anticancer vaccines. Oncoimmunology. 2015; 4(4):e974411). Thus, Montanide ISA-51 can be used as a benchmark to measure the effectiveness of the proposed vaccines. Montanide ISA-51 has been proven appropriate for mouse studies (Arevalo-Herrera M, et al. Preclinical vaccine study of *Plasmodium vivax* circumsporozoite protein derived-synthetic polypeptides formulated in montanide ISA 720 and montanide ISA 51 adjuvants. The American journal of tropical medicine and hygiene. 2011; 84(2 Suppl):21-7).

The experiments are grouped into two phases. In Phase One, a vaccine NP that has functionalities to overcome the barriers will be engineered using a model CTL vaccine, SIINFEKL (SEQ ID NO: 41) (pOVA), to test the NP. In Phase Two, the NP will be loaded with melanoma CTL vaccines, gp100, Trp-1, and Trp 2, and CTL responses induced by new NPs will be evaluated.

Generate a model, multifunctional, vaccine NP with the pOVA vaccine. WA multifunctional NP consisting of all elements and pOVA (SIINFEKL; SEQ ID NO: 41) was generated as model CTL vaccines. The NP was assembled from a single iTEP fusion and stabilized through disulfide bonds inside the NP as previously reported (Dong S, et al. A Comparison Study of iTEP Nanoparticle-Based CTL Vaccine Carriers Revealed a Surprise Relationship between the Stability and Efficiency of the Carriers. Theranostics.

2016; 6(5):666-78). Lamα5 should be displayed on the surface of the NP. The fusion was produced as a recombinant protein from E. coli.

Examine whether the multifunctional vaccine NP resolves barriers of CTL peptide vaccines. First, experiments will be performed to check whether the vaccine NP has a passive DC targeting function due to its particle structure. DC uptake of the vaccine NP and a soluble polypeptide control will be compared. This polypeptide has all other elements but the amphiphilic iTEP, $iTEP_{B70}$-$iTEP_{A56}$. Instead, it has hydrophilic $iTEP_{B70}$ as its backbone. A previously established protocol will be used for this characterization (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78).

Second, experiments will be performed to check whether Pol on the NP promotes translocation of the NP from the phagolysosome to cytosol. Fluorescein-labelled NPs will be used to examine the distribution of the NP in cytosol and vesicle compartments using a cell fraction method that was used to generate data in FIG. 14B (Baghirova S, et al. Sequential fractionation and isolation of subcellular proteins from tissue or cultured cells. MethodsX. 2015; 2:440-5; and Holden P, et al. Crude subcellular fractionation of cultured mammalian cell lines. BMC Res Notes. 2009; 2:243. The fluorescent intensity ratios between cytosol fraction to vesicle fraction of the DCs are shown. The data demonstrate the function of Pol in the NPs. The control of the study will be with the same NP without Pol.

Third, experiments will be performed to check whether the vaccine NP is able to promote epitope release. To answer this question, it will be examined whether the disulfide bonds in the NP can be reduced and whether the reduction promotes the dissociation of the NP. Then, experiments will be carried out to compare whether the NP results in a greater vaccine presentation than a stable NP with all functional elements except for the CysTag. A previously reported method will be used to complete the comparison (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78).

Fourth, it will be examined whether the NP has an ability to activate DCs by checking cytokine release (IL-6, TNF-α) and surface marker expression (CD40, CD80) from DC2.4 cells as described in FIGS. 14C and 14D. Mean fluorescence intensities (MFIs) were measured by flow cytometry (N=3). These data (FIGS. 14C & D) verify the function of Lamα5 on the NPs. The same NP without Lamα5 as a negative control and LPS as a positive control (Clawson C, et al. Delivery of a peptide via poly(d,l-lactic-co-glycolic) acid nanoparticles enhances its dendritic cell-stimulatory capacity. Nanomedicine: Nanotechnology, Biology and Medicine. 6(5):651-61) will be used. To substantiate the results, the DC activation capacity of the NP using primary DCs collected from B6 mice will be confirmed.

Fifth, it will be confirmed that the NP induces Th responses in vivo. Th responses will be evaluated using IFN-γ and IL-2-based ELISPOT (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78; Fujihashi K, et al. Cytokine-specific ELISPOT assay single cell analysis of IL-2, IL-4 and IL-6 producing cells. Journal of immunological methods. 1993; 160(2):181-9). Both cytokines are markers of the Th1 immunity polarization that favors a CTL response and tumor elimination (Murphy K. Dynamics of Adaptive Immunity. Janway's Immunobiology. 8 ed. New York, USA: Garland Science; 2012. p. 429-64). The control sample for the study will be the same NP without PADRE.

Sixth, CTL responses (CTL amplification) induced by the multifunctional NP will be evaluated. The vaccines used in this study and their expected responses are listed in Table 7. The characterization of CTL responses will be the same as described in Example 3 except splenic CD8 cells will be used.

TABLE 7

The compared vaccines and their expected CTL responses.

| Vaccines | Functionality | Expected response |
|---|---|---|
| Multifunctional NP | DC-targeting, translocation, epitope release, DC activation, Th activation | +++++ |
| Control NP 1 | Lack "translocation" | +++ |
| Control NP 2 | Lack "epitope release" | +++ |
| Control NP 3 | Lack "DC activation" | +++ |
| Control NP 4 | Lack "Th activation" | ++++ |
| SIINFEKL (SEQ ID NO: 41) | Lack all functionality | + |
| SIINFEL + Montanide ISA-51 | N/A | +++ |

Prepare melanoma vaccine NPs. gp100, Trp-1, and Trp-2 melanoma CTL peptide vaccines, respectively, will be loaded (as described in Example 3) into the multifunctional vaccine NP. This loading can be achieved by inserting the vaccines in the fusion illustrated in FIG. 12. All the vaccines are hydrophobic, so they will be located in the hydrophobic core of the NPs. Each of the three NPs generated will carry one melanoma vaccine.

Evaluate CTL responses elicited by melanoma vaccine NPs using healthy B6 mice, B6 mice with B16 melanoma, and B6 mice with EAE. Systemic and intratumoral (when applicable) CTL responses toward the NPs will be examined. W A mixture of three vaccine NPs will be co-administered to one single mouse in order to expand the three clones of CTLs concomitantly. The test mice will include healthy B6 mice, B6 mice with melanoma, and B6 mice with EAE. The CTL responses may be different among these three types of mice since these mice offer different immune milieu. The CTL responses will be characterized as described in Example 3. It is expected that these NPs will induce stronger CTL responses when compared to free vaccines, or the vaccines with Montanide ISA-51.

Vaccine NPs having multiple functionalities will be produced which are more potent than Montanide ISA-51 at inducing CTL responses. This outcome will help to amplify melanoma-reactive CTLs and enhance the αPD-1 therapy.

Adding to the NPs one or more additional elements to actively target the NPs to DCs is contemplated. One example of such elements is an antibody that recognizes a DC surface molecule, e.g., DEC-205. Anti-DEC-205 successfully enhanced the potency of vaccine carriers (Kreutz M, et al. Targeting dendritic cells—why bother? Blood. 2013; 121(15):2836-44; and van Broekhoven C L, et al. Targeting Dendritic Cells with Antigen-Containing Liposomes: A Highly Effective Procedure for Induction of Antitumor Immunity and for Tumor Immunotherapy. Cancer Research. 2004; 64(12):4357-65) and is likely to boost the potency of the vaccine NPs disclosed herein.

Example 6: Development of a Dual NP-Based Combinational Therapy that is Superior to αPD-1 Monotherapies A dual NP-based combinational therapy will be developed. The combination therapy may be superior to αPD-1 therapies. The kinetics of the vaccine NP-induced CTL responses and the pharmacokinetics (PK) of guided αPD-1 NPs will be profiled. Based on the kinetics and the PK, dual-NP based combinational therapies will be designed and various treatment regimes will be examined. Finally, the combinational therapy with a selected regimen outperforms αPD-1 monotherapies in terms of increasing efficacy and reducing toxicity will be examined.

The PK of the guided αPD-1 NP, which was prepared to synchronize CTL responses and dosing of the guided NP, was characterized.

Melanoma vaccine NP-induced CTL responses will be synchronized with the effects of guided αPD-1 NPs. A combinational therapy of CTL vaccine NPs and guided αPD-1 NPs will be developed. The regimen of this combinational therapy will be designed according to the kinetics of CTL responses and the PK of guided αPD-1 NPs. This rational synchronization of CTL responses and the effect of αPD-1 is distinct from previous combinational therapies of vaccines and αPD-1. In past therapies, it was impossible to orchestrate CTL responses and the effect of αPD-1 because it was not possible to define effector cells in those therapies (Curran M A, et al. PD-1 and CTLA-4 combination blockade expands infiltrating T cells and reduces regulatory T and myeloid cells within B16 melanoma tumors. Proceedings of the National Academy of Sciences of the United States of America. 2010; 107(9):4275-80; and Fu J, et al. Preclinical Evidence That PD1 Blockade Cooperates with Cancer Vaccine TEGVAX to Elicit Regression of Established Tumors. Cancer Research. 2014; 74(15):4042-52).

The toxicity of αPD-1 will be addressed by resolving the reason for the toxicity, which is distinct from current toxicity management methods. The methods disclosed herein may change the management of αPD-1 toxicity; the management will no longer be associated with non-specific immune suppression.

Research Design. With tools (NPs) to deliver αPD-1 to melanoma-reactive CTLs and to amplify the CTLs, experiments will be performed to test whether the targeted αPD-1 therapy has improved efficacy and reduced toxicity as compared to the current αPD-1 therapy. Further, since both CTL responses (the numbers of amplified CTLs by vaccine NPs) (FIG. 15) (Kaech S M, et al. Effector and memory T-cell differentiation: implications for vaccine development. Nature reviews Immunology. 2002; 2(4):251-62) and plasma concentration of guided αPD-1 NPs (FIG. 16) are dynamic, it will be tested whether the combination of the two NPs is most effective if the peak concentrations of guided αPD-1 NPs overlap with the peak numbers of melanoma-reactive CTLs, the peak-overlapping regimen. Compared to the reported PD-1 therapies, it is possible to synchronize the peak concentrations and the peak numbers because epitope vaccines are used to induce clone-specific CTL responses. In contrast, the current αPD-1 monotherapy relies on tumor-induced CTL responses, and the reported combinational therapies used tumor cells as vaccines (Curran M A, et al. PD-1 and CTLA-4 combination blockade expands infiltrating T cells and reduces regulatory T and myeloid cells within B16 melanoma tumors. Proceedings of the National Academy of Sciences of the United States of America. 2010; 107(9):4275-80; and Fu J, et al. Preclinical Evidence That PD1 Blockade Cooperates with Cancer Vaccine TEGVAX to Elicit Regression of Established Tumors. Cancer Research. 2014; 74(15):4042-52. In these two cases, many CTL clones are involved and hence it is difficult to clearly delineate and pace CTL responses.

To carry out the experiments described above, the kinetics of vaccine-induced CTL responses and the PK of guided αPD-1 NPs will be defined; then efficacy and toxicity evaluations will be performed; and, lastly, correlations will be analyzed between the regimens of the combinational therapy, CTL responses, and the efficacy and toxicity results. The correlational study should reveal whether CTL responses are a mechanistic link between the efficacy and toxicity results and the regimens, which is important for further optimization of the combinational therapy.

Results. PK analysis results (Table 8) show that unguided αPD-1 NPs and free αPD-1 have similar Cmax, Tmax, and $T_{\alpha 1/2}$, but different $T_{\beta 1/2}$, and AUC. The AUC of the unguided NPs is about 3 times smaller than that of free αPD-1. The guided NPs show a similar kinetics trend as the unguided NPs. Additionally, data in FIG. 9 showed that αPD-1 enhanced melanoma-reactive CTL responses in B16 tumored mice, which supports the feasibility of the proposed combinational therapy.

TABLE 8

PK Parameters.

| Samples | Free αPD-1 | Unguided αPD-1 NP |
|---|---|---|
| Maximum plasma concentration ($C_{max}$, μM)) | 2.11 | 1.97 |
| Time to reach $C_{max}$ ($T_{max}$, h) | 1.61 | 1.43 |
| Distribution half-live ($T_{\alpha 1/2}$, h) | 2.79 | 2.36 |
| Elimination half-life ($T_{\beta 1/2}$, h) | 60.26 | 106.64 |
| Area under curve (AUC, μM * h) | 121.91 | 42.65 |

Characterize the kinetics of CTL responses induced by melanoma vaccine NPs. The kinetics of the CTL responses will be profiled by defining the peaks and boundaries of the expansion, contraction, and memory phases of the responses, similar to the typical CTL response kinetics illustrated in FIG. 15 (Hamilton S E, et al. Quantitation of CD8+ T cell expansion, memory, and protective immunity after immunization with peptide-coated dendritic cells. Journal of immunology. 2002; 169(9):4936-44). To induce the responses, the vaccine NPs will be used to vaccinate the mice twice with a 10-day interval. Circulating CD8 T cells will be collected from the vaccinated mice seven times from the date of the first immunization to the 28th day after the second immunization. CTL responses will be quantified using the frequencies of melanoma-reactive CTLs among the CD8 T cells. Two methods will be used, tetramer and intra-cellular IFN-γ staining, to obtain the frequency values (Hamilton S E, et al. Quantitation of CD8+ T cell expansion, memory, and protective immunity after immunization with peptide-coated dendritic cells. Journal of immunology. 2002; 169(9):4936-44; and Cho S, et al. Immune-tolerant elastin-like polypeptides (iTEPs) and their application as CTL vaccine carriers. Journal of Drug Targeting). If the number of circulating, melanoma-reactive CTLs is too small to detect, splenocyte samples will be used instead of circulating CD8 T cell samples for this study. The controls will be PBS and empty NPs (no vaccines).

Establish the PK of guided αPD-1 NPs. Either guided αPD-1 or free αPD-1 that are pre-labeled with rhodamine (5 nmol αPD-1 per mouse) will be administered. We will then monitor plasma αPD-1 levels at 10 different time points between 15 min to 96 hr after the administration, a design based on results (FIG. 16) described herein. Larger sample sizes at each time point will be used to get more robust data. According to the plasma αPD-1 data, several key PK parameters will be obtained including, Cmax, Tmax, $T_{\alpha1/2bsop}$, $T_{\beta1/2}$, and AUC by using PKSolver program (Zhang Y, et al. PKSolver: An add-in program for pharmacokinetic and pharmacodynamic data analysis in Microsoft Excel. Comput Methods Programs Biomed. 2010; 99(3): 306-14). The ELISA method will be used to independently confirm the serum αPD-1 levels (Gardiner D, et al. A randomized, double-blind, placebo-controlled assessment of BMS-936558, a fully human monoclonal antibody to programmed death-1 (PD-1), in patients with chronic hepatitis C virus infection. PloS one).

Examine whether the combinational therapy is more efficient in treating B16 melanoma than monotherapies. Table 9 shows the treatments and their expected results in this study. For combinational therapy, the melanoma vaccine NP mixture as described in Example 4 and the mixture of three guided αPD-1 NPs developed in Example 3 will be used; and the peak-overlapping regimen will also be used. The schedule of all major experimental procedures is shown in FIG. 17. The intervals between the administrations of vaccines and different αPD-1 formulations will be decided based on the peak of CTL responses and the PK of guided NPs (see above). Other schedules are designed as described in Example 3. If the peak period of CTL responses is longer than $T_{\beta1/2}$ of guided αPD-1 NPs, the dosing of the NPs will be repeated to maintain a high plasma concentration of αPD-1 when there are large numbers of melanoma-reactive CTLs in the body. The efficacy by tumor growth and mouse survival time will be assessed as the described in Example 3.

TABLE 9

The treatment design and expected therapeutic outcome.

| Group | Treatment | Expected efficacy |
|---|---|---|
| 1 | Mixture of 3 vaccines & mixture of 3 guided αPD-1 | +++++ |
| 2 | PBS | − |
| 3 | Free αPD-1 | + |
| 4 | Mixture of 3 guided αPD-1 | +++ |

Examine whether the combinational therapy is less toxic than monotherapy. The toxicity will be compared using the EAE model. The treatment design and schedule will be the same as described in Table 9 and FIG. 17 except that tumor inoculation will be replaced by EAE induction. The EAE induction procedures and its scoring method are described herein. It is expected that the combinational therapy (Treatment 1) will be less toxic (inducing a lower level of or no EAE) than those induced by either free αPD-1 or the guided αPD-1 NP monotherapy.

Examine whether the peak-overlapping regimen is superior to other regimens for the combinational therapy (efficacy evaluation). The peak-overlapping regimen will be compared with the combinational therapies using three non-overlapping regimens: when the guided αPD-1 NPs are administered (1) at the middle point of the CTL expansion phase, (2) at the middle point of the contraction phase, and (3) during the memory phase of the CTL responses (FIG. 15). The experimental procedures including tumor inoculation, vaccination, and αPD-1 administration will be identical to those described herein. Through the comparisons, conclusions can be made whether the peak-overlapping regimen best supports the tumor treatment effect of the combinational therapy. Additionally, CTL responses in each treated mouse using the method described in Example 4 will be assessed and a correlation analysis between the efficacy, CTL responses, and the regimens will be carried out.

Examine whether the peak-overlapping regimen is superior to other schedules for the combinational therapy (toxicity evaluation). We will compare the regimens described herein for their toxicity. Through the comparisons, conclusions can be made whether the peak-overlapping regimen most effectively reduces the toxicity of αPD-1. CTL responses will be characterized and a correlation analysis between the toxicity, CTL responses, and the regimens will be carried out.

The combinational therapy will show a significant improvement of efficacy and safety over the monotherapies of αPD-1. A rationally designed combinational regimen (the peak-overlapping regimen) is the most effective one for the combinational therapy.

CTL clones that are restricted to epitopes of surviving, Wilms' tumor 1, and NY-ESO-1 (Pol J, et al. Trial Watch: Peptide-based anticancer vaccines. Oncoimmunology. 2015; 4(4):e974411; Lens M. The role of vaccine therapy in the treatment of melanoma. Expert opinion on biological therapy. 2008; 8(3):315-23; Lladser A, et al. Intradermal DNA electroporation induces survivin-specific CTLs, suppresses angiogenesis and confers protection against mouse melanoma. Cancer Immunol Immunother. 2010; 59(1):81-92; Zamora-Avila D E, et al. WT1 gene silencing by aerosol delivery of PEI-RNAi complexes inhibits B16-F10 lung metastases growth. Cancer Gene Ther. 2009; 16(12):892-9; and Zarour H M, et al. NY-ESO-1 119-143 Is a Promiscuous Major Histocompatibility Complex Class II T-Helper Epitope Recognized by Th1- and Th2-Type Tumor-reactive CD4+ T Cells. Cancer Research. 2002; 62(1):213-8) are contemplated. Targeting αPD-1 to CD137-positive T cells to broaden anti-melanoma immune responses is also within the scope of the invention. CD137 has been reported as a biomarker identifying tumor-reactive T cells in melanoma; thus targeting this population of T cells may improve both the efficacy and the safety of αPD-1 (Ye Q, et al. CD137 accurately identifies and enriches for naturally occurring tumor-*reactive T cells in tumor. Clinical cancer research: an official journal of the American Association for Cancer Research.* 2014; 20(1):44-55). Even if the targeted αPD-1 therapy does not improve the efficacy of αPD-1, the reduction of its toxicity still carries multiple benefits: broadening patient populations, improving quality of life for treatment patients, and increasing response rates of treated patients because patients can take higher doses of targeted αPD-1 for a longer time.

Statistical plan and power analysis. Paired comparisons will be conducted in this study. For paired comparisons in Examples 3 and 5 an equivalence, two one-sided test (TOST) with a significance level of 0.05(101) will be used; it is expected that outcomes between the two groups will not be statistically different. In Example 5, particularly, the theory that the AUC of guided αPD-1 NPs is within a two-fold difference to the AUC of free αPD-1. In contrast, a non-equivalence, t-test (or its non-parametric alternative) with a significance level of 0.05 in other comparisons of this study will be used except for survival data. In non-equivalence tests, it is expected that the outcomes between the two groups are statistically different. For survival data (Examples 3 and 5), a Log Rank test will be used. Power analysis was conducted based on the statistical tests used, previous published data, data described herein, and expected results. If results of a task are not normally distributed, a nonparametric test will be performed and 15% more mice will be used in that task to meet the group size requirement of nonparametric tests.

Rigorous Experiment Design. Regarding biological variables, an equal number of male and female mice in each group will be included; age affects CTL immunity (Makinodan T, et al M. Age influence on the immune system. Adv Immunol. 1980; 29(287):287); thus, 6-10 week old mice will be used; all mice will be randomized before the start of experiments while keeping the male-to-female ratio; weight and health condition will not affect conclusions due to the randomization.

Example 7: Engineer and Characterize Tetramer-Guided αCTLA-4 NPs

For antibodies like αCTLA-4 that bind cell surface antigens, it is intrinsically challenging to target them to a fraction of antigen-positive cells since the antibodies naturally interact with antigen-positive cells. To this end, a MHC class I tetramer-guided NP that is able to target these antibodies to a subpopulation of antigen-positive cells was developed (FIG. 7B). This NP has a high molar ratio between its targeting moiety, the tetramer, and its antibody payloads. Additionally, it was confirmed that the antibody on this NP (anti-programmed death-1 antibody (αPD-1); see above) was fully functional (FIG. 7C). Because of these results, it is thought that the tetramer-guided NP is able to target αCTLA-4 to melanoma-reactive CTLs and reduce the toxicity of αCTLA-4.

The design of tetramer-guided αCTLA-4 NPs. The NPs will be assembled from two fusions, immune-tolerant elastin-like polypeptide (iTEP)-tetramers and iTEP-αCTLA-4 as illustrated in FIG. 19. Disulfide bonds (green network inside the NP) stabilize the NP. The amphiphilic iTEP in these two fusions will drive the assembly of the NPs. After the NPs form, they will be stabilized through inter-polypeptide disulfide bonds resulting from oxidization. The aim is to produce a 10-to-1 ratio between tetramers and αCTLA-4 on the assembled NPs because a tetramer-to-antibody ratio of 10-to-1 on the tetramer-guided αPD-1 NP successfully permitted the NP to target αPD-1 to its cognate CTLs (FIG. 7B).

Three tetramer-guided NPs will be generated that target three independent clones of melanoma-reactive CTLs. These CTLs are responsible to eliminate melanoma cells expressing melanoma antigens, glycoprotein 100 (gp100), tyrosinase-related protein-1 (TRP-1), and tyrosinase-related protein-2 (TRP-2) (Overwijk W W, et al. gp100/pmel 17 is a murine tumor rejection antigen: induction of "self"-reactive, tumoricidal T cells using high-affinity, altered peptide ligand. J Exp Med. 1998; 188(2):277-86; Dyall R, et al. Heteroclitic immunization induces tumor immunity. J Exp Med. 1998; 188(9):1553-61; and Bloom M B, P et al. Identification of tyrosinase-related protein 2 as a tumor rejection antigen for the B16 melanoma. J Exp Med. 1997; 185(3):453-9). The three clones of the CTLs are important to melanoma immunotherapy in both mice and humans (Mansour M, et al. Therapy of established B16-F10 melanoma tumors by a single vaccination of CTL/T helper peptides in VacciMax. Journal of translational medicine. 2007; 5:20; and Phan G Q, et al. Immunization of patients with metastatic melanoma using both class I- and class II-restricted peptides from melanoma-associated antigens. J Immunother. 2003; 26(4):349-56).

Study Design. Produce tetramer-guided NPs that will preferentially bind with melanoma-reactive CTLs over other CTLA-4-positive cells. Tests will be carried out to confirm the specificity of the tetramer-guided NPS using four controls, if not otherwise specified: (1) free αCTLA-4, (2) unguided αCTLA-4 NPs (no tetramers on the NPs), (3) tetramer-guided, empty NPs (no αCTLA-4 on the NPs), and (4) PBS.

Generate the iTEP-αCTLA-4 and the iTEP-tetramer. The design of iTEP-αCTLA-4 was described in Table 11. The HisTag facilitates the purification of the fusion, and the CysTag is useful to form inter-fusion disulfide bonds. This fusion polypeptide will be encoded by a single gene and generated in E. coli. The gene of the αCTLA-4 single chain variable domain fragment (scFv) will be cloned from the UC10-4F10 hybridoma through the GeneScript antibody service (Peggs K S, et al. Blockade of CTLA-4 on both effector and regulatory T cell compartments contributes to the antitumor activity of anti-CTLA-4 antibodies. J Exp Med. 2009; 206(8):1717-25; Davila E, et al E. Generation of antitumor immunity by cytotoxic T lymphocyte epitope peptide vaccination, CpG-oligodeoxynucleotide adjuvant, and CTLA-4 blockade. Cancer Res. 2003; 63(12):3281-8; Perrin P J, et al. CTLA-4 blockade enhances clinical disease and cytokine production during experimental allergic encephalomyelitis. J Immunol. 1996; 157(4):1333-6). The iTEP-tetramer will be generated via two steps: first, an iTEP-streptavidin fusion described in Table 11 will be generated as a recombinant polypeptide (Schultz J, et al. A Tetravalent Single-chain Antibody-Streptavidin Fusion Protein for Pretargeted Lymphoma Therapy. Cancer Research. 2000; 60(23):6663-9; second, the biotinylated MHC class I monomers (H2-Db/gp100 epitope, H2-Kb/TRP-1 epitope, and H2-Kb/TRP-2 epitope) will be mixed with the iTEP-streptavidin fusion to assemble three types of iTEP-tetramer fusions. These fusions will be generated using the protocol that was used to generate the αPD-1 NP (FIG. 6).

TABLE 11

The sequence design of two fusions.

The iTEP-αCTLA4: $NH_2$-HisTag[$H_6$]-Linker[(GGGSG)]-αCTLA-4 (scFv)-iTEP$_{B70}$[(GAGVPG)$_{70}$]-iTEP$_{A56}$[(GVLPGVG)$_{56}$]-CysTag [(GC)$_4$]-COOH
The iTEP-streptavidin: $NH_2$-HisTag-Linker-Streptavidin-iTEP$_{B70}$-iTEP$_{A56}$-CysTag-COOH Form and characterize tetramer guided αCTLA-4 NPs. After mixing the iTEP-tetramer and the iTEP-αCTLA-4 at a 10-to-1 ratio, the size of the mixed fusions will be analyzed by dynamic light scattering (DLS) to confirm that these fusions form NPs (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78). After the confirmation, the disulfide bonds between fusions will be oxidized to stabilize the NPs as previously conducted (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78). Control NPs will be prepared and characterized in the same way.

Confirm the function (e.g., binding) of αCTLA-4 on tetramer-guided αCTLA-4 NPs using a competitive binding assay. Alexa488-labeled αCTLA-4 (intact antibody) will be used to compete with the NPs for binding to Tregs (CTLA-4-positive cells) (Peggs K S, et al. Blockade of CTLA-4 on both effector and regulatory T cell compartments contributes to the antitumor activity of anti-CTLA-4 antibodies. J Exp Med. 2009; 206(8):1717-25). The results are expected to be similar to those in FIGS. 7B and 7C.

Examine the preferential binding of tetramer guided αCTLA-4 NPs to their cognate CTLs. Alexa488-labeled, tetramer-guided αCTLA-4 NPs will be incubated with a cell mixture of cognate CTLs and non-cognate Tregs (1:1 ratio). The fractions of Alexa488-stained CTLs and Alexa488-stained Tregs after incubation will be quantified by flow cytometry. The Targeting Efficiency as defined herein will be calculated for the guided αCTLA-4 NPs and their control. It is expected that the targeting efficiency of the NPs will be significantly greater than that of the controls, indicating that the tetramer-guided NPs are able to target αCTLA-4 to cells with TCRs cognate to the tetramers.

Example 8: Engineer and Characterize Tetramer-Guided αCTLA-4 NPs

Experiments will be carried out to test whether tetramer-guided αCTLA-4 NPs do not aggravate EAE as much as free αCTLA-4. An EAE model will be used to evaluate the toxicity because this model is sensitive to the toxicity of αCTLA-4 (Perrin P J, et al. CTLA-4 blockade enhances clinical disease and cytokine production during experimental allergic encephalomyelitis. J Immunol. 1996; 157(4):1333-6; and Kuhns M S, et al P. Cytotoxic T lymphocyte antigen-4 (CTLA-4) regulates the size, reactivity, and function of a primed pool of CD4+ T cells. Proc Natl Acad Sci USA. 2000; 97(23):12711-6).

Study design. In general, EAE will be induced concurrently with the amplification of the CTLs cognate to the tetramer-guided NPs in C57BL/6 mice. Then, these mice will be treated with tetramer-guided αCTLA-4 NPs and controls. The cognate CTLs are important for toxicity reduction because they are needed to "pull" tetramer-guided αCTLA-4 NPs away from those CTLA-4-positive cells that accelerate the EAE amid the higher avidity between the CTLs and the NPs. The study was designed according to published EAE studies (Perrin P J, et al. CTLA-4 blockade enhances clinical disease and cytokine production during experimental allergic encephalomyelitis. J Immunol. 1996; 157(4):1333-6; Kuhns M S, et al P. Cytotoxic T lymphocyte antigen-4 (CTLA-4) regulates the size, reactivity, and function of a primed pool of CD4+ T cells. Proc Natl Acad Sci USA. 2000; 97(23):12711-6; Miller S D, et al J. Experimental autoimmune encephalomyelitis in the mouse. Curr Protoc Immunol. 2007; Chapter 15: Unit 15 1; and Yang K, et al. Deficiency of thrombospondin-1 reduces Th17 differentiation and attenuates experimental autoimmune encephalomyelitis. Journal of Autoimmunity. 2009; 32(2):94-103. FIG. 10 shows a schedule of all experimental procedures.

The cognate CTLs will be amplified by vaccination with a mixture of the aforementioned epitopes: gp100, TRP-1, and TRP-2. Previously proven vaccine carriers will be used to enhance the vaccination instead of using common adjuvants (Dong S, et al. A Comparison Study of iTEP Nanoparticle-Based CTL Vaccine Carriers Revealed a Surprise Relationship between the Stability and Efficiency of the Carriers. Theranostics. 2016; 6(5):666-78) because those adjuvants may interfere with systematic immunity and hence alter the EAE induction while the previously proven vaccine carriers are immune tolerated and proven to enhance CTL vaccines (Cho S, et al. Immune-tolerant elastin-like polypeptides (iTEPs) and their application as CTL vaccine carriers. J Drug Target. 2016; 24(4):328-39).

EAE will be induced in the above mice by the injection a myelin oligodendrocyte glycoprotein (MOG)-derived peptide (MOG$_{35-55}$: MEVGWYRSPFSRVVHLYRNGK; SEQ ID NO: 18) per mouse together with pertussis toxin (Tompkins S M, et al. De novo central nervous system processing of myelin antigen is required for the initiation of experimental autoimmune encephalomyelitis. J Immunol. 2002; 168(8):4173-83).

The above mice will be randomly assigned to 5 groups. Each group will receive one of the five treatments listed in Table 12. The dosing will be repeated five times at 100 μg αCTLA-4 equivalent per mouse with two-day intervals based on previous αCTLA-4 preclinical studies (Peggs K S, et al. Blockade of CTLA-4 on both effector and regulatory T cell compartments contributes to the antitumor activity of anti-CTLA-4 antibodies. J Exp Med. 2009; 206(8):1717-25; Davila E, et al E. Generation of antitumor immunity by cytotoxic T lymphocyte epitope peptide vaccination, CpG-oligodeoxynucleotide adjuvant, and CTLA-4 blockade. Cancer Res. 2003; 63(12):3281-8; van Elsas A, et al. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. 1999; 190(3):355-66; and Quezada S A, et al. CTLA4 blockade and GM-CSF combination immunotherapy alters the intratumor balance of effector and regulatory T cells. J Clin Invest. 2006; 116(7):1935-45. Both the guided αCTLA-4 NP sample and the guided, empty NP sample will contain three types of NPs that correspond to gp100, TRP-1, and TRP-2 antigens respectively. The three NPs will be mixed at a 1:1:1 ratio.

TABLE 12

The treatments and their expected results.

| Treatment | Mean Max clinical Score |
|---|---|
| Guided αCTLA-4 NPs | 1.0~1.5 |
| Free αCTLA-4 | 3.0 |
| Unguided αCTLA-4 NPs | 3.0 |
| Guided, empty NPs | 1.0 |
| PBS | 1.0 |

The mice will be monitored and assigned EAE clinical scores according to a well-accepted scoring system for up to 40 days after EAE induction (Libbey J E, et al. The effects of diet on the severity of central nervous system disease: One part of lab-to-lab variability. Nutrition. 2016; 32(7-8):877-83; and Miller S D, et al J. Experimental autoimmune encephalomyelitis in the mouse. Curr Protoc Immunol. 2007; Chapter 15: Unit 15 1). Then, mean maximal clinical scores will be compared between the tetramer-guided αCTLA-4 NP treatment and each of the four control treatments. Pathology analysis will be performed on the central nervous system of these mice using a known protocol (Libbey J E, et al. The effects of diet on the severity of central nervous system disease: One part of lab-to-lab variability. Nutrition. 2016; 32(7-8):877-83). The pathology results will serve as an independent confirmation to the clinical score results.

Tetramer-guided αCTLA-4 NPs will be examined to confirm whether they have improved efficacy as compared to free αCTLA-4. Combination therapies consisting of the NPs and CTL vaccines will be examined to confirm whether the combination therapy is superior to the NP monotherapy with regard to efficacy and toxicity.

What is claimed is:

1. A nanoparticle comprising:
   a) one or more immune-tolerant elastin-like polypeptide (iTEP)-tetramers, wherein the one or more iTEP-tetramers comprise in amino terminal-to-carboxy terminal order (i) four MHC class I monomers, wherein the MHC class I monomers are H2-D$^b$/gp100 epitope, H2-K$^b$/TRP-1 epitope, H2-K$^b$/TRP-2 epitope, or MHC class I tumor-associated epitopes, (ii) a first iTEP sequence, wherein the first iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21), (iii) a second iTEP sequence, wherein the second iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21), and (iv) a cysteine containing tag; and
   b) one or more iTEP-fusion molecules, wherein the one or more iTEP-fusion molecules comprise (i) a HisTag; (ii) a linker; (iii) therapeutic agent, wherein the therapeutic agent is a single chain variable fragment of an anti- αCTLA-4 antibody or anti-αPD-1 antibody; (iv) a first iTEP sequence, wherein the first iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21); (v) a second iTEP sequence, wherein the second iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21), and (vi) a cysteine containing tag.

2. The nanoparticle of claim 1, wherein the first and second iTEP sequences in
   a) are different.

3. The nanoparticle of claim 1, wherein the cysteine containing tag comprises a tetracysteine motif.

4. The nanoparticle of claim 3, wherein the tetracysteine motif is Gly-Cys-Gly-Cys-Gly-Cys-Gly-Cys (SEQ ID NO: 22).

5. The nanoparticle of claim 1, wherein the cysteine containing tags of the one or more iTEP-tetramers and the cysteine tags of the one or more iTEP-fusion molecules are crosslinked by forming one or more disulfide bonds.

6. The nanoparticle of claim 1, wherein the first and second iTEP sequences in
   b) are different.

7. The nanoparticle of claim 1, wherein the ratio of iTEP-tetramers to iTEP-fusion polypeptides is 10:1.

8. The nanoparticle of claim 1, wherein the linker of the one or more iTEP-fusion polypeptides is GGGSG (SEQ ID NO: 33).

9. A pharmaceutical composition comprising the nanoparticle of claim 1 and a pharmaceutically acceptable carrier.

10. The pharmaceutical composition of claim 9, wherein the pharmaceutical composition is formulated for intravenous administration.

11. A method of treating a patient with cancer, the method comprising:
    (a) identifying a patient in need of treatment; and
    (b) administering to the patient a therapeutically effective amount of the pharmaceutical composition of claim 9, wherein the MHC class I monomer comprises an epitope expressed by the patient's cancer.

12. The method of claim 11, wherein the patient is a human patient.

13. The method of claim 11, wherein the patient has an autoimmune disease or disorder.

14. The method of claim 11, wherein the cancer is a primary or secondary tumor.

15. The method of claim 14, wherein the primary or secondary tumor is within the patient's breast, lung, skin, kidneys, bladder, head, neck, lymphatic system, liver, brain, esophagus, digestion system, stomach or ovaries.

16. The method of claim 11, wherein the cancer is melanoma.

17. The method of claim 11, wherein the nanoparticle comprising the single chain variable fragment of an anti-αCTLA-4 antibody or anti-αPD-1 antibody has reduced toxicity or reduced side effects when administered as part of the nanoparticle as compared to when the single chain variable fragment of an anti-αCTLA-4 antibody or anti-αPD-1 antibody is administered alone or not as part of the nanoparticle.

18. The method of claim 11, wherein the administration of the pharmaceutical composition is combined with a second and different pharmaceutical composition.

19. A method of making an immune-tolerant elastin-like polypeptide (iTEP) tetramer, the method comprising: mixing one or more iTEP fusion peptides with four or more biotinylated MHC class I monomers, wherein the one or more iTEP fusion peptides comprise in amino terminal-to-carboxy terminal order a (i) a HisTag; (ii) a linker; (iii) four or more streptavidin moieties, (iv) a first iTEP sequence, wherein the first iTEP sequence is (Gly-Ala-Gly-Val-Pro-Gly)$_{70}$ (SEQ ID NO: 20), (v) a second iTEP sequence, wherein the second iTEP sequence is (Gly-Val-Leu-Pro-Gly-Val-Gly)$_{56}$ (SEQ ID NO: 21), and (vii) a cysteine containing tag under conditions to allow four or more biotinylated MHC class I monomers to bind to the four or more streptavidin moieties of the iTEP fusion peptide,
   wherein the four or more biotinylated MHC class I monomers are H2-D$^b$/gp100 epitope, H2-K$^b$/TRP-1 epitope, H2-K$^b$/TRP-2 epitope, or MHC class I tumor-associated epitopes,
   wherein the binding of the four or more biotinylated MHC class I monomers to the four or more streptavidin moieties of the iTEP fusion peptide results in an iTEP-tetramer.

20. The method of claim 19, wherein the cysteine containing tag comprises a tetracysteine motif.

21. The method of claim 20, wherein the tetracysteine motif is Gly-Cys-Gly-Cys-Gly-Cys-Gly-Cys (SEQ ID NO: 22).

22. A purified immune-tolerant elastin-like polypeptide (iTEP)-tetramer produced by the method of claim 19.

23. A method of making a nanoparticle, the method comprising:
    a) mixing one or more immune-tolerant elastin-like polypeptide (iTEP) fusion peptides with four or more biotinylated MHC class I monomers, wherein the one or more iTEP fusion peptides comprise in amino terminal-to-carboxy terminal order a (i) a HisTag; (ii) a linker; (iii) four or more streptavidin moieties, (iv) a first iTEP sequence, wherein the first iTEP sequence is (Gly-Ala-Gly-Val-Pro-Gly)$_{70}$ (SEQ ID NO: 20), (v) a second iTEP sequence, wherein the second iTEP sequence is (Gly-Val-Leu-Pro-Gly-Val-Gly)$_{56}$ (SEQ ID NO: 21), and (vii) a cysteine containing tag under conditions to allow four or more biotinylated MHC class I monomers to bind to the four or more streptavidin moieties of the iTEP fusion peptide, wherein the MHC class I monomers are H2-D$^b$/gp100 epitope, H2-K$^b$/TRP-1 epitope, H2-K$^b$/TRP-2 epitope, or MHC class I tumor-associated epitopes, and wherein the binding of the four or more biotinylated MHC class I monomers to the four or more streptavidin moieties of the iTEP fusion peptide results in an iTEP-tetramer;
    b) mixing the iTEP-tetramer with an iTEP-fusion molecule, wherein the iTEP-fusion molecule comprises (i) a HisTag; (ii) a linker; (iii) single chain variable fragment (scFv) of an anti-αCTLA-4 antibody or anti-αPD-1 antibody; (iv) a first iTEP sequence, wherein the first iTEP sequence is (Gly-Ala-Gly-Val-Pro-Gly)$_{70}$ (SEQ ID NO: 20); (v) a second iTEP sequence, wherein the second iTEP sequence is (Gly-Val-Leu-Pro-Gly-Val-Gly)$_{56}$ (SEQ ID NO: 21), and (vi) a cysteine containing tag;
    wherein the iTEP-tetramer and iTEP-fusion molecule are mixed at a ratio of 10:1; and
    wherein the cysteine containing tag in a) and the cysteine containing tag in b) are crosslinked via one or more disulfide bonds; and
    c) oxidizing the one or more disulfide bonds between the iTEP-tetramer and iTEP-fusion molecule, thereby forming a stable nanoparticle.

24. The method of claim 23, further comprising prior to step a) expressing the iTEP fusion in a genetically modified cell.

25. The method of claim 24, further comprising solubilizing the iTEP fusion immediately prior to step a).

26. A kit comprising:
a) one or more immune-tolerant elastin-like polypeptide (iTEP)-tetramers, wherein the one or more iTEP-tetramers comprise in amino terminal-to-carboxy terminal order (i) four MHC class I monomers, wherein the MHC class I monomers are H2-D$^b$/gp100 epitope, H2-K$^b$/TRP-1 epitope, H2-K$^b$/TRP-2 epitope, or MHC class I tumor-associated epitopes, (ii) a first iTEP sequence, wherein the first iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21), (iii) a second iTEP sequence, wherein the second iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21), and (iv) a cysteine containing tag; and
b) one or more iTEP-fusion molecules, wherein the one or more iTEP-fusion molecules comprise in amino terminal-to-carboxy terminal order (i) a HisTag; (ii) a linker; (iii) single chain variable fragment (scFv) of an anti-αCTLA-4 antibody or anti-αPD-1 antibody; (iv) a first iTEP sequence, wherein the first iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21); (v) a second iTEP sequence, wherein the second iTEP sequence is (Gly-Ala-Gly-Val-Pro-Gly)$_{70}$ (SEQ ID NO: 20) or (Gly-Val-Leu-Pro-Gly-Val-Gly)$_{56}$ (SEQ ID NO: 21) and (vi) a cysteine containing tag.

27. The kit of claim 26, wherein the cysteine containing tags of the one or more iTEP-tetramers and the cysteine tags of the one or more iTEP-fusion target peptides are not crosslinked.

28. The kit of claim 26, further comprising a reducing agent.

29. The kit of claim 26, further comprising an oxidizing agent.

30. The kit of claim 27, wherein thiol groups of the cysteine containing tags of the one or more iTEP-tetramers and the cysteine tags of the one or more iTEP-fusion target peptides are protected.

* * * * *